(12) United States Patent
Long et al.

(10) Patent No.: US 6,740,493 B1
(45) Date of Patent: May 25, 2004

(54) BONE PRECURSOR CELLS: COMPOSITIONS AND METHODS

(75) Inventors: Michael W. Long, Northville, MI (US); Kenneth G. Mann, Grand Isle, VT (US)

(73) Assignee: The Regents of the University of Michigan, Ann Arbor, MI (US)

( * ) Notice: Subject to any disclaimer, the term of this patent is extended or adjusted under 35 U.S.C. 154(b) by 1367 days.

(21) Appl. No.: 08/793,053

(22) PCT Filed: Aug. 11, 1995

(86) PCT No.: PCT/US95/10293

§ 371 (c)(1), (2), (4) Date: Apr. 14, 1997

(87) PCT Pub. No.: WO96/05290

PCT Pub. Date: Feb. 22, 1996

Related U.S. Application Data

(63) Continuation-in-part of application No. 08/289,794, filed on Aug. 12, 1994, now Pat. No. 5,972,703.

(51) Int. Cl.$^7$ .................. G01N 33/53; A61K 39/395; C07K 16/00; C07K 16/28
(52) U.S. Cl. ................ 435/7.1; 435/7.2; 435/7.21; 424/140.1; 424/145.1; 424/158.1; 530/388.23; 530/388.24; 530/413
(58) Field of Search ................ 435/7.1, 7.2, 7.21; 424/140.1, 145.1, 158.1; 530/388.23, 388.24, 413

(56) References Cited

U.S. PATENT DOCUMENTS

| | | | |
|---|---|---|---|
| 4,474,893 A | * | 10/1984 | Reading |
| 4,722,899 A | * | 2/1988 | Hamaoka et al. |
| 4,904,259 A | | 2/1990 | Itay ............................ 623/16 |
| 5,061,620 A | | 10/1991 | Tsukamoto et al. ........ 435/7.21 |
| 5,108,753 A | | 4/1992 | Kuberasampath et al. .. 424/422 |
| 5,118,667 A | | 6/1992 | Adams et al. ............... 514/12 |
| 5,197,985 A | | 3/1993 | Caplan et al. ............... 623/16 |
| 5,226,914 A | | 7/1993 | Caplan et al. ............... 623/16 |

FOREIGN PATENT DOCUMENTS

| | | |
|---|---|---|
| EP | 0 455 482 A2 | 11/1991 |
| WO | WO 92/22584 | 12/1992 |

OTHER PUBLICATIONS

Long et al Journal of Bone and Mineral Research vol. 8 Suppl 1 Abstract 987, Jul. 1993.*
Robbins et al Pathological Basis of Disease Fifth Edition WB Saunders Co pp. 1218–1223, 1232–1240, 1994.*
Seaver Genetic Engineering News vol. 14(14) pp. 10 and 21, 1994.*
Seiver et al Clin Chem vol. 27 (11) 1797–1806, 1981.*
Eastell et al J Clinical Endocrinol and Metab vol. 67(4) 741–748, 1988.*
Delmas et al J Bone Mineral Res vol. 5(1) 5–11, 1990.*
Stenner et al Proc Natl Acad Sci USA vol. 83 6892–6896, Sep. 1986.*
Dox et al Harpers Illustrated Medical Dictionary p. 433, 1993.*
Stedman's Medical Dictionary 24th Edition p. 1095, 1982.*
Fedarko et al Journal of Cellular Physiology 151;215–227, 1992.*
Ashton et al., "Distribution of fibroblastic colony–forming cells in rabbit bone marrow and assay of their osteogenic potential by an in vivo diffusion chamber method," *Calcif. Tissue Int.*, 36:83–86, 1984.
Bab et al., "Kinetics and differentiation of marrow stromal cells in diffusion chambers in vivo," *J. Cell Sci.*, 84:139–151, 1986.
Bleiberg, "Colony forming cell–fibroblast development in extracellular matrix–induced bone and bone marrow formation in rat," *Connect. Tissue. Res.*, 14:121–127, 1985.
Bleiberg et al., "New bone formation and bone marrow differentiation induced in rats by extracellular bone matrix implantation: Effect of local preirradiation on the process," *Ex. Hematol.*, 15:309–315, 1987.
Casser–Bette et al., "Bone formation by osteoblast–like cells in a three–dimensional cell culture," *Calcified Tissue Int.*, 46:46–56, 1990.
Friedenstein et al., "Marrow microenvironment transfer by heterotopic transplantation of freshly isolated and cultured cells in porous sponges," *Exp. Hematol.*, 10:217–227, 1982.
Friedenstein et al., "Bone marrow osteogenic stem cells: in vitro cultivation and transplantation in diffusion chambers," *Cell Tissue Kinet.*, 20:263–272, 1987.
Gehron –Robey et al., "Osteoblasts synthesize and respond to transforming growth factor–type β (TGF–β) in vitro," *J. Cell Biol.*, 105:457–463,1987.
Gehron–Robey et al., "The Cellular Biology and Molecular Biochemistry of Bone Formation," In: *Disorders of Bone and Mineral Metabolism*, Coe & Favus, Eds., Ch. 11, 241–263, 1992.

(List continued on next page.)

*Primary Examiner*—Anthony C. Caputa
*Assistant Examiner*—Karen A. Canella
(74) *Attorney, Agent, or Firm*—Fulbright & Jaworski

(57) ABSTRACT

Disclosed are compositions of bone precursor cells and methods for their preparation and use. Bone precursor cells are cells which are not hematopoietic and which can differentiate into osteoblasts upon exposure to a bone growth factor and deposit calcium into the extracellular matrix. Such bone precursor cells are useful in the treatment of certain bone related disorders and diseases, such as osteoporosis, or in promoting fracture repair. In addition, methods of differentiating bone precursor cells into osteoblasts, and other diagnostic and even prognostic methods are provided.

11 Claims, 11 Drawing Sheets

OTHER PUBLICATIONS

Howlett et al., "Mineralization in in Vitro Cultures of Rabbit Marrow Stromal Cells," *Clin. Orthop.,* 213:251–263, 1986.

Kassem et al., "Formation of Osteoblast–like cells from human mononuclear bone marrow cultures," *APMIS,* 99:269–274, 1991.

Lian & Stein, "Concepts of osteoblast growth and differentiation: basis for modulation of bone cell development and tissue formation," *Crit. Rev. Oral Biol. Med.,* 3:269–305, 1992.

Long et al., "Characterization of Human Bone Marrow–Derived Osteoprogenitor Cells," *Journal of Bone and Mineral Research,* Abstract #987, 8(1):S363, 1993.

Luria et al., "Bone formation in organ cultures of bone marrow," *Cell Tissue Res.,* 248:449–454, 1987.

Maniatopoulos et al., "Bone formation in vitro by stromal cells obtained from bone marrow of young adult rats," *Cell Tissue Res.,* 254:317–330, 1988.

Mardon et al., "Development of osteogenic tissue in diffusion chambers from early precursor cells in bone marrow of adult rats," *Cell Tissue. Res.,* 250:157–165, 1987.

Marks & Popoff, "Bone cell biology: The regulation of development, structure, and function in the skeleton," *Am. J. Anat.,* 183:1–44, 1988.

McCulloch et al., "Osteogenic progenitor cells in rat bone marrow stromal populations exhibit self–renewal in culture," *Blood* 77(9):1906–1911, 1991.

Muthukumaran & Reddi, "Bone matrix–induced local bone induction," *Clin. Orth. Rel. Res.,* 200:159–164, 1985.

Owen et al., "Clonal analysis in vitro of osteogenic differentiation of marrow CFU–F," *J. Cell Sci.,* 87:731–738, 1987.

Reddi & Cunningham, "Bone induction by osteogenin and bone morphogenetic proteins," *Biomaterials,* 11:33–34, 1990.

Recker, "Embryology, Anatomy, and Microstructure of Bone," In: *Disorders of Bone and Mineral Metabolism,* Coe & Favus, Eds., Ch. 10,219–240, 1992.

Turksen & Aubin, "Positive and negative immunoselection for enrichment of two classes of osteoprogenitor cells," *J. Cell Biol.,* 114:373–384, 1991.

Bruder and Caplan, "First bone formation and the dissection of an osteogenic lineage in the embryonic chick tibia is revealed by monoclonal antibodies against osteoblasts," *Bone,* 10(5):359–75, 1989. Medline abstract.

Chiba and Matsuyama, "Immunohistochemical localization of bone Gla protein and osteonectin in normal human bone and cartilage tissues, and in osteosarcomas and chondrosarcomas," *Nippon Seikeigeka Gakkai Zasshi,* 67(5):463–72, May, 1993, Medline abstract.

Choong et al., "Induction of osteoblast differentiation by ascorbic acid, retnoic acid, and calcitrol," *Front. Osteosarcoma Res.,* pp. 331–334, 1993. Medline abstract.

Harris et al., "Effects of transforming growth factor beta on bone nodule formation and expression of bone morphogenetic protein 2, osteocalcin, osteopontin, alkaline phosphatase, and type I collagen mRNA in long–term cultures of fetal rat calvarial osteoblasts," *J. Bone Miner. Res.,* 9(6):855–63, Jun., 1994. Medline abstract.

Haynesworth et al., "Characterization of Cells with Osteogenic Potential from Human Marrow," *Bone,* 13:81–88, 1992.

Long et al., "Regulation of Human Bone Marrow–derived Osteoprogenitor Cells by Osteogenic Growth Factors," *J. Clin. Invest.,* 95:881–887, Feb., 1995.

Malaval et al., "Cellular expression of bone–related proteins during in vitro osteogenesis in rat bone marrow stromal cell cultures," *J. Cell Physiol.,* 158(3):555–72, Mar., 1994.

Mohan and Baylink, "Bone Growth Factors," *Clin. Orthop.,* 263:30–48, 1991.

Shortman, "The Separation of Lymphoid Cells on the Basis of Physical Parameters: Separation of B–and T–Cell Subsets and Characterization of B–Cell Differentiation Stages," *In: Methods of Cell Separation,* vol. 1, Plenum Press, New York, pp. 229–249, 1977.

Turksen et al., "Isolation of monoclonal antibodies recognizing rat bone–associated molecules in vitro and *in vivo,*" *J. Histochem. Cytochem.,* 40(9):1339–52, Sep., 1992.

Yamaguchi et al., "Recombinant human bone morphogenetic protein–2 stimulates osteoblastic maturation and inhibits myogenic differentiation in vitro," *J. Cell Biol.,* 113(3):681–7, May, 1991.

Zhou et al., "Differential effects of transforming growth factor –beta 1 and bone morphogenetic protein 4 on gene preosteoblasts," *J. Cell Physiol.,* 155(1):112–9, Apr., 1993.

International Search Report dated Dec. 29, 1995. PCT/US 95/10293.

Gronthos, S., S. E. Graves, O. Ohta, and P. J. Simmons. "The STRO–1+ Fraction of Adult Human Bone Marrow Contains the Osteogenic Precursors." *Blood.* 84:4164–4173, 1994.

Long, et al., "Expression of Human Bone–related Proteins in the Hematopoietic Microenvironment." *J. Clin. Invest.,* 86:1387–1395, 1990.

Long, et al., "Synergistic Regulation of Human Megakaryocyte Development." *J. Clin. Invest.,* 82:1779–1786, 1988.

Simmons, et al. "Molecular Cloning of a cDNA Encoding CD34, a Sialomucin of Human Hematopoietic Stem Cells." *J. Immunol.,* 148:267–271, 1992.

* cited by examiner

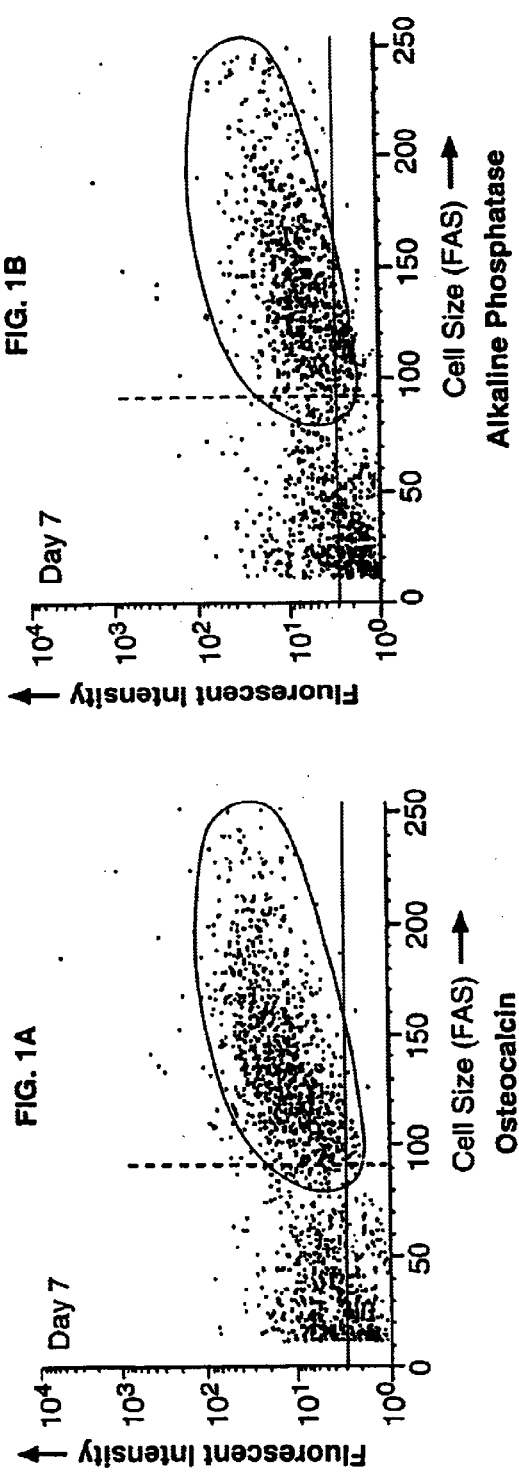

BONE PRECURSOR CELLS: COMPOSITIONS AND METHODS

The present application is a continuation-in-part of U.S. patent application Ser. No. 08/289,794, filed Aug. 12, 1994 now U.S. Pat. No. 5,972,703, as well as the 35 U.S.C. §371 national stage of the international application PCT/US95/10293, filed on Aug. 11, 1995, the entire text and figures of which disclosure is specifically incorporated herein by reference without disclaimer.

The U.S. Government may own rights in the present invention pursuant to grant numbers PO1-AG-08777 and 43460.

FIELD OF THE INVENTION

This invention relates generally to methods for obtaining bone precursor cells and compositions comprising such cells. The invention includes methods for enriching the population of bone precursor cells in bone marrow cells isolated from mammalian bones or peripheral blood. Also provided are methods for differentiating bone precursor cells into osteoblasts, and diagnostic and even prognostic methods.

BACKGROUND OF THE INVENTION

The rate of bone fractures in the United States is estimated at 6,000,000 individuals per year. In 1984 (Holbrock et al., 1984) these injuries resulted in a direct cost (i.e., excluding loss of income) of $17,000,000,000 per year. When a bone is completely fractured, a significant number of fractures require medical intervention beyond simple immobilization (casting), particularly those involving trauma. A major problem in such instances is the lack of proximity of the two bone ends (referred to as non-union). This results in an inappropriate and prolonged repair process, which may prevent recovery.

The average length of time for the body to repair a fracture is 25–100 days, for moderate load-bearing, and one year for complete repair. Thus, both simple fractures and medically complicated breaks would benefit from novel therapeutic modalities which accelerate and/or complete the repair process. The same is true for those bone diseases (referred to as osteopenias) which result in a thinning of the bone the primary symptom of which is an often-debilitating fracture.

Primary Osteoporosis is an increased, progressive bone loss which accompanies the aging process. As such, it represents significant health risk in the United States which greater than 15 million Americans suffering from primary (idiopathic) osteoporosis resulting in a direct cost of $6,000,000,000 per year (Holbrock et al., 1984). Primary osteoporosis is the most common of the metabolic bone diseases, and some 40,000–50,000 fracture-related deaths per year are attributed to this disorder. This mortality rate is greater than deaths due to cancer of the breast and uterus, combined. Significantly, this disorder, which is one of the osteopenias, is asymptomatic until a bone fracture occurs. Affected individuals typically fracture the radius, femoral head, or collapse vertebrae.

Osteoporosis has a greater impact on the female population with larger numbers of women than men struck by this disorder, and a significant increase in the rate of osteoporosis occurs post-menopause. The rate of osteoporosis in these women is slowed but not ameliorated by estrogen replacement therapy. Indeed, there is no convincing medical evidence that any treatment is successful in restoring lost bone mass of any kind. Given the aging of the American population, patients with osteoporosis also represent a significant target population for effective and novel bone therapies.

The process of aging in general is associated with a progressive diminution of bone-accumulation capacity, especially in trabecular bone (Nimni et al., 1993). This decreased structural integrity is associated with a number of alterations in bone proteins, osteoid formation, calcium loss etc., leading to osteopenia (Nimni et al., 1993; Fedarko et al., 1992; Termine, 1990). The exact cellular mechanisms underlying such changes in bone structure and function are unclear. However, central to all of these alterations are cells of the osteoblast lineage.

Reductions in osteoblast function or numbers, of necessity, leads to the loss of bone-forming capacity. It is known that some aspects of osteoblast function decrease greatly with age (Termine, 1990). Overall, total protein synthesis and the synthesis of specific proteoglycans decreases markedly (Fedarko et al., 1992), whereas collagen and other proteins such as fibronectin and thrombospondin are degraded (Termine, 1990).

Bone cells from older individuals, in vitro, have the capacity to respond to growth factors, but their synthetic and proliferative capacity is diminished (Termine, 1990), presumably due to reduced responsiveness to various osteogenic growth factors (Pfeilschifter et al., 1993). This results in diminished bone precursor cell and osteoblast numbers (Nimni et al., 1993).

There is no current treatment for lost bone mass, including various growth-promoting proteins and Vitamin $D_3$. Likewise, there is no effective replacement or implant for non-union fractures or crush injuries of the bone. Currently, these latter types of injury utilize bovine (cow), or human cadaver bone which is chemically treated (to remove proteins) in order to prevent rejection. However, such bone implants, while mechanically important, are biologically dead (they do not contain bone-forming cells, growth factors, or other regulatory proteins). Thus, they do not greatly modulate the repair process. All of these concerns demonstrate a great need for new or novel forms of bone therapy.

Bone development results from the proliferation of mesenchymal cells, their differentiation into osteogenic progenitor cells, and the eventual calcification of cartilage and bone extracellular matrix (Urist et al., 1983). Human bone marrow contains a distinct cell population that expresses bone proteins and responds to growth factor $\beta 1$ (TGF-$\beta$), but not to hematopoietic growth factors (Long et al., 1990).

Little information exists concerning the growth factors or cytokines controlling development of bone precursor cells (osteoprogenitor cells and preosteoblasts) into their differentiated progeny, the osteoblasts. Likewise, few studies address the impact of extracellular matrix (ECM) molecules on this stage of human bone cell development, or the impact of aging on either of these two areas. In the past, human bone cells (both precursor cells and osteoblasts) have been technically difficult to acquire and purification/characterization studies or protocols were few in number. Additionally, current in vitro models of bone formation are limited as the use of post-fetal mesenchymal tissue to generate bone cells often results in chondrogenesis, but is inadequate for osteogenesis, (Urist et al., 1983). Thus, information concerning the cellular activation signals, differentiation, and bone matrix production during the early phases of human bone cell development is limited, at best.

The regulation of chondro-osteogenic gene activation is induced during bone morphogenesis by an accumulation of extracellular and intracellular signals (Urist et al., 1983). Importantly, extracellular signals are known to be transferred from both cytokines and extracellular matrix molecules (Urist et al., 1983), to responding cell surface receptor(s) resulting in eventual bone formation. The formation of bone occurs by two mechanisms. Direct development of bone from mesenchymal cells (referred to as intramembranous ossification; as observed in skull formation) occurs when mesenchymal cells directly differentiate into bone tissue. The second type of bone formation (the endochondral bone formation of skeletal bone) occurs via an intervening cartilage model.

The development and growth of long bones thus results from the proliferation of mesenchymal cells, their differentiation into osteogenic progenitor cells and (then) osteoblasts, cartilage deposition, and eventual calcification of the cartilage and/or bone matrix. Concurrently, bone is remodeled to form a tubular bone space in which hematopoietic cell differentiation occurs.

Interestingly, the number of osteoprogenitor cells in adult bone seems too small to replace all of the large mass of bone normally remodeled in the process of aging of skeleton (Urist et al., 1983). Further observations (vide infra) confirm this concept by showing that one (unexpected) source of osteoprogenitor cells is the bone marrow. This reduced progenitor cell number also implies that there is a disassociation of bone progenitor cell recruitment from subsequent osteogenic activation and bone deposition, and further suggests multiple levels of regulation in this process.

One of the central issues concerning bone formation regards the developmental lineages of the bone cell types, namely the osteoblast and the osteoclast. There is adequate evidence to suggest that osteoblasts arise from local mesenchymal cell populations, and that osteoclasts are derived from blood-born monocyte/macrophage cells.

Fischman and Haye first demonstrated that monocytes fused to form osteoclasts in regenerating newt limbs (Fishman et al., 1962). Although the role of macrophage fusion remains controversial (Hattersley et al., 1989 and Horton et al., 1985), further evidence for the blood-born origin of the osteoclast was pioneered by LeDouarin using a chick:quail chimera in which nuclear morphology allows clear distinction of cell derivation. These studies conclusively demonstrated that osteoblasts and osteocytes are derived from the limb bud mesenchyma whereas osteoclasts arise from blood-born hematopoietic cells (Jotereau et al., 1978 and Le Douarin, 1973). The importance of these observations was subsequently shown by the successful cure (by osteoclasts) of osteopetrosis utilizing bone marrow transplantation in both animals (Ash et al., 1980), and humans (Coccia et al., 1980). While such data conclusively show the hematogenous origin of the osteoclast, little knowledge exists on the nature or location of the stem cell population(s) capable of differentiating into bone-forming osteoblasts.

Like other developing tissues, bone responds to bone-specific, and other soluble growth factors. TGF-β is a member of a family of polypeptide growth regulators that affect cell growth and differentiation during developmental processes, such as embryogenesis and tissue repair (Sporn et al., 1985). TGF-β strongly inhibits proliferation of normal and tumor-derived epithelial cells, blocks adipogenesis, myogenesis, and hematopoiesis (Sporn et al., 1985). However, in bone, TGF-β is a positive regulator.

TGF-β is localized in active centers of bone differentiation (cartilage canals and osteocytes) (Massague, 1987), and TGF-β is found in high quantity in bone—suggesting that bone contains the greatest total amount of TGF-β (Massague, 1987 and Gehron Robey et al., 1987). During bone formation, TGF-β also promotes chondrogenesis (Massague, 1987)—an effect presumably related to its ability to stimulate the deposition of extracellular matrix (ECM) components (Ignotz et al., 1986). Besides stimulating cartilage formation, TGF-β is synthesized and secreted in bone cell cultures, and stimulates the growth of sub-confluent layers of fetal bovine bone cells, thus showing it to be an autocrine regulator of bone cell development (Sporn et al., 1985).

In addition to TGF-β, other growth factors or cytokines are implicated in bone development. Urist and co-workers have been able to isolate various regulatory proteins that function in both in vivo and in vitro models (Urist et al., 1983). Bone morphogenic protein (BMP), originally an extract of demineralized human bone matrix, has now been cloned (Wozney et al., 1988), and when implanted in vivo results in a sequence of events leading to functional bone formation (Wozney et al., 1988 and Muthukumaran et al., 1985). The implanting of BMP is followed by mesenchymal cell migration to the area of the implant, differentiation into bone progenitor cells, deposition of new bone, and subsequent bone remodeling to allow the establishment of bone marrow (Muthukumaran et al., 1985).

A number of additional growth factors exist which regulate bone development. In particular, bone-derived growth factors (BDGF) stimulate bone cells to proliferate in serum-free media (Hanamura et al., 1980 and Linkhart et al., 1986). However, these factors seem to function at a different level from BMP (Urist et al., 1983).

The extracellular matrix (ECM) varies in its tissue composition throughout the body, consisting of various components such as collagen, proteoglycan, and glycoprotein (Wicha et al., 1982). Numerous studies point to the influences of ECM in promoting cellular development. Gospodarowicz et al. demonstrated that ECM, the natural substrate surrounding cells in vivo, greatly affects corneal epithelial cell proliferation in vitro (Gospodarowicz and Ill, 1980 and Gospodarowicz et al., 1980). Studies by Reh et al. (1987) show that extracellular components such as laminin are involved in inductive interactions which give rise to retinal and retinal pigmented endothelium. Also, differentiation and growth of mammary epithelial cells are profoundly influenced by ECM components, and mammary cell growth in vivo and in vitro requires type IV collagen (Wicha et al., 1982), Finally, studies from one of the inventor's laboratories show that bone marrow ECM also plays a major role in hematopoiesis in that complex ECM extracts greatly augment cell proliferation (Campbell et al., 1985), and that marrow-derived ECM contains specific cytoadhesion molecules (Campbell et al., 1987; Campbell et al., 1990; Long and Dixit, 1990; Long et al., 1990; and Long et al., 1992).

A number of non-collagenous matrix proteins, isolated from demineralized bone, are involved in bone formation. Osteonectin is a 32 kDa protein which, binding to calcium, hydroxyapatite and collagen, is believed to initiate nucleation during the mineral phase of bone deposition (Termine et al., 1981). In vivo analysis of osteonectin message reveals its presence in a variety of developing tissues (Nomura et al., 1988 and Holland et al., 1987). However, it is present in its highest levels in bones of the axial skeleton, skull, and the blood platelet (megakaryocyte) (Nomura et al., 1988).

Bone gla-protein (BGP, osteocalcin) is a vitamin K-dependent, 5700 Da calcium binding bone protein that is specific for bone and may regulate Ca++ deposition (Termine et al., 1981; Price et al., 1976; and Price et al., 1981). Other bone proteins seem to function as cytoadhesion molecules (Oldberg et al., 1981 and Somerman et al., 1987), or have unresolved functions (Reddi, 1981).

While bone morphogenesis is ECM dependent, bone ECM also contains a number of the more common mesenchymal growth factors such as PDGF, basic, and acidic fibroblast growth factor (Urist et al., 1983; Linkhart et al., 1986; Hauschka et al., 1986; and Canalis et al., 1985). These activities are capable of stimulating the proliferation of mesenchymal target cells (BALB/c 3T3 fibroblasts, capillary endothelial cells, and rat fetal osteoblasts). As well, bone-specific proliferating activities such as the BMP exist in bone ECM.

While these general and specific growth factors undoubtedly play a role in bone formation, little is understood concerning the direct inductive/permissive capacity of bone-ECM or bone proteins themselves on human bone cells or their progenitors. Nor is the role of bone ECM in presenting growth factors understood—such "matricrine" (factor:ECM) interactions may be of fundamental importance in bone cell development but have not been well characterized.

SUMMARY OF THE INVENTION

The present invention provides the isolation, purification and characterization of precursors to osteoblasts, and the identification of human osteoprogenitor cells. Immunological separation of bone marrow non-adherent low-density (NALD) cells results in a marked enrichment of bone precursor cells that express osteocalcin, osteonectin, and bone alkaline phosphatase.

The bone precursor cells of the present invention, although isolatable from bone marrow, are not part of the bone marrow stromal cell compartment, nor are they a component of the hematopoietic cell lineages. The lack of a stromal cell nature is demonstrated by the failure to isolate these cells from human stromal cell isolates, and physical cell separation by density centrifugation. These cells are not hematopoietic as demonstrated by their failure to express the pan-hematopoietic cell antigen CD34, and their failure to respond to hematopoietic growth factors.

In addition to other distinguishing features, the present invention is distinct from the prior art in that the prior art studies are generally confined to osteogenic cultures in which bone cells are observed in bone marrow-derived stromal cell populations (Gronthos et al., 1994; Friedenstein et al., 1987; Luria et al., 1987; Turksen and Aubin, 1991; Van Vasselaer et al., 1994). Given the combined physical and immunological separation disclosed herein, the present population of bone precursor cells likely represents an earlier stage of bone precursors than the prior art, in that the present immune-isolated cells are not intimately associated with the endosteal surface of the bone marrow trabeculae.

Flow cytometric analyses show that distinct cell subpopulations exist among these isolated cells. The majority of the bone protein, antigen-positive cells are preosteoblasts, approximately the size of a lymphocyte, whereas other, antibody-separated subpopulations consist of osteoblasts and osteoprogenitor cells. In serum-free cultures, TGF-β stimulates the small, antigen-positive cells to become osteoblasts as these cells both increase in size, cellular complexity, and express increased levels of osteocalcin and alkaline phosphatase.

Antibody-separated cells also contain a separate population of progenitor cells that form colonies of osteoblast cells when cultured in serum-free, semi-solid media. Two types of these osteoprogenitor cells are observed: a colony-forming cell (CFC) that generates several hundred bone antigen-positive cells, and a more mature cluster-forming cell that has a lesser proliferative potential and thus generates clusters of 20–50 antigen-positive cells.

Osteopoietic colony-forming cells and cluster-forming cells have an obligate, but differential requirement for osteogenic growth factors. The CFCs respond to TGF-β, basic fibroblast growth factor (bFGF), bone morphogenetic protein-2 (BMP-2), and 1,25-dihydroxy vitamin D3 (1,25-OH D3). In contrast to the colony-forming cells, cluster-forming cells are regulated predominately by 1,25-OH D3 and TGF-β, but fail to respond to bFGF.

The inventors thus defined that human bone marrow contains a non-hematogenous, heterogeneous population of bone precursor cells among which exists a population of proliferating osteoprogenitor cells. The present provision of these bone precursor cell populations in sufficient numbers allows evaluation of their role in osteogenesis in both health and disease.

In one aspect, the present invention provides a process for preparing an enriched population of bone precursor cells. The process generally comprises the steps of:

(a) obtaining a population of cells that include bone precursor cells;

(b) enriching the population for bone precursor cells by exposing the population of cells to a bone precursor cell antibody immunoreactive with a bone precursor cell antigen; and (c) removing cells of the population that do not immunoreact with a bone precursor cells antibody.

The population of cells that includes bone precursor cells may be a population of bone marrow cells, a population of cells isolated from bone, or a population of peripheral blood cells.

Bone precursor cells can be further enriched by equilibrium-density centrifugation of the population of bone marrow or peripheral blood cells. Equilibrium-density centrifugation of the cell population provides low density bone marrow cells enriched in bone precursor cells with a density of between about 1.050 and about 1.090 gm/cm$^3$, preferably between 1.060 and 1.085 gm/cm$^3$.

In another aspect, stromal cells present, e.g., in bone marrow cells, can be removed by exposing bone marrow cells to an adherent surface, typically tissue culture plastic or tissue culture glass.

In yet another aspect, an enriched population of bone precursor cells is further fractionated according to size. In one embodiment, size fractionation can be accomplished by fluorescence activated flow cytometry, velocity sedimentation, or counter-flow centrifugal elutriation. Bone precursor cells of the present invention generally have average diameters of between about 8 microns and about 70 microns, and preferably, of between about 10 microns and about 20 microns.

Antibodies are used to enrich the population of bone precursor cells. Suitable antibodies include any antibody immunoreactive with a bone precursor cell. Bone precursor cell antibodies particularly contemplated by the present invention include anti-osteocalcin, anti-osteonectin, and anti-bone alkaline phosphatase.

Physico-chemical separation techniques, such as equilibrium density centrifugation, can be used to obtain a moderate enrichment of bone precursor cells, e.g., to a level of about 6–7% purity. Density separation and plastic adherence are used to further increase the purity of such cells.

A significant contribution of the present invention is the use of immunoseparation techniques to obtaining substantially purified populations. The use of immuneadherence separation generates substantially pure populations of human bone precursor cells. As used herein, the term "substantially pure" refers to a population of bone precursor cells that is between about 60% and about 80% pure. Immuno-magnetic separation, preferably using anti-osteonectin and anti-osteocalcin antibodies, yields an almost homogeneous or essentially pure population of bone precursor cells. The term "essentially pure", as used herein, refers to a population of bone precursor cells that is about 95% pure.

In using a second antibody immunoreactive with a bone precursor cell antibody, enhanced enrichment of the population of bone precursor cells is thus achieved. In one embodiment, antibodies are conjugated to a solid substrate including: tissue culture plastic, agarose, other plastics, polyacrylamide, or magnetic particles.

The present invention thus provides a population of bone precursor cells enriched about 100-fold or more over the starting materials, i.e., over the bone marrow cells or peripheral blood cells that include bone precursor cells. More preferably, the population of bone precursor cells is enriched between about 1,000-fold and about 2,000-fold, or between about 2,000-fold and about 3,000-fold, or between about 3,000-fold and about 4,000-fold, over the starting cell population, with enrichment of up to about 4,800-fold being achievable.

In one embodiment, mammalian bone precursor cells are contemplated by the present invention. In a preferred embodiment, bone precursor cells from human bone marrow cells are contemplated.

The present invention further provides a composition comprising bone precursor cells. Bone precursor cells as provided herein generally have the following characteristics:

(a) immunoreactive with a bone precursor cell antibody;
(b) average cell diameter of 8 microns to about 70 microns; and
(c) differentiate into osteoblasts upon exposure to tissue growth factor β, 1,25-OH Vitamin D3, basic fibroblast growth factor, or bone morphogenic protein 2.

In one aspect, the composition comprising bone precursor cells can be prepared as described above from mammalian bone, bone marrow, or peripheral blood cells. Bone precursor cells of the present invention include cells immunoreactive with anti-osteocalcin, anti-osteonectin or anti-bone alkaline phosphatase. In one embodiment, bone precursor cells express osteocalcin, osteonectin or alkaline phosphatase but do not express the pan-hematopoietic antigen CD34. In a preferred embodiment, bone precursor cells include osteoprogenitor cells and preosteoblasts.

In yet another aspect, a method of differentiating a bone precursor cell into an osteoblast is provided by the present invention. The method generally comprises the steps of:

(a) obtaining a population of bone precursor cells according to the procedure described above;
(b) exposing the bone precursor cell to a growth factor; and
(c) cultivating the bone precursor cell under serum free conditions to differentiate the bone precursor cell into an osteoblast.

Growth factors contemplated include transforming growth factor β, insulin-like growth factor (IGF) and platelet-derived growth factor (AA, A/B, and B/B isoforms) 1,25-OH Vitamin D3, basic fibroblast growth factor, or bone morphogenic protein. In one embodiment, a bone precursor cell is exposed to a single growth factor. Alternatively, a bone precursor cell can be exposed to two or more growth factors.

In another embodiment, the method of differentiating a bone precursor cell into an osteoblast further comprises cultivating the bone precursor cell in the presence type I collagen, fibrinogen, fibrin, vitronectin, thrombospondin, osteocalcin, or osteonectin. In one embodiment, bone precursor cells are cultivated in the presence of type I collagen, fibrinogen and fibrin. In an alternative embodiment, bone precursor cells are cultivated in the presence of type I collagen, fibrinogen, fibrin, vitronectin, thrombospondin, osteocalcin, and osteonectin.

The present invention further provides diagnostic and prognostic methods. In certain embodiments, the invention therefore includes methods for identifying a subject at risk of developing an age-related bone disorder, which methods generally comprise the steps of:

(a) obtaining a population of cells from the subject, the population being enriched for human bone precursor cells; and
(b) quantifying the amount of a bone precursor related protein, such as, e.g., osteocalcin or osteonectin, expressed by the bone precursor cells, wherein an increased or otherwise altered amount of the protein, in comparison to the amount within the bone precursor cells of a young or middle-aged subject, is indicative of a subject at risk of developing an age-related bone disorder, such as osteoporosis.

A currently preferred example of this method includes the steps of:

(a) obtaining a population of cells from the subject, the population being enriched for human bone precursor cells; and
(b) quantifying the amount of osteocalcin or osteonectin expressed by the bone precursor cells, wherein an increased amount of osteocalcin or osteonectin, in comparison to the amount within the bone precursor cells of a young or middle-aged subject, is indicative of a subject at risk of developing an age-related bone disorder, such as osteoporosis.

These methods are generally based on the finding that osteonectin and osteocalcin antigenic expression by human preosteoblast cells increases with increasing age in a statistically significant manner. Osteonectin expression is particularly elevated in older subjects (an increase from 59 to 89 arbitrary log units).

Further methods of the invention include the diagnosis of particular groups or sub-sets of elderly subjects that have, or are at risk of developing, a certain type of bone disease or disorder, particularly osteoporosis or osteopenias or another of the group of bone disorders connected with increased aging. These methods generally comprise:

(a) obtaining a population of cells from the elderly-subject, the population being enriched for human bone precursor cells; and
(b) quantifying the amount of osteocalcin or osteonectin expressed by the bone precursor cells, wherein a decreased amount of osteocalcin or osteonectin, in comparison to the average amount within the bone precursor cells of an elderly subject, is indicative of an elderly subject having a particular type of osteoporosis, osteopenia or age-related change in bone formation.

Decreased amounts of osteocalcin and osteonectin, and most particularly, decreased amounts of osteonectin, in elderly subjects have been discovered to be indicative of an elderly subject having a particular type of osteoporosis, osteopenia or other disorder associated with age-related changes in bone formation, such as those individuals having a more severe form of osteoporosis.

This is based upon the inventors' findings that the majority of bone precursor cells from a certain sub-set of elderly subjects belonged to an antigen-dull population. As elderly subjects with bone disorders can generally be characterized into two main groups, and as the methods of the invention generally allow two main types of bone precursor cells to be identified (one of which is the antigen-dull population), the diagnostic utility of the invention in distinguishing between these two groups is evident.

In any of the diagnostic or prognostic methods, the composition comprising the bone precursor cells will generally be prepared as described above and may be obtained from a human bone marrow or peripheral blood sample. The enrichment steps of the cell preparation method will preferably provide for a significantly purified human bone precursor cell population, will more preferably include an immunomagnetic separation step, and will most preferably include immunomagnetic separation using anti-osteocalcin and/or anti-osteonectin antibodies.

The most preferred method of quantifying the amount of osteocalcin or osteonectin expression is to use fluorescence activated flow cytometry. However, the use of other immunological methods, such as RIAs, ELISAs, and the like, is certainly contemplated; as is the use of molecular biological methods based upon the hybridization of DNA segments, probes or primers comprising osteocalcin or osteonectin sequences.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

FIG. 1 in four panels shows flow cytometric analysis of immune-adherent bone marrow derived bone precursor cells. The circled area represents larger osteoblast cells. FIG. 1A shows cells which express osteocalcin. FIG. 1B shows cells that express bone alkaline phosphatase. FIG. 1C shows the differentiation of bone precursor cells that express osteocalcin into osteoblasts. FIG. 1D shows the differentiation of bone precursor cells that express bone alkaline phosphatase into osteoblasts.

FIG. 2 in two panels shows the In Vitro Expansion of TGF-β stimulated bone marrow derived osteoblasts.

FIG. 3 in two panels shows two photographs of human bone marrow derived osteoprogenitor colonies.

FIG. 4 in two panels shows the responsiveness of colony-forming and cluster-forming osteoprogenitor cells to various growth factors.

FIG. 5 in three panels shows the immunophenotypic characterization of human preosteoblast and osteoblast cells. Human bone precursor cells were isolated by immune-adherence or immunomagnetic separation. For back-gating, antigen positive cells were electronically marked (identified by square regions in the figure) and antigen negative or dull cells similarly marked (as identified by circles in the figure; upper sub-panels, right and left) These marked populations were then displayed to show their forward angle and side-scatter characteristics.

FIG. 6 in two panels shows co-expression of osteonectin and osteocalcin by purified populations of human bone precursor cells. Human bone precursor cells were purified by combined physico-chemical separation (density and plastic-adherence) and immunomagnetic separation, and then simultaneously incubated with antibodies to osteonectin and osteocalcin. FIG. 6A and FIG. 6B are divided into four quadrants that are numbered and referred to in the text.

FIG. 7 in two panels shows expression of osteonectin and osteocalcin in younger and older individuals. FIG. 7B shows purified human bone precursor cells evaluated for osteonectin. Bone protein expression by human preosteoblast cells from a single representative young individual (9 years old) is indicated by the open profile and a representative older (60 yrs) individual by the shaded profile. These individuals were chosen as representative because their mean-specific, and peak-fluorescence values were identical to the average determined for their age-cohorts, and their coefficients of variation were similar.

FIG. 10 in two panels shows the labeling and adhesion of human bone precursor cells to extracellular matrix proteins and cytokines. Human bone precursor cells were purified by immunomagnetic separation as described in FIG. 6A and FIG. 6B. The cells were then labeled with a "caged" fluorochromes (calcein, an acetylmethyl ester derivative of fluroisothiocyanate).

DETAILED DESCRIPTION OF THE INVENTION

Figure 2A:
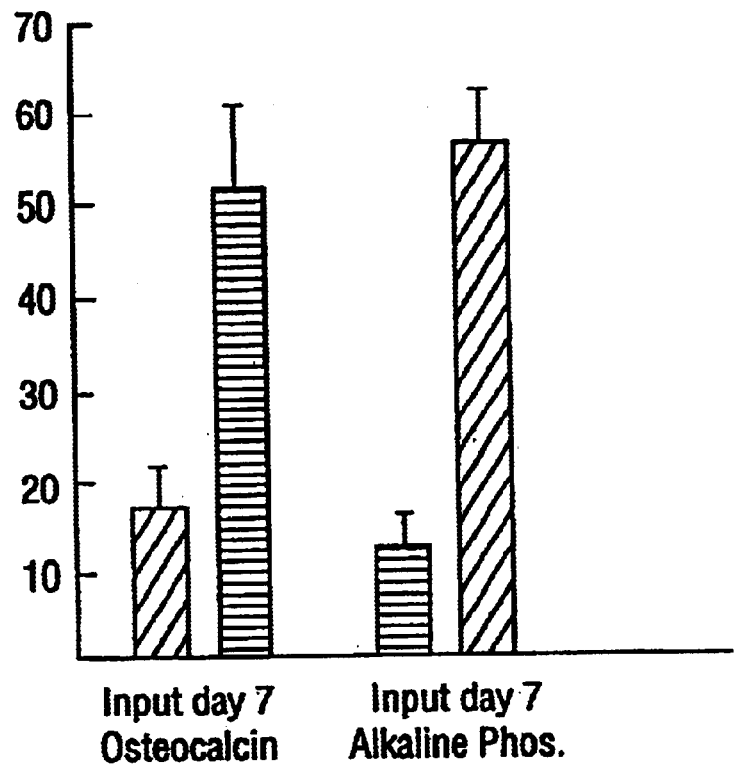
FIG. 2A shows the increase in the frequency of osteoblasts following 7 days of culture in the presence of TGF-β.

The present invention provides a process for preparing an enriched population of bone precursor cells. The process generally comprises the steps of:

(a) obtaining a population of cells that include bone precursor cells;

(b) enriching the population for bone precursor cells by exposing the population of cells to a bone precursor cell antibody immunoreactive with a bone precursor cell antigen; and (c) removing cells of the population that do not immunoreact with a bone precursor cells antibody.

In one embodiment, mammalian bone precursor cells are contemplated by the present invention. In a preferred embodiment, bone precursor cells from human bone marrow cells are contemplated.

In certain embodiments, bone precursor cells may be obtained from a population of bone marrow cells. In other embodiments, bone precursor cells may be obtained from a population of peripheral blood cells.

As used herein, a bone precursor cell is any cell that is capable of differentiating or expanding into an osteoblast cell. A bone precursor cell of the present invention is not hematopoietic and thus does not express the pan-hematopoietic antigen CD34. Preferred bone precursor cells include osteoprogenitor cells of both the colony forming cell type and the cluster forming cell type and preosteoblast cells. As described in Example 1, colony forming osteoprogenitor cells are antecedent to cluster forming osteoprogenitor cells, and to preosteoblast cells in the differentiation process.

Bone precursor cells can be further enriched by equilibrium-density centrifugation of the starting cell population. Equilibrium-density centrifugation of such cells provides low density cells enriched in bone precursor cells with a density of between about 1.050 and about 1.090 gm/cm$^3$.

In a preferred embodiment, the density of bone precursor cells is between about 1.060 and about 1.085 gm/cm$^3$. In one embodiment, equilibrium-density centrifugation can be performed before the antibody purification of step (b) above. In this embodiment, the antibody purification step is carried out on bone marrow cells with a density of between about 1.050 and about 1.090. In a second embodiment, equilibrium-density centrifugation can be performed after the antibody purification of step (b) above. Alternatively, the equilibrium-density centrifugation purification step can be performed twice—once before the antibody purification of step (b) above, and once after the antibody purification step.

In another aspect, the population of bone precursor cells can be enriched by removing stromal cells present, e.g., in bone marrow cells. Removal of stromal cells can be accomplished by exposing, e.g., bone marrow cells, to an adherent surface, typically tissue culture plastic or glass. Stromal cells adhere to tissue culture plastic or glass while bone precursor cells do not. Stromal cells can be removed before or after the immune purification step. Preferably, stromal cells are removed prior to the immune purification step. The use of solid surfaces such as tissue culture plastic or glass is well known in the art. Tissue culture plastic and glass can be treated (e.g. silicone, nitrocellulose, nickel, etc.) to promote or inhibit cell adhesion. Treated and untreated surfaces are available commercially.

In another aspect, an enriched population of bone precursor cells is further fractionated according to size. In a preferred embodiment, size fractionation can be accomplished by fluorescence activated flow cytometry. Bone precursor cells of the present invention have average diameters of between about 8 microns and about 70 microns. Preferably, bone precursor cells have average diameters of between about 10 microns and about 20 microns.

Notably, the use of multi-parameter flow cytometry shows that there are two size populations among immune adherent cells, and TGF-β-induced differentiation results in a shift between the small and large cell compartment. In order to further examine the developmental characteristics of these cells, isolated uninduced and induced cells were electronically divided into small and large cell compartments and "back-gated" to determine the side-scatter characteristics of each. For back-gating, antigen-positive, or negative cells are electronically marked and these marked populations re-analyzed to show their forward angle (i.e., cell size) and side-scatter (i.e., cell content) characteristics).

These data show that the larger osteoblast cells also have the highest degree of intracellular organization (side-scatter characteristics). This was seen in both uninduced cells (in which osteoblast-sized cells represent approximately 5% of the isolate) and induced cells. Thus, the TGF-β-induced differentiation of human bone precursor cells results in an increase in antigenic content, cell size, and an increase in intracellular complexity. Isolated cells also contain a population of cells in which antigen density is little different from non-specific antibody controls. Back-gating of this population consistently shows these cells as having a low degree of side-scatter. These characteristics (i.e., low side-scatter and small size) are consistent with a residual population of lymphoid-like which do not bear detectable bone antigens.

The present invention provides an enriched population of bone precursor cells from about 100-fold over the starting material of bone marrow or peripheral blood cells that include the bone precursor cells. Enrichment of between about 1,000-fold and about 2,000-fold, between about 2,000-fold and about 3,000-fold, between about 3,000-fold and about 4,000-fold over the original bone marrow or peripheral blood cells is possible, with enrichment of up to about 4,800-fold being described herein.

Bone precursor cells of the present invention are immunoreactive with bone precursor cell antibody. A bone precursor cell antibody is used to enrich the population of bone precursor cells. Bone precursor cell antibodies contemplated by the present invention include anti-osteocalcin, anti-osteonectin, and anti-bone alkaline phosphatase. Anti-osteocalcin, anti-osteonectin, and anti-bone alkaline phosphatase are described in Shull et. al., 1984; incorporated herein by reference. As bone precursor cells are further characterized, other antibodies which immunoreact with a bone precursor cell may be generated by one of ordinary skill in the art. The use of these other antibodies immunoreactive with a bone precursor cell is contemplated.

In a preferred embodiment, a bone precursor cell antibody is conjugated to a solid substrate. The solid substrate is preferably a tissue culture or petri dish. The use of solid surfaces such as tissue culture plastic or glass is well known in the art. Tissue culture plastic and glass can be treated (e.g. silicone, nitrocellulose, nickel, etc.) to promote or inhibit protein adhesion. Treated and untreated surfaces are available commercially.

As discussed in detail in Example 1, antibody coated tissue culture dishes are utilized to "pan" for bone precursor cells. Briefly, bone marrow cells containing bone precursor cells are incubated on antibody coated dishes. Bone precursor cells adhere to the antibodies while all other cells do not adhere to the dish. After incubation, the dish non-adherent cells are removed by gently washing the dish with media. Bone precursor cells are removed from the dish and further analyzed, purified or differentiated into osteoblasts.

In another embodiment, a second antibody immunoreactive with a bone precursor cell antibody can be used to enrich the population of bone precursor cells. The use of a secondary antibody is generally known in the art. Typically, secondary antibodies are antibodies immunoreactive with the constant regions of the first antibody. Preferred secondary antibodies include anti-rabbit, anti-mouse, anti-rat, anti-goat, and anti-horse and are available commercially.

In a preferred embodiment, secondary antibodies are conjugated to a solid substrate including tissue culture dish, agarose, polyacrylamide, and magnetic particles. In this embodiment, a bone precursor cell antibody is first immunoreacted to a bone precursor cell. The bone precursor cell with the attached antibody is next exposed to the secondary antibody that is conjugated to a solid substrate. Enrichment of precursor cells is achieved because only cells that present a bone precursor cell antibody immunoreact with the secondary antibody. A commercially available kit provides secondary antibodies conjugated to magnetic particles. In this system, bone precursor cells that present a bone precursor cell antibody are purified by exposure to a magnetic field.

Although physico-chemical separation (equilibrium density centrifugation) results in a moderate enrichment of bone precursor cells to a level of about 6–7% purity, and density separation followed by plastic adherence further increases the purity, immunoseparation techniques are particularly preferred for obtaining substantially purified populations. The use of immuneadherence separation generates substantially pure (~60–80%) populations of human bone precursor cells. Immuno-magnetic separation based on the osteonectin and osteocalcin antigens yields an almost homogeneous, i.e., about 95% pure, population of cells. This represents an approximate 4,800-fold purification over unfractionated bone marrow.

Immunomagnetically separated cells were subjected to two-color fluorescence-activated cytometry to examine the expression of osteonectin and osteocalcin. These data show that the isolated cells co-express both proteins. Moreover, antigen-density contour plots demonstrate that these antigens are co-expressed in a single population of cells, in that no distinct sub-populations of single-antigen positive cells are detected. There remains, however, a small population of antigen-dull cells.

Unlike the antigenically null-population seen in cells separated by immune-adherence, the magnetically separated antigen-low or dull cells have the same side-scatter characteristics as the double-positive cell population. Given that these cells are recovered following two passes through the magnetic isolation column, it is unlikely that these are contaminating lymphoid cells (as are seen in immune adherence-based separation). Rather, they represent cells with a sufficient (albeit low) antigen density (albeit a low density) to retain them on the column in the presence of a magnetic field.

The preparation of bone precursor cell antibodies was reported in Shull et al., 1989, incorporated herein by reference. Both polyclonal and monoclonal antibodies are contemplated by the present invention. Means for preparing and characterizing antibodies are well known in the art (See, e.g., *Antibodies "A Laboratory Manual*, E. Harlow and D. Lane, Cold Spring Harbor Laboratory, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a rabbit, a mouse, a rat, a hamster, a sheep or a guinea pig. Because of the ease of use and relatively large blood volume of rabbits, a rabbit is a preferred choice for production of polyclonal antibodies.

A monoclonal antibody can be readily prepared through use of well-known techniques such as those exemplified in U.S. Pat. No. 4,196,265, herein incorporated by reference.

Typically, a technique involves first immunizing a suitable animal with a selected antigen (e.g., osteocalcin, osteonectin or bone alkaline phosphatase) in a manner sufficient to provide an immune response. After a sufficient time to induce an immune response, spleen cells from the immunized animal are then fused with cells of an immortal myeloma cell. A number of immortal myeloma cells are available and the choice of the immortal cell is within the skill of an artisan. Immortal myeloma cells lack the salvage pathway of synthesizing nucleotides.

The fused spleen/myeloma cells are cultured in a selective medium to select fused spleen/myeloma cells from the parental cells. Fused cells are separated from the mixture of non-fused parental cells by the addition of agents that block the de novo synthesis of nucleotides in the tissue culture media. Unfused myeloma cells lack the enzymes necessary to synthesize nucleotides from the salvage pathway and are selectively killed in the selective media. Unfused lymphocytes also do not continue to grow in tissue culture. Thus, only cells that have successfully fused (hybridoma cells) can grow in the selection media. The hybridoma cell produces a monoclonal antibody.

The present invention further provides a composition comprising bone precursor cells. Bone precursor cells as provided herein have the following characteristics:

(a) immunoreactive with a bone precursor cell antibody;
(b) average cell diameter of about 8 microns to about 70 microns; and (c) differentiate into osteoblasts upon exposure to tissue growth factor β, 1,25-OH Vitamin D3, basic fibroblast growth factor, or bone morphogenic protein.

In addition, bone precursor cells have low side scatter (right-angle light scatter) characteristics by flow cytometry.

In one embodiment, the composition comprising bone precursor cells can be prepared as described above from mammalian bone marrow cells. Bone precursor cells include cells immunoreactive anti-osteocalcin, anti-osteonectin or anti-bone alkaline phosphatase. In one embodiment, bone precursor cells express osteocalcin, osteonectin or alkaline phosphatase but do not express the pan-hematopoietic antigen CD34. In a preferred embodiment, bone precursor cells include osteoprogenitor cells or preosteoblasts.

The differentiation cascade of bone precursor cells into an osteoblast is as follows:

Colony forming cell→Cluster forming cell→Preosteoblast→Osteoblast.

Osteoprogenitor cells are herein defined as cells that proliferate to yield differentiated bone cells (preosteoblasts or osteoblasts) as their progeny. The osteoprogeniter cells are of two types: a colony forming cell or a cluster-forming cell. A cluster forming cell is a progenitor cell with limited proliferative. potential. As discussed in Example 1, a cluster forming cell differentiates into a colony of 20–50 bone-protein antigen-positive (e.g. osteocalcin) cells after about 7 days of incubation.

A colony forming cell is a progenitor cell with increased proliferative potential. After around 7 days of incubation, a colony forming cell differentiates into several hundred intensely bone antigen-positive cells.

A preosteoblast is a cell that differentiates into an osteoblast.

It is understood that these developmental stages cannot be defined precisely. As used herein, a bone precursor cell is any cell that is capable of differentiating or expanding into an osteoblast. A bone precursor cell of the present invention includes osteoprogenitor cells, colony forming cells, cluster forming cells and preosteoblast cells.

Although not the only means of definition, human bone preosteoblast cells may be characterized as small lymphocyte-sized cells with low side-scatter characteristics (SSC). Human preosteoblast cells may also be characterized as $OC^{lo}$, $ON^{lo}$, $AP^{lo}$, $CD34^-$, $SSC^{lo}$, and $FAS^{lo}$. Human osteoblast cells may be characterized as OC++, ON++, AP++, $CD34^-$, $SSCh^{hi}$, $FAS^{hi}$.

In yet another aspect, a method of differentiating a bone precursor cell into an osteoblast is provided by the present invention. The method generally comprises the steps of:

(a) obtaining a population of bone precursor cells according to the procedure described above;

(b) exposing the bone precursor cell to a growth factor; and (c) cultivating the bone precursor cell under serum free conditions to differentiate the bone precursor cell into an osteoblast.

Growth factors used include transforming growth factor β, 1,25-OH Vitamin D3, basic fibroblast growth factor, or bone morphogenic proteins. In one embodiment, a bone precursor cell is exposed to a single growth factor. Alternatively, a bone precursor cell can be exposed to two or more growth factors.

Upon exposure to a growth factor, the bone precursor cell differentiates into an osteoblast. Culturing the precursor cell for seven days in the presence of a growth factor causes the cell to enlarge approximately 3-fold (FIG. 1A, FIG. 1B, FIG. 1C, FIG. 1D). There is also a 5-fold increase in the antigenic content of the cell. Furthermore, the total number of osteoblasts increase approximately 4–5 fold (FIG. 2). These results are discussed in greater detail in Example 1.

In still another embodiment, the method of differentiating a bone precursor cell into an osteoblast further comprises cultivating the bone precursor cell in the presence of type I collagen, fibrinogen, fibrin, polyglycolic acid, polylactic acid, osteocalcin, or osteonectin. In one embodiment, bone precursor cells are cultivated in the presence of type I collagen, fibrinogen, and fibrin. In one embodiment, type I collagen, fibrinogen, fibrin, polyglycolic acid, polylactic acid, osteocalcin, or osteonectin is used alone in the presence of a growth factor. In an alternative embodiment, bone precursor cells are cultivated in the presence of type I collagen, fibrinogen, fibrin, osteocalcin, and osteonectin. It is understood that any combination of the compounds listed above in this paragraph is contemplated by the present invention.

Bone precursor cells cultivated in the presence of type I collagen, fibrinogen, fibrin, osteocalcin, and osteonectin produced an extracellular matrix similar to bone. These cultures were positive in the Von Kossa reaction and were capable of depositing calcium ino the extracellular matrix. Bone precursor cells cultivated in a collagen/fibrin matrix are useful in therapeutic applications.

This invention provides a cellular product of isolated, purified animal bone precursor cells, and the means to expand these bone cells as a transplantation therapy for osteopenias. In this modality, an animal's own bone precursor cells, or those of a histocompatible donor, can be removed and if necessary, expanded in culture. Next, these cells or an ex vivo, expanded number of these bone-forming cells, are transplanted into animals with bone formation deficits. The use of an autologous animal bone precursor cell transplant would avoid graft rejection. Autologous or allogeneic bone cell transplantation will be of therapeutic importance in the treatment of osteopenias. In the majority of these disorders, the tightly linked balance of bone formation and bone reabsorption is disrupted, with reabsorption being predominant. The infusion of large numbers of bone-forming cells will thus augment bone formation in diseases such as osteoporosis.

Purified animal bone precursor cells are also an ideal target for animal gene therapy for bone disorders, in which a known, specific molecular defect results in abnormal bone formation. The ability to isolate and stimulate the division of bone precursor cells demonstrates that they can be used as target cells for gene therapy of congenital bone defects.

Another use of animal bone precursor cells is a cell-based biological matrix which is implanted in animals requiring any form of bone repair or bone union. This product is comprised of bone cells imbedded within a biologically active protein matrix. The biomatrix consists of defined bone proteins (e.g. type I collagen, osteonectin, fibrinogen, fibrin and osteocalcin), and specific bone growth factors (above) which stimulate bone cell proliferation. Alternatively, polyglycolic acid and/or polylactic acid can also be present. The bio-matrix acquires its consistency (that of a firm gel) and shape by the activation of fibrinogen as a protein polymer and the subsequent gel transition of collagen.

The cells used in this wholly biological implant are the animal's own bone precursor cells (i.e. the cells are autologous and therefore not rejected, see above) which are isolated, and (if needed) expanded in tissue culture. This expansion results in a population of early bone-forming cells which is then embedded within the bio-matrix by polymerization of the gel protein. The result is a "pre-bone" implant containing the animal's own bone cells which would rapidly reorganize the implant and mineralize it. Moreover, the gel-phase will allow this bone substitute to be formed in any necessary shape, thus facilitating small-bone replacement, its use in periodontal disease, or cosmetic repair.

Bone precursor cells can be obtained by a variety of immunologically-based procedures. These are comprised of, but not limited to, fluorescence-activated flow cytometry, immunological-based column chromatography, antibody-conjugated sepharose beads (or other inert beads), or other immunology based applications (e.g immuno-magnetic separation). These procedures do not however, define the population of animal bone precursor cells, but rather lead to its isolation. Other physical separation procedures may be applied prior or after the antigenic purification. These are comprised of, but not limited to, equilibrium density centrifugation, velocity sedimentation, or counter-flow centrifugal elutriation.

As well, other antigenic markers may be used to positively or negatively further define these cells. These are comprised of, but not limited to, antigens of the animal major histocompatibility locus (particularly HLA-DRA), hematopoietic antigens (e.g., CD33, CD8, CD10, CD14, CD9, CD20), or other bone proteins.

The animal bone precursor cells described herein are isolated from animal bone marrow. Sources of such marrow are the flat bones of the axial skeleton (ribs, hips, sternum), as well as the humeri, radi, ulanea, tibulae, and fibulae. Additionally, these cells can be obtained from other non-marrow sources including, but not limited to, the periosteum, bone trabeculae, cancellous bone, or the endosteum.

Furthermore, the present inventors have shown that animal bone precursor cells circulate, thus making it possible to recover and purify these cells in animal peripheral blood. Indeed, human bone precursor cells have now been isolated from human peripheral blood and shown to have similar flow cytometry characteristics to those of bone marrow.

The present invention further provides a method of identifying/screening novel bone growth factors. Candidate bone growth factors or cytokines are screened using an enriched population of bone precursor cells. Bone precursor cells are stimulated to differentiate in the presence of a bone growth factor. Newly identified bone growth factors or cytokines are used in the treatment of osteopenias, fractures and could also be used in the aforementioned bone cell bio-matrix implants.

In another embodiment, bone precursor cells can be used to treat osteogenesis imperfecta. *Osteogenesis imperfecta* is a disease with an identified genetic defect. In this embodiment, bone precursor cells from a patient with *Osteogenesis imperfecta* are isolated. A copy of the defective gene without the mutation is introduced into the bone precursor cell through well known transfection/transformation techniques. Bone precursor cells containing the corrected gene are reintroduced into the patient or are first expanded in vitro and then reintroduced into the patient. This procedure can be performed as a heterologous or autologous procedure. A preferred embodiment is through an autologous procedure.

In yet further embodiments, the present invention provides diagnostic methods that may be used to evaluate age-related alterations in human bone precursor cells by assessing bone protein expression. These methods were developed following a series of flow cytometric investigations on immunomagnetically-separated bone precursor cells, which demonstrated that age-related changes in bone protein expression occur with increasing age (see, e.g., Example 4).

The studies were performed on a total of 41 individuals of three age groups: $\leq 25$ years old (mean age 16.4±7 (S.D.) years, range 1.5–24 years, n=15), 50 years old; (mean age 36.6±5 years old, range 26–45 years, n=9) and individuals $\geq 2$ 50 years old (mean age 70.1±12 years, range 53–89 years, n=17).

Human bone precursor cells were isolated and purified cells from individuals in the given age groups and subjected to multi-parameter flow cytometric analysis. As expected, antigenically-purified human bone precursor cells from these three age populations co-express both osteonectin and osteocalcin. Interestingly, osteonectin and osteocalcin antigenic expression by human preosteoblast cells increases with increasing age.

The flow cytometry data clearly illustrate that the human bone precursor cells in older individuals (i.e., $\geq 50$ years of age) express higher amounts of these two bone proteins than do younger individuals (i.e., $\leq 25$ years old). Profiles from middle aged individuals were intermediate to the other two age groups.

In order to determine whether these alterations were statistically significant for the whole population, the mean specific- and peak-fluorescence were determined for each individual in each age group. A significant ($p \leq 0.05$) age-related increase was noted in both the mean specific fluorescence for osteocalcin (BGP) and osteonectin, as well as in the peak fluorescence of each antigen. Osteocalcin shows a moderate but significant change in mean fluorescence, increasing by 21 arbitrary log units. In contrast, osteonectin expression increases to a greater degree in the population of older individuals (an increase from 59 to 89 arbitrary log units).

The inventors further analyzed this increase in bone protein levels by examining the relationship between age and antigenic expression. Although the numbers of individuals of middle age are lower than the other two age-cohorts, it nonetheless appears that the majority of the increase in human bone precursor cell osteonectin and osteocalcin levels occurs between the ages of 15–16 and 35–40.

The observation that osteonectin and osteocalcin expression in purified populations of human bone preosteoblast cells increases with increasing age is consistent with reports showing that serum osteocalcin expression increases with age in both males and females (Delmas et al., 1983; Orwoll and Deftos, 1990). The inventors' observation demonstrates the cellular basis of the reported serum increases in osteocalcin; i.e., the bone precursor cells themselves express increased osteocalcin (as well as osteonectin).

The age-related increase in expression of osteonectin in purified populations of human (non-adherent) preosteoblasts found in this invention is in contrast to that reported by Fedarko et al. (1992). These investigators documented a progressive decrease in osteonectin levels following 15 years of age. However, comparisons of the methods of isolation between the present report, and that of Fedarko's shows that distinctly different cell populations were isolated.

The inventors' separation procedure isolates a population of cells by physico-chemical, and immunological means. In contrast, the Fedarko study examines preosteoblasts/osteoblasts which are enzymatically (collagenase) released from mineralized matrix, and thus differ greatly from those in the present report. Therefore, the present invention and the Fedarako study likely concern cells at different stages of development. For example, early preosteoblasts not intimately associated with endosteal surface may, when so adherent, respond to regulatory signals within the mineralized bone extracellular matrix which result in the down-regulation of expression/synthesis of specific bone proteins.

Of the seventeen individuals greater than 60 years of age evaluated, four (three women, age 64, 88; and 89 years old; one male age 59) did not show the human bone precursor cell immunophenotypic characteristics described above. Rather, the majority (80–90%) of the presumed preosteoblasts isolated from these individuals are similar in antigenic content to the antigen-dull population of cells described above. These individuals thus lack the predominant osteocalcin-positive/osteonectin-positive ($OC^{++}/ON^{++}$) bright population observed in all other individuals (n=37), including their age-related cohort (both male and female).

Given the immunomagnetic retention of these cells on the column, and that the forward-angle and side-scatter characteristics of these cells are identical to that of the antigen-dull cell subpopulation, the inventors conclude that these individuals possess a population of preosteoblasts which differ greatly in their antigenic expression. Consistent with this, the mean and peak fluorescence of both osteonectin and osteocalcin are significantly reduced, even when compared to the youngest age-cohort (Table 2).

These data suggest that a separate subpopulation of individuals exists with distinctly different (lower) human bone precursor cell antigenic content. This sub-population of elderly people in which only a predominant population of antigen$^{dull}$ preosteoblast cells are present could represent subjects with a differentiation blockade or, alternatively, a loss (or masking) of antigen on the preosteoblast.

Early observations suggest that these aspects of the invention have diagnostic and, perhaps, prognostic utility in connection with certain bone disorders. For example, the use of multi-parameter flow cytometry and immunophennotyping may allow the diagnosis and prediction of outcomes (prognosis) of various bone disorders such as primary osteoporosis. There are two types of primary osteoporosis. Type 1 osteoporosis strikes females in the first two decades following menopause, whereas Type 2 osteoporosis effects both males and females in their 6 th and 7th decade of life. The pattern of antigenic expression in human bone precursor cells observed by the inventors shows that elderly individuals ($\geq 60$ years of ago) are of two types: those with statistically high bone antigen content, and those with significantly low antigen content (compared to age-matched controls). This suggests that these values may reflect the disease status of the affected individual's bone function.

Thus, the immuno-phenotypic purification and multi-parameter flow cytometry based characterization of human bone precursor cells provides an important means of defining the cellular and biochemical basis of both age-related, and perhaps also, disease-mediated alterations in bone cells and their precursors. Further, the invention can be used to monitor the outcome of the transplantation of human bone precursor cells into patients with bone formation deficits.

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLE 1

Preparation of Bone Precursor Cells

Bone Marrow Cell Preparation and Culture. Human bone marrow aspirates were obtained from normal volunteers. Bone marrow cells were subjected to adherent cell depletion, and density separation techniques as previously described (Long et al., 1988). Briefly, non-adherent, low density (NALD) cells were prepared by first subjecting the cells to equilibrium-density centrifugation (Ficoll). The resultant mononuclear, low density cells next were subjected to two rounds of plastic adherence and these non-adherent, low density (NALD) cells then subjected to immune-adherence isolation (vide infra). Bone cells were cultured in supplemented McCoy's 5A media (Long et al., 1988) containing 1% ITS+ (Collaborative Research, Bedford, Mass.) as described previously (Long et al., 1990). Antibodies, Immune-Adherence, and Immunochemistry. The expression of bone protein antigens was determined by fluorescence activated flow cytometry, or by immunocytochemistry utilizing a avidin-biotin system as previously described (Long et. al., 1.990; Long and Heffner, 1988). These antibodies are specific for their respective antigens and do not cross-react with other matrix proteins (Stenner et al., 1984 and Shull et al., 1989). The monoclonal antibody to bone alkaline phosphatase (SAOS2-P80) was raised to osteosarcoma cells (Shull et al., 1989). This antibody was proven to detect alkaline phosphatase activity by immunoprecipitation, and by direct protein sequence-analysis of the precipitated antigen. For immune-adherence, monoclonal antibodies to osteocalcin and osteonectin were immobilized onto tissue culture plastic using a procedure described previously (Long et al., 1992). Approximately $2.5–6.5 \times 10^5$ NALD cells per $cm^2$ were incubated on antibody-coated dishes for one hour at 370° C. Subsequently, non-adherent cells were removed with three rounds of gentle washing using serum-free McCoy's media containing 1% BSA. The immune-adherent cells were removed with the aid of a rubber policeman and analyzed for flow cytometry (as input cells) or cultured for seven days in situ in the presence or absence of osteogenic growth factors.

Flow Cytometric Analysis. Flow cytometric analysis was performed using a Becton-Dickinson FACSCAN system and data analyzed with the BD Lysis software program. Controls consisted of autofluorescence as well as non-specific fluorescence detected with isotype-specific murine monoclonal antibody to keyhole lympet hemocyanin obtained from Becton Dickinson. Human osteoblast cells lines (MG63, SAOS2,) were stained with monoclonal antibodies to osteocalcin, and alkaline phosphatase, respectively, and analyzed for fluorescence intensity versus size (forward angle scatter) versus cellular complexity (side scatter) to independently map the position of osteoblast cells in immune isolated bone marrow cell populations. The frequency of osteoblast cells defined as the number of cells occurring in the osteoblast cell region (as defined above; circle in FIG. 1A, FIG. 1B, FIG. 1C, FIG. 1D) is expressed as a percent of total bone antigen positive cells.

Osteogenic Colony-Forming Cells. In order to quantify osteoprogenitor cells in immune-adherent cultures, adherent cells were cultured in situ in a fibrin-clot system. Plasminogen-free fibrinogen (Hematologic Technologies, Burlington Vt.; 2 mg/mL) was treated with human thrombin (1 Unit/mL) to form a fibrin-clot. The known capacity of osteoblasts to produce proteolytic enzymes and thus lyse the clot was overcome by using epsilon-amino caproic acid at a concentration of 5 mM, and repletion with more fibrinogen, as needed. Immunocytochemistry for osteocalcin expression was performed as previously reported (Long et al., 1990), except that diaminobezadine concentration was 3 mg/mL and the substrate incubation period was increased to 2 hours. Immunocytochemistry controls consisted of an inappropriate antibody, secondary antibody only, and diaminobezadine only (to assess endogenous peroxidase activity). These controls were uniformly negative.

Isolation and Enrichment of Bone Protein Expressing Cells. A number of non-collagenous proteins play a role in bone formation. Monoclonal antibodies were utilized to two of these two bone proteins, osteocalcin and osteonectin, both as phenotypic markers of bone cell development, and as a mechanism of isolating bone protein-expressing cells in vitro. Osteonectin (also known as SPARC) is present in high concentration in bone of the axial skeleton and skull (Nomura et al., 1988 and Holland et al., 1987). Osteonectin binds to calcium, hydroxyapatite, and collagen and, thus, may regulate mineral deposition in bone matrix (Termine et al., 1981). Another bone protein, osteocalcin (also known as bone gla-protein or BGP) is a vitamin K-dependent protein that is specific for bone, and also binds calcium (Termine et al., 1981; Hauschka et al., 1975; Price et al., 1976; and Price et al., 1981). The inventors also utilized a monoclonal antibody to bone alkaline phosphatase as a phenotypic marker for bone cells.

The inventors' previous data demonstrated that marrow-derived osteoblasts modify extracellular matrix in an osteogenic fashion (Long et al., 1990). Coupled with the present data on antigenic phenotyping and in vitro expansion, the inventors herein define marrow-derived preosteoblasts as small, proliferating cells (lymphocyte-sized) that express low amounts of bone protein antigens, whereas marrow-derived osteoblast cells are the larger, differentiated progeny of these cells which express high amounts of antigen and, with longer culture, generate an osteoid matrix. FIG. 1A, FIG. 1B, FIG. 1C and FIG. 1D shows the flow cytometric analysis of human non-adherent low-density (NALD) bone marrow cells which were incubated on antibody-coated tissue culture dishes. Immune-adherent bone cell populations were analyzed for expression of bone proteins as well as cell size (forward-angle light scatter; FAS).

FIG. 1A shows osteocalcin positive cells and FIG. 1B shows bone alkaline phosphatase positive cells. Antigen-positive cells are identified as those cells with more fluorescence than the upper limit of non-specific fluorescence seen in antibody controls (shaded area). Osteoblasts cells (circled) were identified as those bone protein antigen-positive cells significantly larger than the upper 95% cell size limit for input NALD cells (dashed line) as well as parallel analyses of human osteoblasts.

Monoclonal antibodies to osteocalcin and osteonectin (Stenner et al., 1984 and Shull et al., 1989) were utilized to capture ("pan") bone protein-expressing NALD cells using conventional immune-adherence technology (Wysocki et al., 1978 and Mage et al., 1992). Immune-adherence isolation produces a markedly enriched population of cells that are 40–60% bone-protein antigen-positive. Subpopulations of these cells were further resolved using multiparameter fluorescence-activated flow cytometry (FIG. 1A, FIG. 1B, FIG. 1C, FIG. 1D).

The first subpopulation comprises the majority of the cells and is distinguished as a group of bone antigen-positive preosteoblasts approximately the size of a lymphocyte. A second population of antigen-positive osteoblasts is larger than the upper 95% limit of unfractionated NALD cell populations and comprises approximately 2–4% of the immune-adherent cell population (FIG. 1A and FIG. 1B). Both antigen-positive small and large cells express osteocalcin, bone alkaline phosphatase (upper right and left panels), and osteonectin. The exact developmental level at which bone precursor cells express these antigens is unknown. However, two-color fluorescence cytometry studies indicate that the majority (a90%) of the immune-isolated cells co-express both osteonectin and BGP (vide infra).

In Vitro Expansion and Differentiation of Bone Marrow Derived Bone Cells. Immune-isolated bone precursor cells were cultivated under serum-free conditions in the presence of TGF-β1. Multi-parameter flow cytometry shows that TGF-β treatment causes the small cells to differentiate into large, bone-protein antigen-positive cells (FIG. 1C and FIG. 1D). Following seven days of serum-free culture, the majority of immune-isolated cells show an approximate 3-fold increase in cell size (as defined by forward-angle light scatter), and a coordinate increase in their antigenic content, as demonstrated by a 0.5- to 1.0-log increase in relative fluorescence.

FIG. 1C and FIG. 1D show the flow cytometric analysis of bone precursor cells cultured for 7 days in the presence of 25 pM TGF-β. FIG. 1C shows the differentiation of osteocalcin positive cells into osteoblasts. FIG. 1D shows the differentiation of bone alkaline phosphatase cells into osteoblasts.

This observation shows that unfractionated marrow. NALD cells contain bone precursor cells which, in long-term, serum-replete cultures, acquired the morphological and functional characteristics of osteoblasts (Long et al., 1990). Thus, these osteoblasts produced bone proteins, and deposited these proteins into the extracellular matrix that, subsequentially, begins mineralization (as indicated by cellular deposition of calcium into the matrix and positive Von Kossa staining) (Long et al., 1990).

Figure 2B:
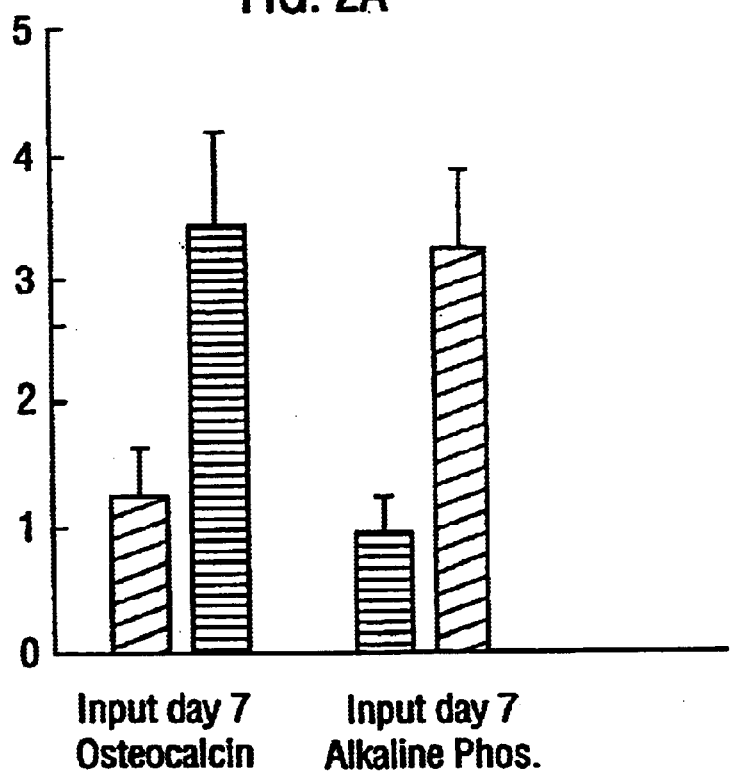
FIG. 2B shows the increase in the total number of osteoblasts following 7 days of culture in the presence of TGF-β.

Examination of such osteoblasts demonstrate that their frequency increases approximately 4–5-fold in the presence of TGF-β (FIG. 2A). This increased cell frequency is due to increased proliferation of bone protein antigen-positive cells. Examination of the total cellularity per culture shows an approximate 3–4-fold in vitro expansion in the total number of osteoblasts over a 7-day period (FIG. 2B), while the antigen-negative cell number remains unchanged or diminished. This is true for both BGP-expressing cells as well as alkaline phosphatase-positive cells.

It is highly unlikely that bone precursor cells die off in culture while the larger osteoblasts proliferate to become the predominant cell population because osteoblasts have low, if any, proliferative capacity. Immune selection of bone protein antigen-positive cells yields a TGF-β-responsive population of small bone precursor cells capable of differentiating into osteoblasts.

In Vitro Development of Human Osteoprogenitor Cells. There exists among the immune-isolated bone precursor cells a true bone progenitor cell, i.e., precursor cells capable of undergoing clonal expansion into differentiated progeny. The clonal nature and in vitro characteristics of progenitor cells in other systems are well described: progenitor cell growth and development requires the presence of at least one mitogenic growth factor, and cell growth in an inert, semi-solid 3-dimensional matrix, which results in the clonal formation of cell colonies by restricting the outgrowth of differentiated progeny (Metcalf et al., 1989). To detect osteoprogenitor cells, immune-isolated NALD cells were over-layered with chemically defined, serum-free media containing fibrinogen—which is subsequently treated with thrombin to form a fibrin-clot. Cells were cultured for 7 days under serum-free conditions in the presence of TGF-β (or other growth factors vide infra). Subsequently, the fibrin clot was dried to a film, and the cultures subjected to immunocytochemical analysis.

Two types of progenitor cell-derived colonies are observed after 7 days. One colony phenotype consists of small clusters of cells containing 20–50 osteocalcin-positive cells (FIG. 3A). By convention, this type of progenitor cell is referred to as a cluster-forming cell (Metcalf et al., 1989 and Metcalf et al., 1983) and represents a progenitor cell with limited proliferative potential. Immune-adherent bone antigen-positive cells were cultured in serum-free tissue culture media (Long et al., 1990) containing plasminogen-free fibrinogen, which was treated with thrombin (Briddell et al., 1990) to form a fibrin-clot. Following 7 days of culture, the fibrin clots were dried to a film, and subjected to immunocytochemical analysis using monoclonal antibodies to human BGP (osteocalcin) as described elsewhere (Stenner et al., 1984).

Figure 3B:
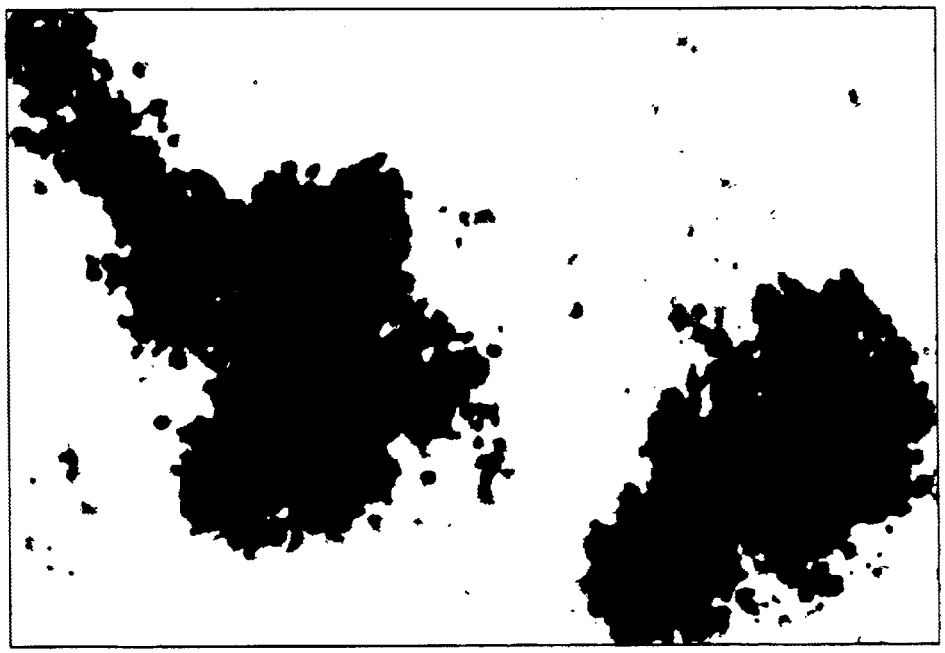
FIG. 3B is a photograph of progeny of osteoprogenitor colony-forming cells.
Figure 3A:
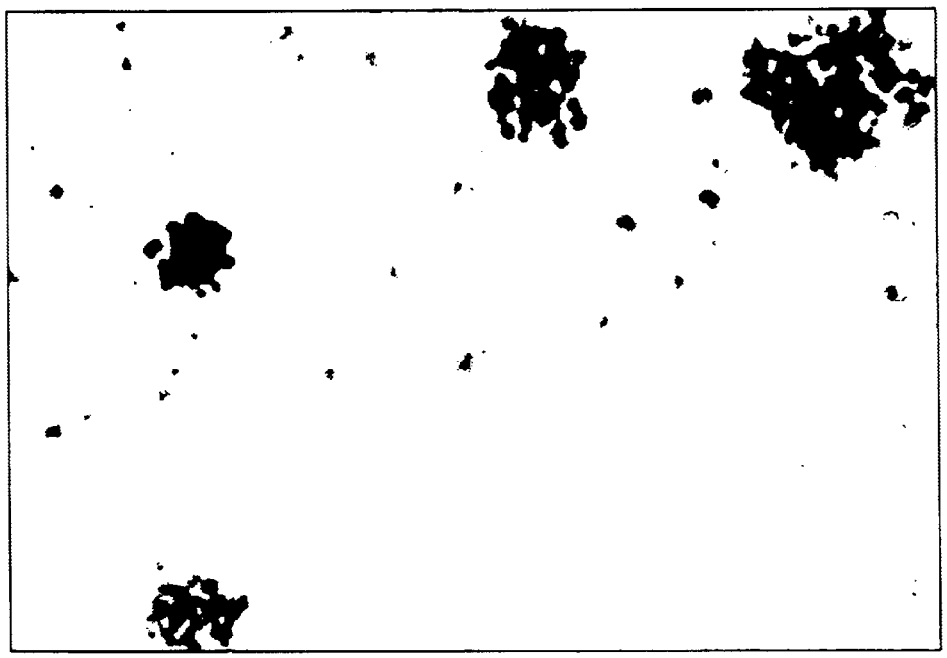
FIG. 3A is a photograph of progeny of osteoprogenitor cluster-forming cells.

The second type of osteogenic cell growth consists of colonies containing several hundred intensely osteocalcin-positive cells (FIG. 3B). This latter type of colony-forming cell (CFC) thus represents an osteoprogenitor cell with an increased proliferative potential. Under appropriate growth factor conditions (see below), this type of progenitor cell is present at 20–50 CFC per $10^5$ total immune-adherent cells. These two types of progenitor cell growth are consistent with previous observations in other systems in which colony-forming cells are thought to be more primitive than cluster-forming cells (Metcalf et al., 1989 and Metcalf et al., 1983). Therefore, the cluster-forming cell represents a later (more mature) stage of bone cell development than the colony forming cell (i.e., the CFC-colony is developmentally antecedent to the CFC-cluster).

Figure 4A:
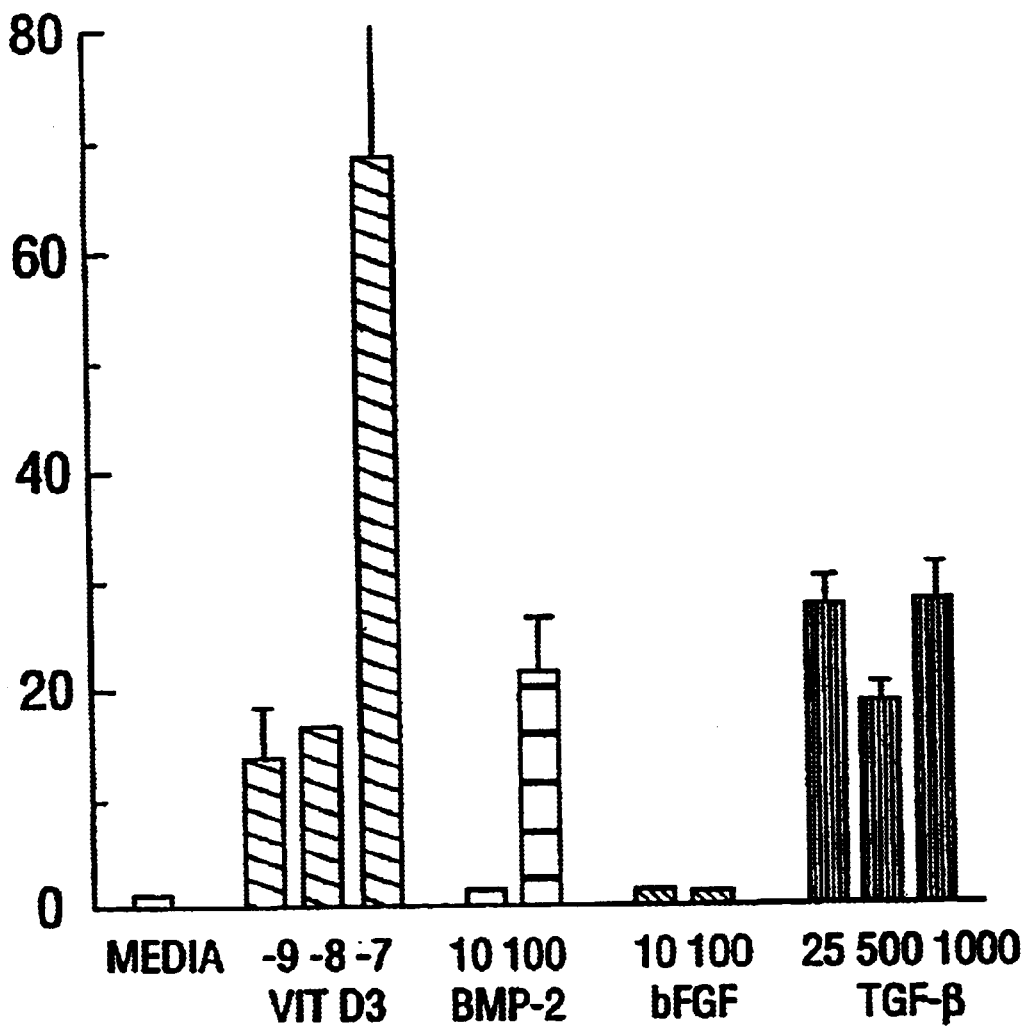
FIG. 4A shows the effect of the labelled growth factors on cluster-forming osteoprogenitor cells.
Figure 4B:
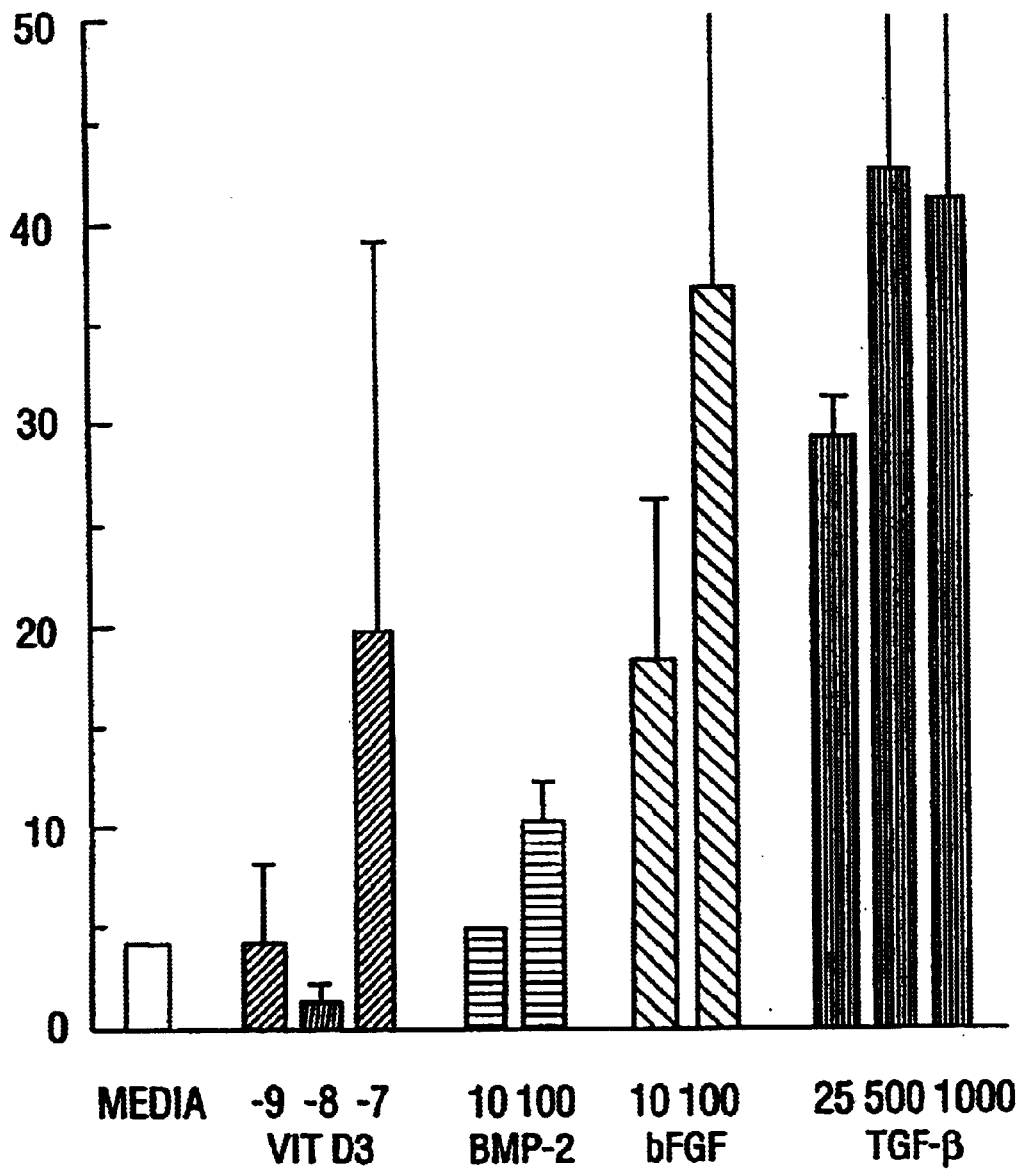
FIG. 4B shows the effect of the labelled growth factors on colony-forming osteoprogenitor cells.

Both cluster-forming, and colony-forming osteoprogenitor cells show an obligate requirement for growth factors, and a differential responsiveness to bone-regulatory cytokines (FIG. 4A and FIG. 4B). Both progenitor cell types fail to develop in the absence osteogenic growth factors (media controls, FIG. 4A and FIG. 4B), whereas the addition of recombinant human growth factors known to regulate osteoblasts (Urist et al., 1983; Hauschka et al., 1986; Noda et al., 1989; Rodan et al., 1989; and Wozney et al., 1988) stimulates both cluster and colony formation. The colony-forming progenitor cells respond equally well to TGF-β and bFGF, generating approximately 40–60 colonies per $10^5$ cells (FIG. 4B). Likewise, 1,25-OH D3 and BMP-2 both stimulate colony forming cells, but to a lesser degree than that seen with TGF-β or bFGF.

The more mature cluster-forming osteoprogenitor cells respond best to 1,25-OH vitamin D3 (vit. D3; values are negative logarithms of molarity), intermediately well to both bone morphogenic protein (BMP-2; values are ng/mL) and transforming growth factor-β (TGF-β; values are pM), but fail to respond to basic fibroblast growth factor (bFGF, values are ng/mL) (FIG. 4A). Bars labeled as "Media" are immune-adherent cells cultured in serum-free conditions without the addition of exogenous growth factors. Interestingly, the observation that bFGF fails to drive the formation of osteogenic clusters suggests a role for this growth factor only in the early phases in bone progenitor cell development.

One of the difficulties in dissecting cell lineages is the need to define precisely developmental stages. The inventors combined immune-isolation, flow cytometric multiparameter analysis, and functional assays (colony-formation and growth factor responsiveness) to characterize human marrow-derived bone precursor cells. Thus, the proliferative component of this lineage consists of two types of osteoprogenitor cells (the colony- and cluster-forming cells) as well as the preosteoblasts, each distinguished by their cell-size, growth factor responsiveness, and proliferative potential. The remaining isolated bone cells are the osteoblast cells that express increased amounts of bone proteins in response to TGF-β1, have a low proliferative potential (if any) and elaborate and mineralize a collagen and non-collagenous bone protein-containing extracellular matrix (Long et al., 1990). These studies show that osteoprogenitor cells are antecedent to bone-forming cells in the following differentiation cascade: Colony forming cell→Cluster forming cell→Preosteoblast→Osteoblast.

Bone precursor cells co-exist among a population of hematopoietic progenitor cells which can be separated from their differentiated progeny by physical methods (i.e., equilibrium density separation, plastic-adherence). Bone marrow-derived bone precursor cells were not hematogenous in origin, as these cells did not express the pan-hematopoietic cell surface antigen CD34, and failed to respond to hematopoietic growth factors (Long et al., 1990). Moreover, unlike the murine system, human bone marrow-initiated bone cell cultures can not be derived from bone marrow stromal cells (Long et al., 1990).

Finally, in later phases of differentiation (i.e., in serum containing, long-term cultures), bone marrow derived osteoblasts produce an extracellular matrix which contains Type I collagen, osteonectin, osteocalcin, and is positive in the Von Kossa reaction; these bone cells also were capable of depositing calcium ($^{45}Ca^{++}$) into the extracellular matrix (Long et al., 1990). These observations and the present data show that a separate lineage of osteopoietic cells exists within human bone marrow. The data also show that, at some stage during their ontogeny, bone precursor cells such as the preosteoblast and, in particular, the osteoprogenitor cell are not intimately associated with the endosteal surface of bone. Rather, these cells may migrate to the endosteum upon acquisition of certain developmental characteristics, such as the expression of bone protein (or other extracellular matrix) receptors. Osteogenic precursors thus exist as a reservoir of bone forming cells within the bone marrow.

EXAMPLE 2

Alterations in Osteoprogenitor Cell Responsiveness to Osteogenic Cytokines During the Aging Process The process of aging is associated with a progressive diminution of bone forming capacity, especially in trabecular bone (Roholl et al., 1994 and Nimni et al., 1993. This process is associated with a number of alterations in bone proteins, osteoid formation, calcium loss etc. leading to osteopenia. Central to all of this is the osteoblast. Reduction in osteoblast numbers of necessity leads to the loss of bone forming capacity. One potential mechanism for such a reduction in osteoblast numbers is a decreased responsiveness of the osteoprogenitor cells to mitogenic activation. As a result, a differentiation blockade may exist somewhere between the osteoprogenitor cell and the osteoblast. Such a blockade has been demonstrated in a rat model system, in which morphometric analysis indicated both a reduction in trabecular bone volume and a (morphological) ten-fold decrease in osteoblast numbers with age (Roholl et al., 1994).

Similarly, a morphological study in humans also indicates an age-related decrease in osteoblast numbers (Nimni et al., 1993). Other studies have indicated that osteoblast cells show a reduced responsiveness to osteogenic growth factors in both humans (Pfeilschifter et al., 1993), and mice (Wong et al., 1992). Again, information on the cytokine responsiveness of human osteoprogenitor cells or preosteoblasts is lacking. The reduction in human osteoblast numbers is likely due to age-related reductions in growth factor responsiveness of the osteoprogenitor cells.

With the inventors' ability to quantify two types of osteoprogenitor cells, preosteoblasts, and osteoblasts, the inventors can quantitatively define the level at which such a block occurs for human cells. If a blockade exists between the osteoprogenitor cell and preosteoblast then numbers of the former will increase in frequency with an attendant decrease in a preosteoblast numbers. A similar alteration in cell ratios is detectable if the blockade is between the preosteoblast and osteoblast.

Age-related changes in cell proliferation are evaluated by stimulating bone precursor cells by various osteogenic cytokines. Certain growth factors (or cytokines), in particular TGF-1 and bFGF, differentially stimulate the early phases of osteoprogenitor cell proliferation. The role of differing cytokines in the proliferation of bone precursor cells in two age groups, 18–25 and ≧50 are of interest. Osteoprogenitor, preosteoblastic, osteoblastic cultures from both age groups with varying concentrations of osteogenic growth factors are cultivated. Given their effect on proliferation, growth factors TGF-β, BMP2, bFGF and 1,25 vitamin D3 are utilized. Other growth factors such as PTH and other BMP family members are also the subject of investigation. Comparison of cell growth for both age groups utilizes all the quantitative methods described above. In addition to concentration dependency, age-related differences in temporal responsiveness to growth factors are examined.

The differential effects for various cytokines at the early and late phases of bone precursor cell proliferation (e.g., TGF-β, and 25-OH vitamin D3, respectively) are investigated. A synergistic interaction may occur if bone precursor cells are cultured simultaneously with these two classes of growth factors. The inventors will thus evaluate a number of relevant combinations of growth factors e.g., TGF-+BMP; TGF-+D3; bFGF+BMP and bFGF+D3.

These studies on cytokine control of osteoprogenitor cell proliferation allow precise determination of any age-related changes in cytokine-responsiveness. In addition, these studies generate important information concerning combinatorial cytokine control of bone cell development. The inventors' ability to examine the osteoprogenitor cells, preosteoblasts, and osteoblasts pinpoints the exact developmental level at which alterations such as a differentiation blockade occur. For example, age-based alterations may show that, while osteoprogenitor cell proliferation is equivalent, a reduced responsiveness of preosteoblasts exists which indicates a defect at this level of development. Thus, each of the three assay types accesses alternative levels of differentiation for defects. Each of the components of the osteogenic microenvironment, purified target cells, purified (and/or) recombinant cytokines/growth factors, and purified extracellular matrix molecules) are available and their interactions are explored in a systematic, controlled fashion. Thus, both positive and negative results can be easily detected at all steps of bone precursor cell proliferation, in both age groups. These studies are limited in that they do not evaluate other types of control such as ECM proteins or failure of osteoblasts to differentiate. These are addressed below in Example 3.

EXAMPLE 3

Cellular Interactions During Osteoprogenitor Cell Proliferation and Differentiation, and How They are Modulated During Aging As is true with other tissue types, bone cell development occurs in a specific microenvironment in which developing bone cells interact with each other, the extracellular matrix, and with matrix:cytokine complexes.

An important but poorly understood component of the osteogenic microenvironment is the extracellular matrix. As mentioned, bone extracellular matrix contains both collagenous and non-collagenous proteins. When bone precursor cells are cultured on certain non-collagenous proteins, they show an increase in proliferation, and in bone cell antigen expression. Moreover, the inventors have shown, using the hematopoietic system as a model, that subpopulations of primitive progenitor cells require both a mitogenic cytokine and a specific extracellular matrix (ECM) molecule in order to proliferate (Long et al., 1992). Indeed, without this obligate matrix:cytokine ("matricrine") signal, the most primitive of blood precursor cells fail to develop in vitro (Long et al., 1992). Although poorly understood, it is likely that a similar requirement exists for human bone precursor cells. Complete evaluation of osteogenic changes occurring with age requires an understanding of the role of ECM molecules in bone precursor cell proliferation.

As mentioned, developing tissue cells interact with a wide variety of regulators during their ontogeny. Each of these interactions is mediated by defined, specific receptor-ligand interactions necessary to both stimulate the cell proliferation and/or motility. Also, both chemical and/or extracellular matrix gradients exist which signal the cell to move into a defined microenvironment (e.g., into the region of a bone fracture). As well, high concentrations of the attractant, or other signals, next serve to "localize" the cell, thus stopping its non-random walk. Signals which stop and/or regionalize cells in appropriate microenvironments are poorly understood.

The inventors also have shown, in the hematopoietic system, that complexes of cytokines and extracellular matrix molecules serve to localize progenitor cells (Long et al., 1992). Similar mobility (chemotactic) or localization signals exist for bone precursor cells, and mediate their movement into an osteogenic region (such as a fracture). Importantly, the inventors have devised a means to examine each of these phenomena. Quantitative assays for cell adhesion provides the minimal requirements for cell localization. Quantitative assays for assessing both chemotaxis and chemokinesis are also utilized.

Cell:Cell Interactions Required For Bone Precursor Cell Proliferation. The effects of aging on human bone precursor cells is evaluated by examining cell:cell and cell:ECM interactions at the various stages of development. The role of aging on the expression of known cell adhesion molecules is evaluated, particularly focusing on the β1 and β3 integrins. The Integrin Gene Superfamily members serve as receptors for both other cells and extracellular matrix proteins (Giancotti et al., 1990). Cell attachment to integrins is rapid (within minutes) and occurs as a result of increased avidity rather than increased expression (Lawrence et al., 1991). The ligand for most, but not all, integrins is the tripeptide sequence arginine-glycine-asparagine (RGD) (Ruoslahti et al., 1987).

Structurally, integrins are comprised of two membrane-spanning alpha and beta chains. The alpha-subunits contain three—four tandem repeats of a divalent ion binding motif and require magnesium or calcium to function. The alpha chains are (for the most part) distinct and bind with common or related β-subunits to yield functional receptors (Giancotti et al., 1990). The β chains seem to have functional significance and integrins can be subclassified based on the presence of a specific beta chain. Thus, family members containing β1 and β3 chains predominantly subserve cell:extracellular matrix interactions whereas molecules containing the β2-subunits primarily function in leukocyte:leukocyte interactions.

The studies thus focus on the role of β1 and β3 integrins in mediating the formation of human bone precursor cell colonies and preosteoblast proliferation. Two alternative approaches are used. First, antibodies to specific integrins (the VLA proteins 1–6, fibronectin receptor, type I collagen receptor and vitronectin receptor, as well as two non-integrin adhesion molecules ICAM 1 and 2) are used as probes for integrin expression on human bone precursor cells by flow cytometry.

Once the relevant molecules are identified, their role in both proliferation and differentiation formation will be evaluated in the inventors' bone cell assays. In these studies, human bone precursor cells assays (as above) are established and treated with antibodies (as well as isotype specific controls) to determine the role of these receptors in colony formation (i.e., cell:cell interactions at the osteoprogenitor cell to preosteoblast level), and in preosteoblast cultures (to examine their role in the proliferation and in the preosteoblast to osteoblast step). Alternatively, these cultures are treated with peptides containing the RGD sequence to inhibit integrin-mediated function. Control cultures are treated with equivalent sized peptides lacking the RGD motif.

Bone Precursor Cell:Extracellular Matrix Interactions. The inventors have demonstrated the importance of three: bone ECM proteins in human bone cell growth: osteonectin, osteocalcin, and type I collagen (Long et al., 1990 and Long et al., 1994). These and four additional matrix proteins are evaluated for changes occurring during aging: bone sialoprotein, osteopontin, fibronectin, and thrombospondin (Nomur et al., 1988 and Oldberg et al., 1986). Bone sialoprotein and osteopontin are likely to be involved in bone formation but their role in proliferation is unknown. The latter two proteins (thrombospondin and fibronectin) have been included due to their presence in bone extracellular matrix, and their demonstrated importance as cytoadhesion molecules in developing tissues (Weiss et al., 1980 and Clezardin et al., 1989).

In order to evaluate the actions of these ECM molecules on cell proliferation, soluble, purified bone ECM proteins are added to cytokine-driven bone precursor cell cultures. Varying amounts of exogenous ECM molecules are added in the presence of a single growth factor (e.g., 25 pM TGF-, or the optimal factor concentration defined as detailed above), to allow precise evaluation of the developmental effects of each extracellular matrix molecule. The combined effects of relevant cytokine and matrix molecules on the expansion of human bone precursor cells in vitro are determined.

Bone Precursor Cell Cytoadhesion and Tissue Localization A cytoadhesion assay which employs "caged" fluorochromes to label isolated progenitor cells for subsequent adhesion studies has been developed. In this assay, acetylmethylester derivatives of FITC are used to viably-label the cells. Upon internalization, intracellular esterases cleave the AM-ester derivative rendering the released fluorochrome relatively impermeable. Importantly, the fluorescence signal is linear with respect to cell number, and as few as several hundred cells can be detected. The cytoadhesion assay consists of the adhesion of caged-fluorochrome labeled cells to purified and/or recombinant proteins which are immobilized onto tissue culture plastic, as described previously (Long and Dixit, 1990 and Long et al., 1992), the removal of non-adherent cells, and quantitation in a fluorescent plate reader. The resultant sensitivity of this assay is approximately 100 times greater than other cytoadhesion assays reported (Long and Dixit, 1990; Long et al., 1992; Campbell et al., 1990).

The inventors utilized this assay in preliminary studies of purified human bone precursor cells (from young individuals) to evaluate attachment to extracellular matrix molecules. These data indicate that bone precursor cells express differential attachment capacities to both immobilized bone ECM molecules and immobilized cytokines. These observations are similar to previous work of the inventors' laboratory in which hematopoietic progenitor cells were demonstrated to bind to both growth factors and ECM molecules (Long and Dixit, 1990; Long et al., 1992; and Campbell et al., 1990).

Thus, as divergent cellular phenotypes, bone and hematopoietic cells both demonstrate dual requirements for matrix and cytokine molecules in the localization (adhesion) process. Notably, the binding of progenitor cells to immobilized, solitary cytokines further demonstrates that the presence of growth factors (which are often themselves immobilized within the extracellular matrix (Long, 1992)), is as least partially responsible for the lineage-specific localization of cells. Nonetheless, the presence of specific ECM molecules undoubtedly strengthens this localization process.

To perform these studies, cultures of proliferating bone precursor cells as well as osteoblast cells are established under optimal cytokine conditions (as above). The capacity of bone precursor cells to interact (adhere) with bone cell regulatory cytokines (bFGF, TGF-1, and BMP-2 and extracellular molecules (osteonectin, osteocalcin, bone sialoprotein, osteopontin, fibronectin and thrombospondin) are evaluated. These proteins are studied individually, and in combination, in order to determine their relative, or synergistic contribution to bone cell adhesion. These studies both corroborate and extend studies in which ECM cytokine molecules are exogenously added to the cultures to assess proliferative effects.

Bone Precursor Cell Chemotaxis. In a likewise fashion, the effects of aging on the motility machinery of developing bone precursor cells are evaluated. In these studies, various bone related growth factors are evaluated for their capacity to direct non-random movement (cytokinesis) and non-random migration (chemotaxis). As mentioned, early bone precursor cells possess the ability to actively migrate into the area of bone injury, there differentiating into bone-forming cells. However, no information exists on the factors or events which signal this important migratory process or how it may be altered during aging. A fluorescence-based assay which evaluates both chemokinesis and chemotaxis is available (Deforge et al., 1992).

In order to evaluate the effects of age on bone precursor cell migratory capabilities, a panel of known leukocyte chemotactic factors, osteogenic factors and ECM proteins in direct comparison of cells from the two age groups are utilized. Bone precursor cells from individuals of both age groups are evaluated for responsiveness to both known chemotactic factors (chemokines; i.e., interleukin-8, GM-CSF, M-CSF) and for the putative role of osteogenic growth factors in stimulating either chemokinesis or chemotaxis. In particular, bFGF and TGF-1, both powerful regulators of bone progenitor cell proliferation are evaluated as well as BMP2, PTH, and 1,25-OH vitamin D3. The chemokines are members of a chemotactic cytokine supergene family (Oppenheim et al., 1991).

The "chemokine-" cytokines are comprised of molecules with their first two cysteines interrupted by an amino acid (C-X-C), and are represented by such molecules as interleukin-8 (IL-8) and platelet factor 4 (PF4). MCP-1 and RANTES are representative of the "chemokine-" subfamily, and are characterized by an uninterrupted C—C arrangement. The use of IL-8 and MCP-1 allows employment of chemotactic factors which are known to induce migration of a broad spectrum of cells (Oppenheim et al., 1991).

The ECM proteins evaluated are described above. These studies determine (Urist et al., 1983) the appropriate cytokine and/or cytokine combination for bone precursor cell growth (Fishman et al., 1962), the role of cell:cell interactions, and (Hattersley et al., 1989) the relevant ECM molecules necessary for human bone precursor cell proliferation. The studies on integrin expression detail the mechanism of how human bone precursor cells interact with each other, the ECM, and how these interactions may be modified during aging. Studies of ECM molecules determine which are the relevant components involved in proliferation and/or migration, and whether responsiveness to any of these is lost with age.

Additionally, it is likely that excess concentrations of a given cytokine(s) or ECM protein will overcome an age-related deficit, thus demonstrating that the age defect is exogenous to the cell. These studies are designed such that a complex osteogenic microenvironment is reduced to a stepwise evaluation of each of its relevant components. These studies define both the minimum essential conditions for the proliferation of human bone precursor cells and demonstrate age-related changes.

EXAMPLE 4

Age-Related Alterations in Bone Protein Expression by Purified Populations of Human Bone Precursor Cells The present example concerns the further immunological purification and characterization of bone-antigen positive human trabecular bone precursor cells, and the demonstration that distinct, age-related changes in the cellular expression of osteonectin and osteocalcin occurs in these cell types.

Materials and Methods

Bone Marrow Cell Preparation and Culture. Human bone marrow aspirates were obtained from normal volunteers following informed consent. It should be noted that samples from young individuals ($\leq 18$ years) came from the discarded portions of bone marrow obtained on the Pediatrics Hematology/Oncology Service for the purposes of allogenic bone marrow transplantation, for which informed consent was granted by the parent(s). Bone Marrow samples from individuals $\geq 18$ years of age were obtained following informed consent by routine bone marrow aspiration.

As an alternative, marrow from older individuals was also obtained from rib fragments discarded in the course of thoracic surgery (to date, the inventors have detected no site-dependent differences in flow-cytometry parameters of human bone precursor cells).

Bone marrow non-adherent low density (NALD) cells were prepared by adherent cell depletion, and density separation techniques as described by Long et al. (1988) and in Example 1. NALD cells are then subjected to immune-adherence isolation, or immuno-magnetic purification.

Antibodies, Immune-Adherence, and Induction of Differentiation. The expression of bone protein antigens was determined by fluorescence activated flow cytometry using monoclonal antibodies to human osteonectin, alkaline phosphatase, or osteocalcin, as described in Example 1.

Immune-adherence isolation of human trabecular bone precursor cells and their induction into osteoblast differentiation was performed as described in Example 1.

The induction of osteoblast differentiation was performed as described in Example 1 using 25 pM TGF-β.

Immunomagnetic Purification of Human Bone Precursor Cells. Purification of human bone precursor cells was performed using immunomagnetic separation. This was carried out via Magnetic Activated Cell Sorting (MACS; Miltenyi Biotec, Sunnyvale, Calif.) as per manufacturer's instructions, but modified as noted below.

For MACS separation, the NALD cells are washed once, and simultaneously labeled with FITC-conjugated monoclonal anti-osteocalcin and biotinylated anti-osteonectin (both as above), both at 10 µg/mL, in Tris-Buffered Saline containing 1% BSA, pH 7.6 The antibody-labeled cells are then washed twice, and labeled with goat anti-mouse IgG (heavy and light chain specific; Miltenyi), conjugated to superparamagnetic nanobeads. The antibody is incubated at 180 µL per $10^8$ NALD cells per 1.0 mL for 30 min, at 4° C.

The anti-IgG labeling is performed in column-loading buffer (0.5% BSA, 0.1% glucose in PBS), modified to contain 0.5 µg/mL aprotinin, 0.5 µg/mL leupeptin, and 5 µg/mL soybean trypsin inhibitor, and 500 U/mL of DNase (Sigma). The protease inhibitors were added following preliminary studies which demonstrated a progressive loss of antigens with increasing separation time; the DNase was added to eliminate cell clumping (Long et al., 1988).

From $100-300 \times 10^6$ cells are loaded onto a Miltenyi magnetic column equipped with a 26 g flow-restrictor (Miltenyi) at $1 \times 10^8$ cells/mL in 1.0 mL increments, running 0.5 mLs of loading buffer after each increment. Antigenically negative cells are eluted with 1.0 mL of elution buffer (loading buffer with DNase and protease inhibitors increased by a factor of 4). Following elution antigen-positive cells are recovered by removing the magnet, and eluting with 1.0 mL of elution buffer. These antigen-positive cells are then re-isolated on a second magnetic column using the same procedure.

Flow Cytometric Analysis. Flow cytometric analysis was performed as described in Example 1 using a Becton-Dickinson (San Jose, Calif.). FACSCAN system and data analyzed with the BD LySys software program. Controls consisted of autofluorescence as well as non-specific fluorescence detected with isotype-specific murine monoclonal antibody to keyhole lymphet hemocyanin (KLH) obtained from Becton Dickinson.

For two-antigen (two-color) analysis, the magnetically isolated cells are then incubated for 15 min at 4° C. with strep-avidin conjugated to PerCP (Becton Dickinson) in order to visualize the osteonectin antigenic determinant. Immunomagnetically purified cells were analyzed for fluorescence intensity versus size (forward-angle scatter), as well as intracellular complexity (side-scatter).

In order to map the cellular characteristics of preosteoblast and osteoblast cells in immune-isolated populations the two-color fluorescence profiles were back-gated (Given, 1992) to determine their size and side-scatter profiles.

Results

Osteoblastic Differentiation of Preosteoblasts. The inventors previously demonstrated that immune adhesion mediated by antibodies to human bone matrix proteins results in the isolation of population of human bone precursor cells which are responsive to osteogenic cytokines, but lack responsiveness to hematopoietic growth factors (Example 1).

In order to further characterize bone precursor cells, the inventors isolated human bone precursor cells by immune adherence and subjected the resultant cell population to multiparameter flow cytometry to characterize the cellular differences between isolated pre-osteoblasts and osteoblasts.

Figure 5A:
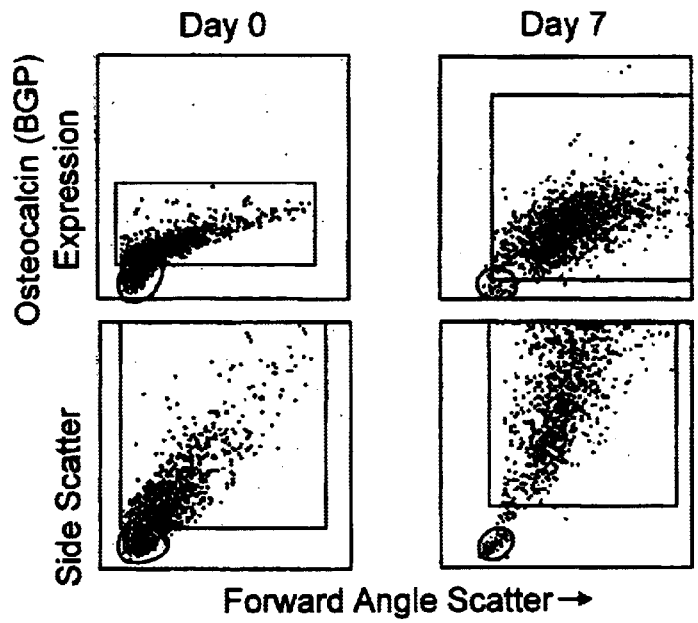
FIG. 5A in four sub-panels shows forward angle and side-scatter characteristics of un-induced and TGF-β-induced human bone precursor cells isolated by immune-adherence. Upper sub-panels, day 0 (un-induced) immune adherent cells and differentiated cells following 7 days of TGF-β stimulation (left and right sub-panels, respectively). Horizontal dashed lines represent upper limit of non-specific (inappropriate antibody) fluorescence, vertical lines represent the upper 95% size limit for input NALD cells, both as defined herein and in Long et al. (1995). Lower sub-panels, back-gating of antigenically marked cells to display their forward and side scatter characteristics.
Figure 5B:
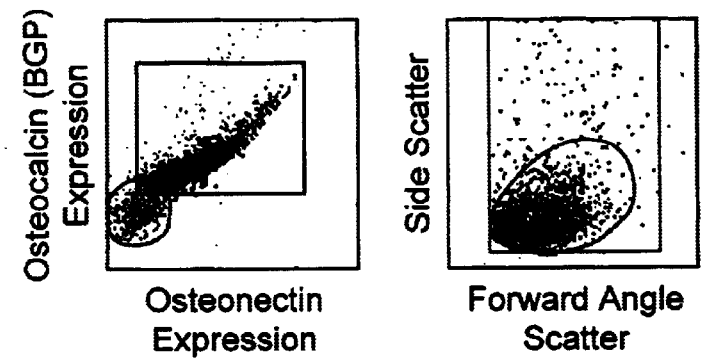
FIG. 5B in two panels shows forward and side-scatter characteristics of immunomagnetically purified human bone precursor cells. Immunomagnetically separated cells were subjected to two color analysis of osteonectin and osteocalcin expression and back-gated. Dashed lines represent upper limit of non-specific (inappropriate antibody) fluorescence as described above, and determined by single-color analysis of each fluorescent signal, both as defined herein and in Long et al. (1995).
Figure 5C:
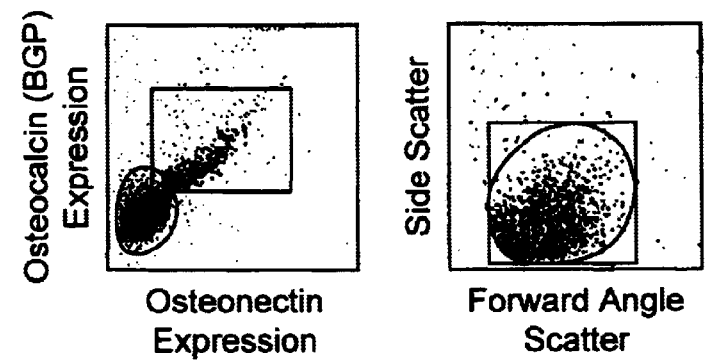
FIG. 5C in two panels shows bone protein expression and phenotypic analysis of human bone precursor cells from a subpopulation of elderly individuals. Among the 17 individuals age $\geq 60$ yrs. old, three females (aged 60, 88, and 89 yrs old) and one male showed a distinctly different preosteoblasts antigenic profile. These individuals show a predominant population of cells that are antigenically dull (left panel). However, back gating of these cells demonstrates that they have similar forward and side-scatter characteristics to human bone precursor cells from their age-matched cohort, but lack high numbers of $ON^{++}$ and $OC^{++}$ bright cells. A single individual (age 89) from the group is shown.

Confirming and extending the previous data, immune-adhesion yielded a population of bone antigen-positive cells, that predominantly are the size of a lymphocyte which, when stimulated with TGF-β, show a marked increase in antigen density and cell size (FIG. 5A, FIG. 5B and FIG. 5C). Notably, there are two size (as indicated by the parameter "Forward angle scatter" in FIG. 5) populations among immune adherent cells, and TGF-β-induced differentiation results in a shift between the small and large cell compartment (FIG. 5A, upper left and right panels).

In order to further examine the developmental characteristics of these cells, isolated uninduced and induced cells were electronically divided into small and large cell compartments and "back-gated" to determine the side-scatter characteristics of each (FIG. 5A, lower left and right subpanels).

These data show that the larger osteoblast cells (i.e., those falling within the outlined square in figures) also have the highest degree of intracellular organization (side-scatter characteristics). This was seen in both uninduced cells (in which osteoblast-sized cells represent approximately 5% of the isolate) and induced cells (FIG. 5, left and right subpanels, respectively). Thus, the TGF-β-induced differentiation of human bone precursor cells results in an increase in antigenic content, cell size, and an increase in intracellular complexity. This is true for both osteocalcin (BGP)-positive cells, as demonstrated in FIG. 5A, FIG. 5B and FIG. 5C, and alkaline-phosphatase-positive cells.

Isolated cells also contain a population of cells (circled in FIG. 5A) in which antigen density is little different from non-specific antibody controls. Back-gating of this population consistently shows these cells as having a low degree of side-scatter. These characteristics (i.e., low side-scatter and small size) are consistent with a residual population of lymphoid-like cell which do not bear detectable bone antigens.

Immunomagnetic Purification of Human Bone Precursor Cells. Immune-adherent isolation of human bone precursor cells is based on the co-immobilization of monoclonal antibodies to both osteonectin and osteocalcin (Example 1). This procedure results in a purified population of bone precursor cells which express osteocalcin, osteonectin, and alkaline phosphatase. However, the procedure does not allow for distinguishing between individual subpopulations of cells expressing these antigens, or a single population of cells which co-express osteonectin, alkaline phosphatase, and osteocalcin on the same cell.

In order to examine this, the inventors undertook further purification of these cells utilizing magnetic-activated cell sorting. The isolation of these cells thus uses physical separation (equilibrium density centrifugation), plastic-adhesion (to remove bone marrow stromal cells), and immunomagnetic separation.

Figure 6B:
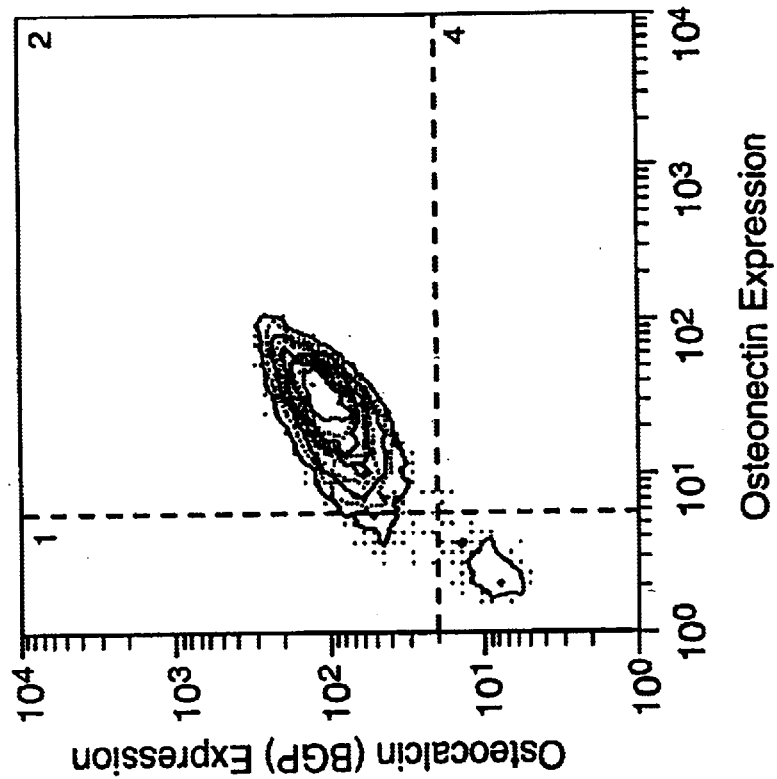
FIG. 6B shows that the immunomagnetic separation results in an essentially antigenically pure cell population that co-express osteonectin and osteocalcin.
Figure 6A:
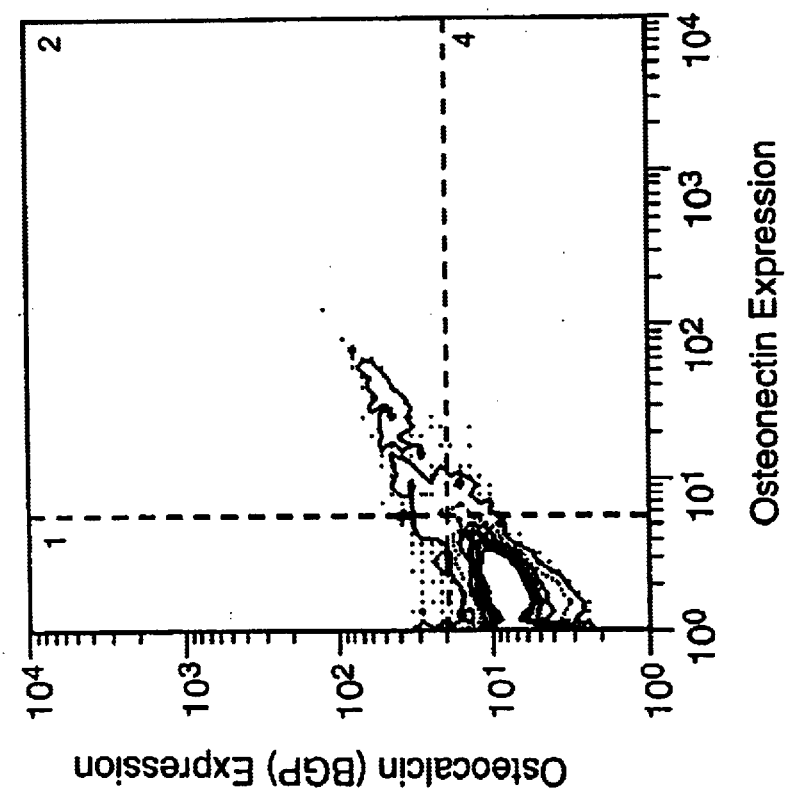
FIG. 6A shows that the first two physical separation steps results in a moderate enrichment of bone-antigen-positive cells.

Interestingly, physico-chemical separation (density) results in a moderate enrichment of these cells to a level of 6–7% purity (FIG. 6A; Table 1). In contrast, immuno-magnetic separation based on the osteocalcin and osteonectin antibodies antigens yields a 95% pure population of cells (FIG. 6B) which represents an approximate 4,800-fold purification over unfractionated bone marrow (Table 1).

TABLE 1

Purification of Human Bone Precursor Cells by Combined Physico-Chemical and Immunological Procedures.

| Procedure | HBPC Frequency | HBPC fold - Purification |
| --- | --- | --- |
| Unfractionated BM[a] | 0.0002 | N. A. |
| Post-EDC and plastic-adherence (NALD) | 0.06 | 300 |
| Post-Immune-[b] adherence separation | 0.60 | 3000 |
| Post-Immuno-magnetic separation | 0.95 | 4750 |

Frequency is number of osteocalcin-positive as determined by flow cytometry.

[a] Unfractionated bone marrow is frequency of osteocalcin-positive cells in un-separated bone marrow in which RBCs are removed by velocity sedimentation and the resultant WBC subjected to flow cytometry and back-gating as in text.

[b] Immune adherence and immunomagnetic separation purification are not sequential steps. Rather, these two rows show the relative fold-purification of each technique.

BM=bone marrow, EDC=equilibrium density centrifugation, HBPC=human bone precursor cells, NA=not applicable, NALD=Non-adherent low density. A typical separation procedure is presented.

Figure 8:
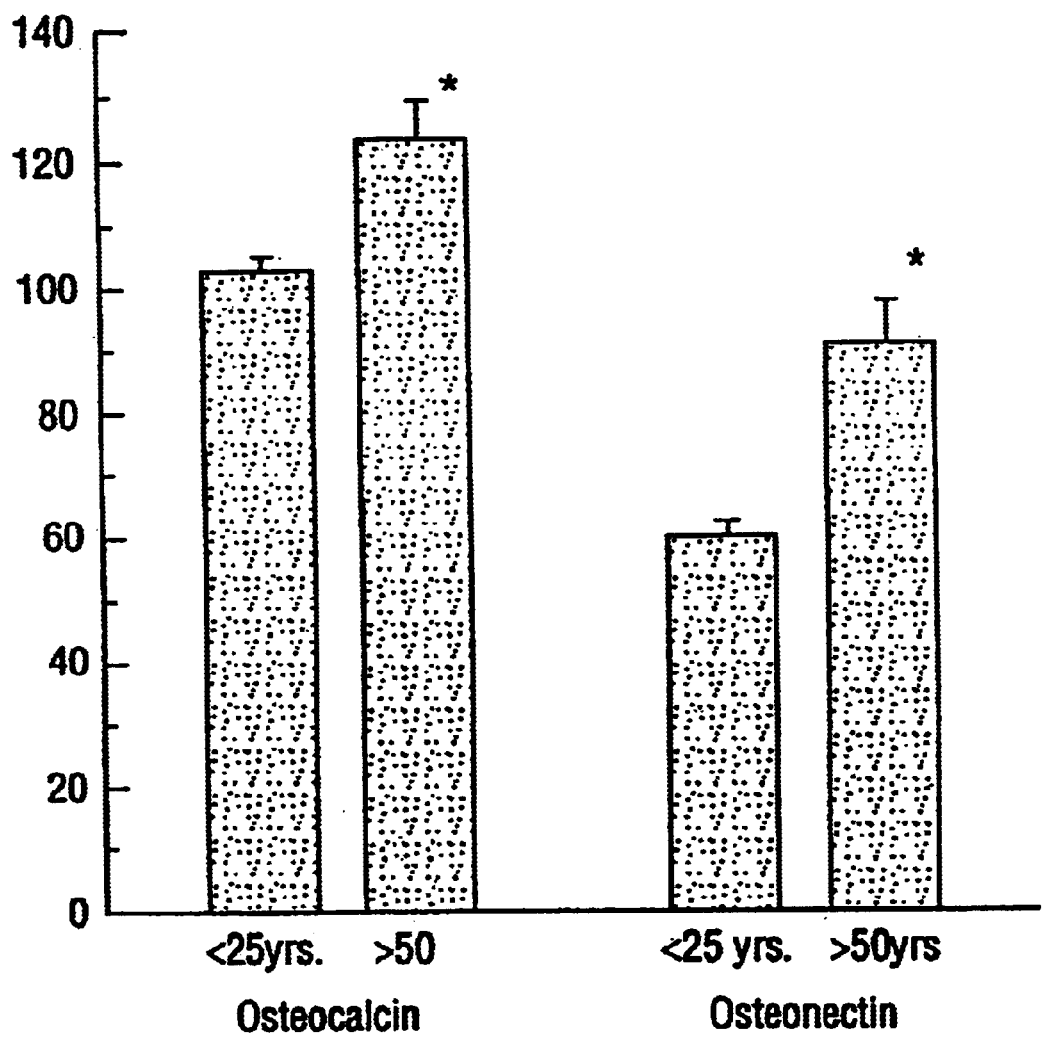
FIG. 8 in a single panel shows age-related alterations in mean specific fluorescence of osteonectin and osteocalcin. Single color antigenic profiles of purified human bone precursor cells populations were used to determine mean specific fluorescence. *=p≦0.05, Student's t-test, two-tailed.

Immunomagnetically separated cells were subjected to two-color fluorescence-activated cytometry to examine the expression of osteonectin and osteocalcin. These data show that the isolated cells co-express both proteins (FIG. 8B). Moreover, antigen-density contour plots demonstrate that these antigens are co-expressed in a single population of cells, in that no distinct sub-populations of single-antigen positive cells are detected.

There remains, however, a small population of antigen-dull cells (quadrant 3 in FIG. 6B). However, unlike the antigenically null-population seen in cells separated by immune-adherence, the magnetically separated antigen-low or dull cells have the same side-scatter characteristics as the double-positive cell population (compare FIG. 5B, circled population right and left). Given that these cells are recovered following two passes through the magnetic isolation column, it is unlikely that these are contaminating lymphoid cells (as are seen in immune adherence-based separation). Rather, they represent cells with a sufficient (albeit low) antigen density (albeit a low density) to retain them on the column in the presence of a magnetic field.

Increasing Donor Age is Associated with Alterations in Bone Protein Expression of Human Bone Precursor Cells. A series of flow cytometric investigations on immunomagnetically-separated bone precursor cells demonstrate that age-related changes in bone protein expression occur with increasing age. These studies were performed on a total of 41 individuals of three age groups: ≦25 years old (mean age 16.4±7 (S.D.) years, range 1.5–24 years, n=15), 50 years old; (mean age 36.6±5 years old, range 26–45 years, n=9) and individuals ≧50 years old (mean age 70.1±12 years, range 53–89 years, n=17).

Human bone precursor cells were isolated and purified cells from individuals in the given age groups and subjected to multi-parameter flow cytometric analysis. Confirming the above observations, antigenically-purified human bone precursor cells from these three age populations co-express both osteonectin and osteocalcin.

Figure 7A:
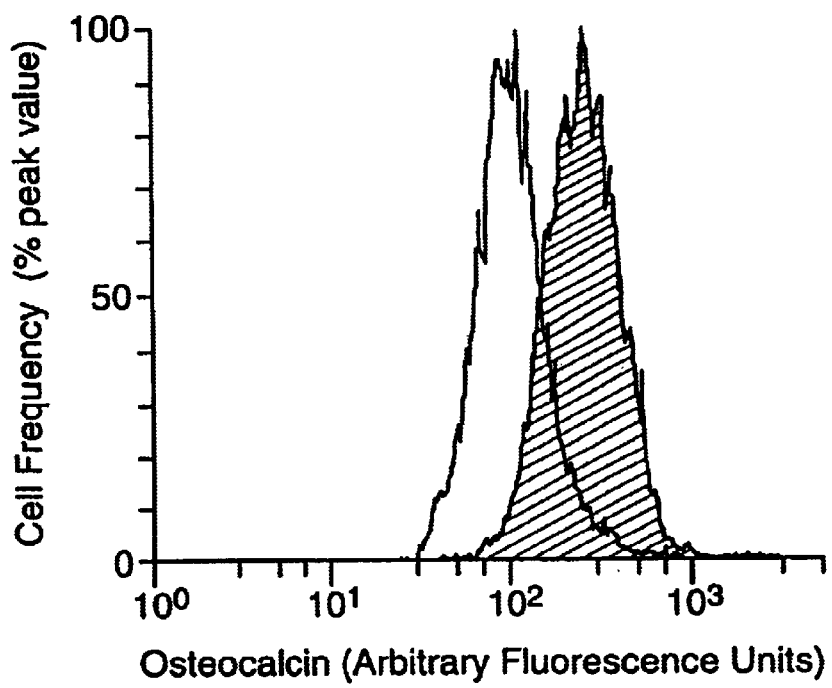
FIG. 7A shows purified human bone precursor cells evaluated for osteocalcin.
Figure 7B:
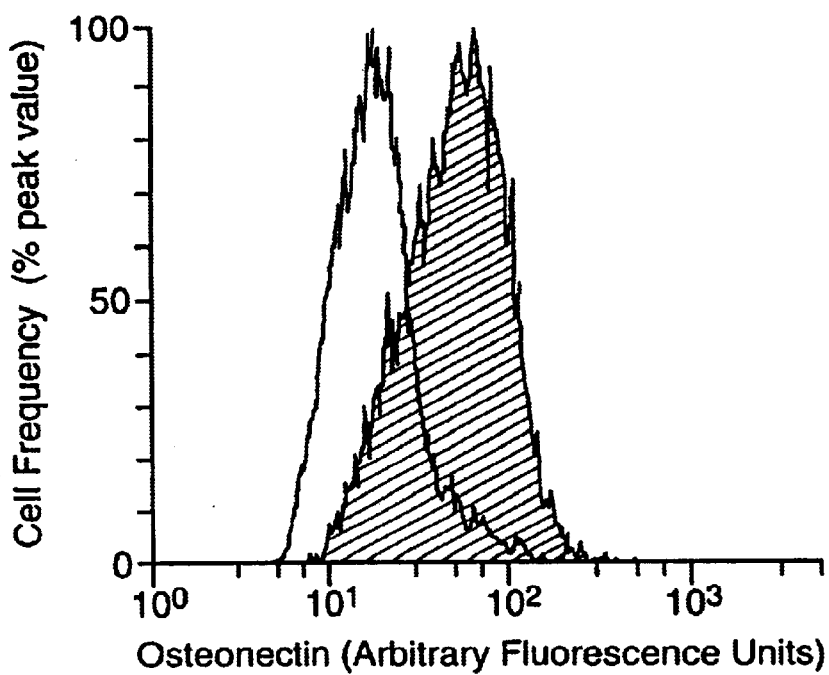

Interestingly, osteonectin and osteocalcin antigenic expression by human preosteoblast cells increases with increasing age. In order to visualize these shifts in antigen density, cytometric profiles from two representative individuals (one old-aged 60, one young-aged 9) were overlaid (FIG. 7A and FIG. 7B). These profiles were defined as representative because their mean-fluorescence and peak-fluorescence values were identical to the averages determined for their respective age-cohorts, and their coefficiencies of variation were similar.

FIG. 7A and FIG. 7B clearly illustrates that the human bone precursor cells in older individuals (i.e., $\geq 50$ years of age) express higher amounts of these two bone proteins than do younger individuals (i.e., $\leq 25$ years old). Profiles from middle aged individuals were intermediate to the other two age groups.

In order to determine whether these alterations were statistically significant for the whole population, the mean specific- and peak-fluorescence were determined for each individual in each age group. A significant ($p \leq 0.05$) age-related increase was noted in both the mean specific fluorescence for osteocalcin and osteonectin (FIG. 8), as well as in the peak fluorescence of each antigen.

Osteocalcin shows a moderate but significant change in mean fluorescence, increasing by 21 arbitrary log units. In contrast, osteonectin expression increases to a greater degree in the population of older individuals (an increase from 59 to 89 arbitrary log units; FIG. 10).

Figure 9:
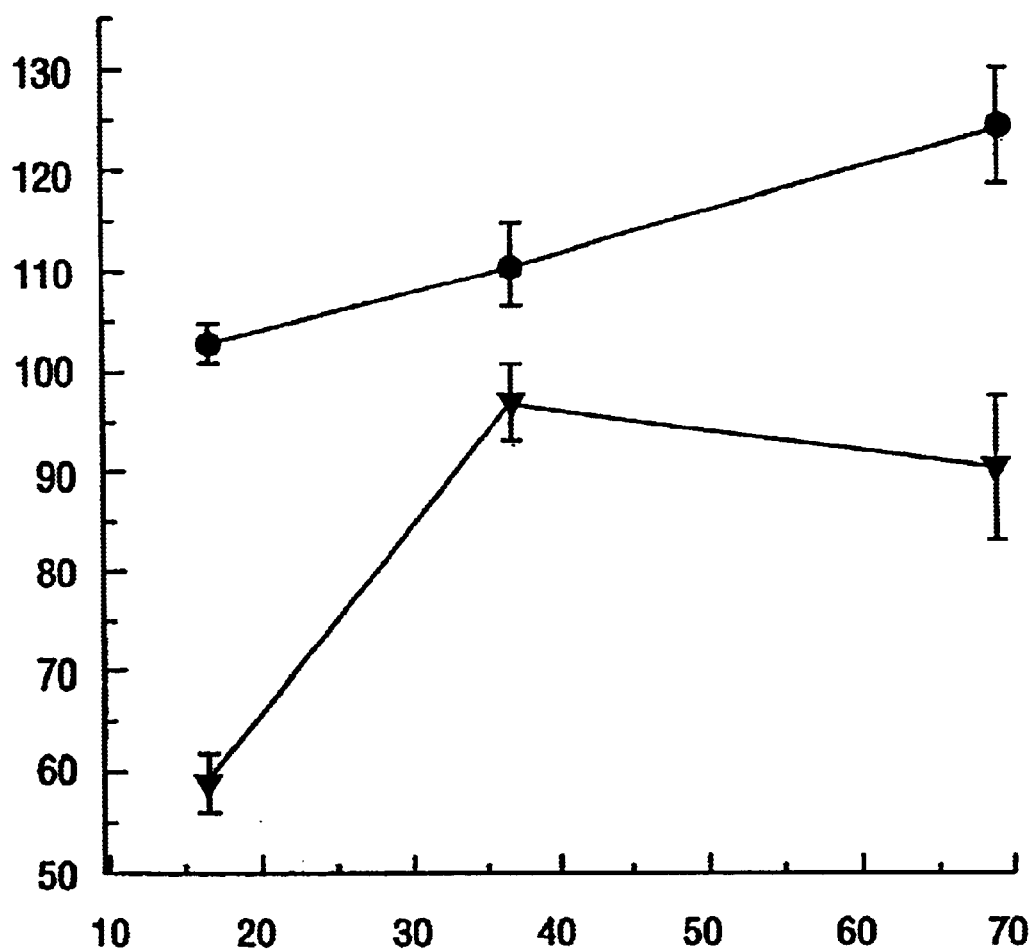
FIG. 9 in a single panel shows age-related changes in bone protein expression. The mean specific fluorescence was plotted against the mean age for each group young (≦25 years old, mean age 16.4±7 (S.D.) years, range 1.5–24 years, n=15; middle age individuals (mean age 36.6±5 years old, range 26–45 years old, n=9), and elderly (≧50 years old, mean age 68.8±7 years, range 53–89 years, n=13). Circles, Osteocalcin (BGP); Inverted triangles, Osteonectin.

The inventors further analyzed this unexpected increase in bone protein levels by examining the relationship between age and antigenic expression (FIG. 9). Note that, in this data, the numbers of individuals of middle age are lower than the other two age-cohorts. Nonetheless, it appears that the majority of the increase in human bone precursor cell osteonectin and osteocalcin levels occurs between the ages of 15–16 and 35–40.

Of the seventeen individuals greater than 60 years of age evaluated, four (three women, age 64, 88; and 89 years old; one male age 59) did not show the human bone precursor cell immunophenotypic characteristics described above (FIG. 5C). Rather, the majority (80–90%) of the presumed preosteoblasts isolated from these individuals are similar in antigenic content to the antigen-dull population of cells described in FIG. 5B (left hand panel, circled population).

These individuals thus lack the predominant osteocalcin-positive/osteonectin-positive ($OC^{++}/ON^{++}$) bright population observed in all other individuals (n=37), including their age-related cohort (both male and female). Given the immunomagnetic retention of these cells on the column, and that the forward-angle and side-scatter characteristics of these cells are identical to that of the antigen-dull cell subpopulation, the inventors conclude that these individuals possess a population of preosteoblasts which differ greatly in their antigenic expression.

Consistent with this, the mean and peak fluorescence of both osteonectin and osteocalcin are significantly reduced, even when compared to the youngest age-cohort (Table 2). These data suggest that a separate subpopulation of individuals exists with distinctly different (lower) human bone precursor cell antigenic content.

The physiological and clinical significance of such alterations may be that the immunophenotype of these two populations of elderly individuals reflects the status of their bone cell function. In their fifties or sixties, most individuals (male and female) show varying degrees of osteoporosis. Thus, the identification of alterations in bone protein expression undoubtedly demonstrates the basis for known elevations in these proteins (osteocalcin (BGP) and osteonectin) in the plasma of elderly individuals. The identification of a subpopulation of elderly individuals might thus demonstrate a group of individuals with more severe disease.

TABLE 2

Comparison of Bone Protein Expression Among Elderly Individuals

|  | Osteocalcin (BGP) | | Osteonectin | |
| --- | --- | --- | --- | --- |
| Age (yrs.) | Peak Fl. | Mean FL. | Peak FL. | Mean Fl. |
| 59 | 70 | 63 | 17 | 25 |
| 64 | 54 | 52 | 33 | 40 |
| 88 | 59 | 59 | 43 | 36 |
| 89 | 63 | 65 | 36 | 31 |
| Mean: 75 ± 8 | 62 ± 3* | 60 ± 3* | 30 ± 4* | 33 ± 3* |
| Cohort Mean: 69 ± 3 | 122 ± 7 | 123 ± 6 | 91 ± 8 | 89 ± 7 |

EXAMPLE 5

Preparation of Bone Precursor Cells from Peripheral Blood

The present example concerns the further preparation of bone precursor cells from peripheral blood.

The inventors found that animal bone precursor cells circulate, thus making it possible to recover and purify these cells in animal peripheral blood.

Human bone precursor cells were isolated from human peripheral blood by venipuncture. Blood was drawn into preservative-free heparin, to prevent coagulation, and processed for human bone precursor cells using the same protocol as described above for bone marrow isolation:via immunomagnetic separation. Briefly, this entails equilibrium density centrifugation (ficoll), and plastic-adherence to generate NALD cells, their labeling with monoclonal antibodies to osteocalcin (BGP) and osteonectin, and processing for immunomagnetic separation and purification. The resultant cells were analyzed by multi-parameter flow cytometry as described above.

The human bone precursor cells isolated from peripheral blood were found to have similar flow cytometry characteristics to those of bone marrow.

EXAMPLE 6

The Effect of Aging on the Ability of Bone Precursor Cells to Differentiate Into Osteoblast Cells and the Capacity of Such Osteoblasts to Elaborate an Osteoid Extracellular Matrix The complete evaluation of bone cell development requires the study of both bone precursor cells (osteoprogenitor cells and preosteoblasts) as well as their differentiated progeny, the osteoblasts. It is the osteoblasts that are responsible for the elaboration and mineralization of bone matrix, and the subsequent formation of bone. As mentioned previously, published morphological and morphometric reports suggest that a differentiation blockade may occur during the aging process resulting in reduced osteoblast numbers (Roholl et al., 1994 and Nimni et al., 1993). However, other evidence exists suggesting that the osteoblasts in older individuals have diminished function in that they show decreased responsiveness to mitogenic stimuli (Pfeilschifter et al., 1993 and Wong et al., 1992), and produce decreased amounts of bone matrix proteins, (Liang et al., 1992) and osteoid (Nimni et al., 1993).

It is important to evaluate the capacity of preosteoblasts to differentiate into osteoblasts, and the capacity of those osteoblasts to function normally. Importantly, such studies cannot be performed on human trabecular bone outgrowth cultures for a variety of reasons (limiting cell numbers, lack of purified cells, heterogeneity of cell types present, etc.), and because the principle age-related defect may be a failure earlier in the osteoblast differentiation pathway. That is, cell development may not progress from osteoprogenitor cell to preosteoblast, or from preosteoblast to osteoblast. Therefore, it is best to examine this problem in a system in which the full spectrum of human bone cell proliferation/differentiation can be evaluated.

Regulation of Osteoblast Cell Differentiation. As described above, the inventors have developed a system in which isolated and purified bone precursor cells proliferate and differentiate into osteoblasts. In particular, the inventors have demonstrated that the process of switching serum-free cultures to TGF-β driven, serum-containing cultures results in a differentiation of preosteoblasts into osteoblast cells (Long et al., 1990).

Importantly, the osteoblasts generate an osteoid extracellular matrix in which non-collagenous bone proteins are deposited and the cells calcify the extracellular matrix (Long et al., 1990). The effect of aging on both the differentiation of preosteoblasts into osteoblasts, and the subsequent alterations in differentiated cell (osteoblast) function is being investigated. As such, the cell culture protocol described herein is modified to induce osteoblast cell differentiation.

In these studies, bone precursor cell cultures are run in two phases. The first phase (7–10 days) is a proliferation step utilizing serum-free cultures containing either TGF-β or, if better, a growth factor/matrix combination for generation of maximum numbers of bone precursor cells. During this phase of the cultures, only cellularity and antigen expression is monitored as an index of culture conditions. At optimal cell density, these cultures are switched to serum-containing, TGF-β-containing conditions.

Subsequent studies (over an additional 7–10 days) evaluates osteoblast differentiation patterns and functional capacities. As described herein, the inventors have defined a multi-parameter flow cytometric analysis of osteoblast cell differentiation markers; these cells increase in cell size, cell complexity, and the expression of multiple markers of bone cell differentiation. The capacity of pre-osteoblasts to differentiate into osteoblast cells using this multi-parameter flow cytometric analysis is determined.

In particular, the expression of the bone proteins, osteocalcin and osteonectin, plus two additional biochemical markers of bone differentiation, alkaline phosphatase and type I collagen is determined. As mentioned, alkaline phosphatase are monitored by both flow cytometry, as well as by alkaline phosphatase (EC 3.1.3.1) cytochemistry (Reddi, 1981). This latter procedure distinguishes bone alkaline phosphatase from that of liver based on heat and urea sensitivity. As a corroborative study, the production and deposition of bone extracellular matrix molecules by osteoblast cells from both age groups is determined by metabolic labeling and immunoprecipitation using $^{35}$S-methionine immunoprecipitation.

Extracellular Matrix Calcification. Studies on the capacity of osteoblast cells to mineralize their surrounding (bone) ECM employ two alternative approaches: metabolic labeling with $^{45}$Ca$^{++}$, and histochemical analysis utilizing the von Kossa staining procedure. For the calcium labeling studies, two aspects of bone cell calcium metabolism are evaluated: their ability to take up calcium and their ability to deposit calcium into the extracellular matrix.

As previously demonstrated, osteoblast cells are removed from culture and equilibrium-labeled (one hour) with $^{45}$Ca$^{++}$ (Long et al., 1990 and Long et al., 1993). Briefly, osteoblasts cultured for 3, 5, 7, 14 and 21 days post serum-, or serum-free growth factor stimulation are removed and washed 3 times with calcium-free PBS, and metabolically labeled with 50 Ci $^{45}$Ca$^{++}$ for 60 min at 37° C. Following $^{45}$Ca$^{++}$ calcium-equilibration, labeled cells are washed free of unincorporated calcium, resuspended in serum-free tissue culture medium and re-established in the original culture dishes. An aliquot of Ca$^{++}$-labeled cells are analyzed immediately for $^{45}$Ca$^{++}$ content. Quantification of the amount of $^{45}$Ca$^{++}$ taken up per cell indicate age-induced differences in calcium uptake, whereas matrix calcium content indicates changes in deposition.

For matrix deposition, equilibrium-labeled cells are allowed to incorporate cellular $^{45}$Ca$^{++}$ into ECM. Given that both osteocalcin (BGP) and osteonectin bind calcium, this exogenous cell-labeling procedure precludes fluid-phase $^{45}$Ca$^{++}$ binding to previously synthesized matrix proteins. Subsequently, cells/ECM are removed with (brief) trypsin/EDTA, cells pelleted by centrifugation, and $^{45}$Ca$^{++}$ incorporation into the trypsin/EDTA extractable ECM determined by scintillation counting. Trypsin-resistant ECM is then removed by Triton X-100 extraction as described previously (Gospodarowicz and Ill, 1980; Long et al., 1990) and counted similarly. To control for residual cell contamination, ECM extracts are monitored for DNA content and calcium deposition into the matrix calculated as a total extractable $^{45}$Ca$^{++}$ corrected for that due to contaminating cells.

The above calcium loading studies evaluates precisely the uptake and deposition of calcium by human osteoblast cells during their differentiation. The histochemical identification of matrix calcium deposition utilizing the von Kossa staining reaction (Long et al., 1990; Heeley et al., 1973; and Puchtler et al., 1978) is evaluated. The inventors previously correlated the presence of positive von Kossa reactions with the ability of osteoblast cells generated from (unfractionated) precursor cells to metabolically deposit calcium in the extracellular matrix (Long and Dixit, 1990). These cultures are examined for von Kossa reactivity at the same time points of the calcium incorporation/deposition studies. Thus these kinetic studies are correlated with each other, and demonstrates the validity of the von Kossa reaction as an indicator of the early phases of calcification for primary human cells.

Chondrogenic Potential Of Bone Cultures. Bone precursor cells are tested for their functional capacity to undergo chondrogenic differentiation. These studies address an alternative concept that the age-related differentiation blockade may favor chondrogenesis rather than osteogenesis. This is particularly important if the osteoprogenitor cells have chondrogenic potential, a concept often discussed but never definitively proven. However, some suggestion of this exists in a study of rat osteoprogenitor cells (Taniguchi et al., 1993). In this study, peri-osteal injection of TGF-β stimulated neonatal osteoprogenitor cells, whereas in adults it induced differentiation of chondrocytes. The incorporation of $^{35}SO_4$ into proteoglycans as well as immunocytochemistry of chondrocytes (as detailed in the Preliminary Results) is used to study chondrogenesis.

Reddi and co-workers have shown that $^{35}SO_4$ is incorporated into proteoglycans during the cartilaginous phase of bone matrix-induced chondrogenesis (Reddi, 1981). Bone cell cultures from both age groups are metabolically labeled with $^{35}SO_4$, and the incorporation of label into proteoglycan monitored by detection of chondroitinase ABC (EC 4.2.2.4)—sensitive radiolabel incorporation. For studies of $^{35}SO_4$ incorporation, osteoblast cells are differentiated as above, and metabolically labeled (6–12 hrs) with $^{35}SO_4$. Subsequently, the cells are released and ECM is treated with chondroitinase ABC and enzymatically-liberated label monitored by scintillation counting.

Bone protein synthesis, alkaline phosphatase expression, $^{35}SO_4$ incorporation (low), and $^{45}Ca^{++}$ deposition all strongly indicate the presence of bone-forming cells. However, they do not distinguish definitively between chondroblasts and osteoblasts. For example, most if not all cells contain surface proteoglycans, and contaminating cells thus may be sensitive to chondroitinase release of $^{35}SO_4$. Further, the demonstration of cellular $Ca^{++}$ deposition while clearly showing the osteogenic organization of the matrix, does not demonstrate the presence of hydroxyapatite.

A better indicator of cartilage/bone differences is the pattern of collagen deposition during bone formation (bone produces type I, and cartilage type II collagen). These studies employ collagen peptide mapping (via CNBr cleavage) (Barsh et al., 1980). In this procedure, collagen synthesis is monitored by metabolic labeling using $^3H$-proline (100 Ci/ml; L2,3,4,5 3H proline, Amersham, spec. act 120 Ci/mM). Cells are pre-incubated in the presence of 50 g/ml Na-ascorbate, washed and metabolically labeled for 16–24 hours. Subsequently, the cells are disrupted, lysate dialysed against 1 mM $NH_4CO_3$, and digested with 100 g pepsin in 0.5 M HAc, and subjected to cleavage within the PAGE polyacrylamide gels (Barsh et al., 1980).

Several outcomes of the above studies are envisioned. One is that age-related changes might affect bone matrix or bone protein production directly. Conversely, the lack of "normal" bone-ECM or bone protein production by preosteoblasts may actually be due to the "down-regulated" expression of important bone cell markers required as an antecedent to bone ECM mineralization. The studies described in herein distinguish between defects at the level of preosteoblast to osteoblast differentiation, and those alterations occurring in osteoblast function.

The inventors can evaluate human bone precursor cell development in multiple age groups (e.g., 18–25, 26–49 and >50) from the level of the osteoprogenitor cells to the stage of osteoblast cells depositing and calcifying osteoid ECM. Thus, important information is obtained concerning the role of age-induced changes on bone cell differentiation and function, particularly as it relates to calcium metabolism. These data provide a more complete understanding of the events regulating bone cell development in both older and younger individuals.

EXAMPLE 7

Osteogenic Genes Which are Differentially Modified During Aging

The above examples are designed to determine the nature and degree of the alterations induced by the aging process of human bone precursor cells and their progeny, the osteoblasts. They do not, however, examine the molecular basis of age-induced changes in cellular development. The genetic alterations occurring in these cells with aging are determined in this example. The proliferation and differentiation protocols discussed are used to evaluate the molecular control of those proteins specifically altered. Those genes which are uniquely altered in expression during aging are identified.

Analysis Of Bone Protein Messenger RNA. The effects of age on the regulation of bone protein mRNA (for both degree of expression, and temporal expression) is analyzed by both Northern analysis and in situ hybridization. Osteonectin, osteocalcin, alkaline phosphatase, and osteopontin mRNAs are used as probes for the matrix molecules. Northern analysis (or the more sensitive Si nuclease assay) is performed as described previously by one of the inventors (Long, et al., 1990).

As an alternative, bone precursor cells or progenitor cell-colonies from both age groups can be fixed and message expression evaluated by in situ hybridization. This latter procedure is carried out utilizing biotinylated cDNA probes. Non-isotopic in situ hybridization is performed as described by Singer et al. (Singer et al., 1986). This procedure yields signal and noise ratios equivalent to autoradiography while allowing excellent morphological identification (Lawrence et al., 1986). The cDNA probes are prepared utilizing random primer incorporation of biotinylated ATP (BRL, Gaithersburg, Md.) or other biotinylated dNTPs (Photobiotin Labeling, BRL).

Briefly, paraformaldehyde fixed cells are incubated in 1% Levisamole to inhibit endogenous alkaline phosphatase (Schmetzer et al., 1987), and hybridized for 4 hours at 37° C. Following hybridization to cellular RNA, the biotinylated probe is conjugated to streptavidin, the streptavidin linked to biotin-conjugated alkaline phosphatase, and reacted with bromochloroindolyl phosphate and nibroblue tetrazolium to yield a blue precipitate at the site of cDNA hybridization. These studies determine the temporal expression of know bone protein mRNAs in osteoprogenitor cells (with RT-PCR and in situ hybridization), preosteoblasts, and osteoblast cells (both with Northern or S1s). For osteoprogenitor cell colonies, these are picked at various times during colony-formation (1, 3, 5, and 7 days) for reverse transcriptase-based polymerase chain reaction (RT-PCR) or are fixed for in situ hybridization. Preosteoblast and osteoblast cultures generate sufficient numbers of cells for Northern or S1 analysis.

While a variety of methods exist for identifying differentially expressed genes, most rely on the subtractive hybridization technique (Liang et al., 1992). However, such procedures tend to be technically daunting and prone to experimental error. Recently, Pardee and co-workers have developed a fingerprinting technique for the comparison of differentially expressed mRNAs (Liang et al., 1992).

This procedure, termed Differential Message Display (DMD), allows the separation and rapid cloning of individual mRNAs by means of the polymerase chain reaction (PCR). DMD utilizes a set of oligonucleotide primers in which the 3' primer is anchored to the polyadenylate tail of this subset of RNAs, and the 5' primer is a short, arbitrary sequence. Following reverse transcriptase-based generation of cDNAs, the mRNA populations defined by these primers are amplified by PCR, in the presence of a radio-labeled dNTP, and resolved on a DNA sequencing gel. Thus, using a number of differing primer-pairs results in detection of differentially expressed messages (e.g., in younger versus older bone cell DMD age comparisons). Subsequently, it was shown that the number of anchored primers could be reduced from twelve to four by using a degenerate base at the penultimate 3' end (Liang et al., 1994).

In another embodiment, genetic alterations associated with the aging process, or disease, can be determined by screening cDNA libraries from elderly individuals. In this procedure, a cDNA library from elderly individuals (of either or both antigenically different groups described above) are evaluated for expressed genes that are not found in younger individuals.

To accomplish this, human bone precursor cells are purified from each age group (e.g., <25 years, and >60 years) and cDNA libraries from each constructed. cDNAs from the younger individuals are pooled, radiolabeled, and used to screen the cDNA library obtained from the human bone precursor cells of the most elderly individuals. Those cDNAs in common between the elderly and younger individuals will hybridize with each other (thus being detected by autoradiography), whereas those unique to the elderly, will not. These latter cDNAs represent genes not expressed in younger individuals.

Likewise, using radiolabeled cDNA from elderly individuals, cDNA libraries from young individuals can be screened for the presence of genes only expressed in bone cells from younger individuals (hence being genes the expression of which is lost during aging). Other comparison envisioned, but not limited to, are contrasts between young, old, and middle aged individuals, or contrasts of different types of osteoporosis and bone disease with healthy individuals.

Finally, the inventors demonstrated that the molecular basis of the differences in normal versus cancer cells could be easily visualized by DMD (Liang et al., 1992). The inventors utilize DMD to identify genes uniquely modified by aging. In these investigations preosteoblasts and osteoblasts from both age groups are evaluated by DMD. Differentially expressed gene fragments are directly sub-cloned from the PCR products (into the pCR1000 vector, Invitrogen), and used as probes for isolating the full length cDNA from appropriate libraries. Moreover, as most sub-cloned fragments are 400–1000 bp, sequencing and gene bank searches identify that sequence or its homology with other genes.

The significance of the mRNA studies is that the increase the inventors' understanding of the regulation of bone protein expression during aging. Comparison of this data determines the level of regulation (i.e. transcription of gene expression or translation into protein), thus linking biochemical control mechanisms to molecular control of gene expression. The mRNA studies confirms immunological-based observations on bone protein expression and extend these data to the RNA level.

The inventors propose isotopic RNA analysis for its sensitivity, and non-isotopic in situ labeling for ease of use, preservation of morphology, and permanence of record. The comparison of Northern (or S1) analysis with in situ hybridization will allow exact evaluation amount of mRNA, as well as identification of the cell types expressing a given message. One problem with in situ hybridization is that it only detects mRNA of relatively abundant copy number. Thus low-copy numbers of bone protein mRNA may go undetected. To overcome this limitation RT-PCR is utilized. Using antisense RNA primers, reverse transcriptase, and 30 cycles of PCR, low copy mRNA signals can be amplified up to 109 fold.

EXAMPLE 8

The Determinants of Human Bone Precursor Cell Proliferation in Low-Shear Environments The physical requirements for optimal bone precursor cell (i.e., osteoprogenitor cell and pre-osteoblast) proliferation both in vivo and ex vivo are poorly understood. In vivo, bone formation most often occurs within an intervening cartilage model (i.e., endochondral ossification). This well-understood bone histogenesis is one of embryonic and post-natal chondrogenesis, which accounts for the shape of bone, and the subsequent modification and calcification of bone cell ECM by osteoblasts. This process results in the formation and elongation of bone during childhood growth and development.

However, there is no evidence that adult trabecular bone formation (the predominant site of calcium metabolism) occurs in an identical fashion. For example, in traumatic bone repair, mesenchymal cells migrate into and organize the hematoma which occurs around a fracture. As a result, a large irregular-shaped bony callus (comprised of woven bone) forms, that subsequently is remodeled into the shape of the original bone. A role for chondrocytes in this process has not been described. Other evidence (from this group) supports the concept that trabecular bone formation is different from the classic endochondral model.

As described above, trabecular bone precursor cells proliferate and organize their extracellular matrix in an osteogenic fashion—without an apparent intervening cartilage model. The inventors have shown that trabecular bone differs from compact bone in its extracellular matrix protein composition, suggesting differences in trabecular osteoblast function (Ninomyia et al. 1990). Nonetheless, it is likely that trabecular bone formation in the adult requires a three-dimensional (osteoid) matrix that is elaborated by the osteoblasts themselves. Moreover, the inventors have demonstrated that osteoprogenitor cell growth in the presence of a three-dimensional fibrin clot (interestingly, one of the major proteins in a hematoma) results in a marked increase in: progenitor cell cellularity, the expression of bone protein antigenic markers, cell size, and cell complexity.

Human bone precursor cell proliferation is likely to be augmented by growth in simulated microgravity environments. This is based on bone precursor cell proliferation from differentiation in rat space-flight studies discussed above (Klement and Spooner, 1993). In addition, Goodwin and associates have documented a remarkable augmentation of cell proliferation in low-shear rotating wall vessle (RWV)-type bioreactors. Their data shows that mesenchymal cell types show an average three to six-fold increase in cell density in these bioreactors reaching a cellularity of approximately $10^7$ cells/mL. Importantly, this increase in cell density was associated with a 75% reduction in glucose utilization as well as an approximate 85% reduction in the enzymatic markers of anabolic cellular metabolism (SGOT and LDH). Further work by Goodwin et al. shows that the growth of mesenchyml cells (kidney and chondrocyte) under low-shear conditions leads to the formation of tissue-like cell aggregates which is enhanced by growing these cells on collagen-coated microcarriers.

Physical Requirements for Bone Precursor Cell Proliferation. The physical requirements for bone precursor cell growth in rotating wall vessels is evaluated by comparing suspension-phase and microcarrier-based cell growth. Four bone cell culture conditions are utilized. The two types of simulated microgravity cultures consist of suspension-phase bone precursor cells only, and simulated microgravity cultures with precursor cells plus microcarrier beads. These cultures are contrasted with control cells cultured in unit-gravity conditions (unit-gravity cultures are performed in tissue culture flasks of equal volume and media-composition; i.e., both cells in suspension and cells cultured on microcarriers). Interestingly, the inventors have recently demonstrated that unit-gravity bone precursor cell growth occurs in type I collagen gels. Collagen-coated microcarrier (Cytodex-3 beads) as described above in the inventors' studies are utilized.

These studies evaluate whether human bone precursor cells require cell:cell interaction (as evident in suspension phase comparisons of simulated-microgravity and unit gravity cultures). Whether human bone precursor cells may require both cell:cell contact and/or cell:ECM interactions is determined. This possibility is determined in microcarrier-based studies in which cells both interact with each other, and with the type I collagen coat of the carrier beads. It is understood that while human bone precursor cells may self-assemble into aggregates in simulated-microgravity suspension-phase cultures, other cell types (lymphocytes and lymphocyte cell lines) show reduced proliferation. However, these are hematopoietic cells which do not generate a solid tissue, such as cartilage or bone.

Quantitative Assessment of Human Bone Precursor Cell Development. Human bone precursor cells are cultured for varying periods under simulated-microgravity conditions. Based on the developmental periods utilized to generate the bone cell data, bone cell development in the RWVs on days three, five, seven, nine, twelve, fourteen, and thirty are evaluated. Total cellularity is evaluated by cell counts, cell-density determination, and evaluation of the frequency of tissue-like aggregates in these cultures. For microcarrier cultures, aggregates are enumerated and the cells treated to remove them from the microcarrier beads. Cultures are stripped of cells by the method of Gospodarowicz, (Gospodarowicz and Ill, 1980; Gospodarowicz et al., 1980) which leaves behind cell-derived extracellular matrix (ECM) and/or beads. Also, previous work has shown that this procedure easily releases mesenchymal cells from cytodex beads, and does not interfere with bone antigen expression (Long et al, 1995).

Multiparameter Flow Cytometry Characterization of Preosteoblasts and Osteoblasts. Single-cell suspensions, taken at specified time-points, are evaluated for developmental markers by multiparameter flow cytometry. Two and three color fluorescence-activated flow cytometry is used to evaluate co-expression of a number of human bone protein markers: osteonectin, osteocalcin, alkaline phosphatase, bone sialoprotein, and osteopontin. The expression of these proteins is also correlated with alterations in cell size (as indicated by forward angle light scatter) and cell complexity (as indicated by right angle light scatter). These studies allow for the evaluation of quantitative differences in both the phenotype and frequency of pre-osteoblasts and osteoblasts as defined by their flow cytometry characteristics.

Osteoprogenitor Cells. Alterations in the frequency of osteoprogenitor cells during simulated microgravity exposure is evaluated. At the times indicated above, samples of cells are removed from the cultures and osteoprogenitor cell numbers are evaluated in fibrin-clot colony-forming assays. These studies determine whether the frequency or proliferative potential of the two classes of osteoprogenitor cell (high proliferating colony-forming progenitor vs. low proliferating, cluster-forming progenitor cells) are differentially modulated under low-shear conditions. Evaluation of the colony cellularity (cells/colony) also determines the proliferative potential of each of these progenitor cell phenotypes.

As mentioned, evidence for a differentiation blockade was noted during real microgravity exposure (Klement and Spooner, 1993). However, the exact level of this blockade is unknown. With the inventors' ability to quantify bone precursor cells, the inventors can locate the level at which such a block occurs for human cells. For example, if a blockade exists between the osteoprogenitor cell and pre-osteoblast then numbers of the former should increase in frequency with an attendant decrease in a pre-osteoblast numbers. A similar alteration in cell ratios is detectable if the blockade is between the pre-osteoblast and osteoblast.

Biochemical and Metabolic Evaluation of Bone Cell Development. In order to evaluate the metabolic status of developing bone precursor cells, simulated microgravity and control cultures are monitored for alterations in glucose utilization, SGOT and LDH enzyme production as described previously (Goodwin et al., 1993). These studies yield information about the efficiency of glucose utilization, gluconeogenesis, and level of cellular damage.

Alterations in the cellular expression of bone proteins as evaluated by flow cytometry (above) by two alternative methods. Bone protein production of both collagenous and non-collagenous proteins are monitored by metabolic ($^{35}$S-methionine) labeling and subsequent immunoprecipitation of the relevant proteins as described by (Greenberg et al., 1990; Kozawa et al., 1989; Tracey et al., 1990). Bone protein quantity is monitored using a number of independent assays. Secretory bone protein release is monitored by soluble-phase RIA. Cellular protein synthesis is monitored by immunoprecipitation of metabolically labeled cells.

Briefly, human bone precursor cells are cultured for various periods as described above, and culture media exchanged for methionine-free media (Gibco) containing 10 $\mu$Ci of $^{35}$S-methionine (4 hours at 37° C.). Cells are washed free of unincorporated label, lysed with triton X-100 and proteins immunoprecipitated with cold TCA. The proteins in the final precipitate are resolved by PAGE and visualized by autoradiography. $^{125}$I-labeled purified bone proteins are run as controls. These protein synthesis studies are correlated with immunocytochemical analysis, performed using an avidin-biotin peroxidase labeled system as described by Long et al. (Long and Heffner, 1988; Long and Dixit, 1990).

In addition, information on the micro-structure of bone cell aggregates is determined by ultrastructural analysis. Both scanning electron microscopy and transmission electron microscopy are employed to analyze the quality and degree of organization occurring within bone tissue-like aggregates as previously described.

EXAMPLE 9

Cytokine and ECM Control of Bone Precursor Cell Proliferation in Low-Shear Microenvironments Once the optimal physical/geometrical requirements for human bone precursor cell expansion in simulated microgravity are determined, the mechanism and/or further expansion of these cells by various osteogenic cytokines is determined. Certain growth factors (or cytokines), in particular TGF-$\beta$1 and bFGF, stimulate the early phases of osteoprogenitor cell proliferation. One potential mechanism of increased ex vivo expansion of bone precursor cells in simulated microgravity is altered responsiveness to mitogenic activation.

As discussed above, glucose metabolism decreases while cell density and tissue aggregate formation increases under simulated microgravity conditions (Goodwin et al, 1993). One reason for this is that increased availability of growth factors and nutrients occurs due to coriolis-force driven admixing within the rotating wall vessel. A correlate of this is that the response of these cells is seemingly heightened at a given concentration of growth factor (i.e. due to improved availability).

The role of differing cytokines in the expansion of bone precursor cells in simulated microgravity is obtained. Cultures with varying concentrations of osteogenic growth factors are initiated. Given their effect on proliferation, TGF-β and bFGF, both alone and in combination are tested. Comparison of cell growth in simulated microgravity and unit gravity cultures utilize all the quantitative methods described above. The inventors also documented differential effects for various cytokines at the early and late phases of bone precursor cell proliferation (e.g., TGF-β, and 25-dihydroxy vitamin $D_3$, respectively). A synergistic interaction likely occurs if bone precursor cells are cultured simultaneously with these-two classes of growth factors under simulated microgravity conditions. The inventors evaluate four relevant combinations of growth factors: TGF-β+BMP; TGF-β+$D_3$; bFGF+BMP and bFGF+$D_3$. Quantitative evaluation of these combinations is performed as outlined above.

Another component of the osteogenic microenvironment is the extracellular matrix. As mentioned, bone extracellular matrix contains both collagenous and non-collagenous proteins. When bone precursor cells are cultured on certain non-collagenous proteins, they show an increase in proliferation in bone cell expression. Moreover, the applicants have shown, using the hematopoietic system as a model, that subpopulations of primitive progenitor cells require both a mitogenic cytokine and a specific extracellular matrix (ECM) molecule in order to proliferate. (Long et al., 1992) Indeed, without this obligate matrix:cytokine (matricrine) signal, the most primitive of blood precursor cells fail to develop in vitro (Long et al., 1992). It is likely that a similar requirement exists for human bone precursor cells. Further it is likely that osteogenic development in simulated microgravity may require the addition of exogenous ECM molecules.

The inventors have demonstrated the importance of three bone ECM proteins in human bone cell growth at unit gravity: osteonectin, osteocalcin, and type I collagen (Long and Ashcraft, 1994). Two additional matrix proteins are of importance: bone sialoprotein and osteopontin (Oldberg et al., 1986; Nomura et al., 1988). These two proteins are believed to be involved in bone formation but their role is unknown.

The function of these ECM molecules, soluble, purified bone ECM proteins are investigated in simulated microgravity and control cultures. Varying amounts of exogenous ECM molecules is added in the presence of a single growth factor (e.g., 25 pM TGF-β, or the optimal factor/concentration defined for simulated microgravity environments as detailed above), to allow precise evaluation of the developmental effects of each extracellular matrix molecule. The combined effects of relevant cytokine and matrix molecules on the expansion of human bone precursor cells in simulated microgravity is determined. Each of the effective cytokines in matrix molecules defined are added at optimal concentrations and cell proliferation evaluated as detailed above.

The above studies show, in a stepwise fashion, (1) the correct physical/geometrical requirement for bone progenitor precursor cell growth in simulated microgravity, (2) the appropriate cytokine or cytokine combinations, and (3) the relevant ECM molecules necessary for human bone precursor cell proliferation. A complex osteogenic microenvironment therefore is reduced to a stepwise evaluation and optimalization of each of its relevant components. These studies define the minimum essential conditions for the ex vivo expansion of human bone precursor cells in simulated microgravity environments.

EXAMPLE 10

The Responsiveness of Developing Bone Precursor Cells to Other Microenvironmental Signals in Simulated-Microgravity.

Developing tissue cells interact with a wide variety of regulators during their ontogeny. Thus, cells interact with each other, with growth-factors, and with extracellular matrix molecules. Each of these interactions is mediated by defined, specific receptor-ligand interactions necessary to both stimulate the cell proliferation and/or motility. Both chemical and/or extracellular matrix gradients exist which signal the cell to move into a defined microenvironment. As well, high concentrations of the attractant, or other signals, next serve to "localize" the cell, thus stopping its non-random walk. Signals which stop and/or regionalize cells in appropriate microenvironments are poorly understood.

The inventors have shown that, in the hematopoietic system, complexes of cytokines and extracellular matrix molecules serve to localize progenitor cells (Long et al. 1992). It is likely that similar mobility (chemotactic) or localization signals exist for bone precursor cells, and mediate their movement into an osteogenic region (such as a fracture). The modulation of these physiological processes in simulated microgravity conditions is investigated.

Figure 10A:
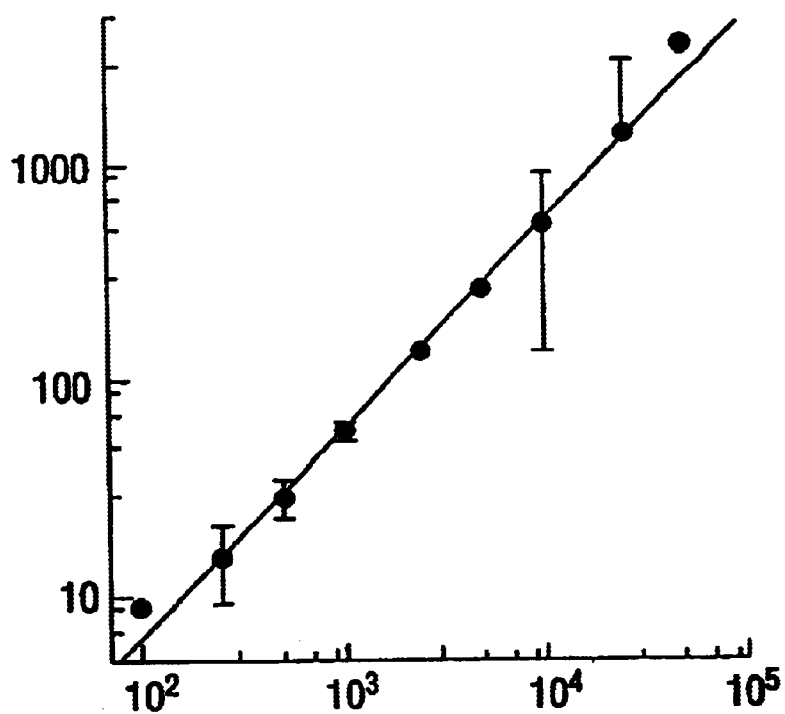
FIG. 10A shows a standard curve of the linear relationship between fluorescent intensity and cell number.

One Precursor Cell Cytoadhesion and Tissue Localization. Recently, the inventors have developed a cytoadhesion assay which employs "caged" fluorochromes to label isolated progenitor cells for subsequent adhesion studies. In this assay, acetylmethylester derivatives of FITC are used to viably label the cells. Upon internalization, intracellular esterases cleave the AM-ester derivative rendering the released fluorochrome relatively impermeable. Importantly, the fluorescence signal is linear with respect to cell number, and as few as several hundred cells can be detected (FIG. 10A). The cytoadhesion assay then consists of the adhesion of caged-fluorochrome labeled cells to purified and/or recombinant proteins which are immobilized onto tissue culture plastic (as described previously (Long and Dixit, 1990; Long et al., 1992)), the removal of non-adherent cells, and quantitation in a fluorescent plate reader.

Figure 10B:
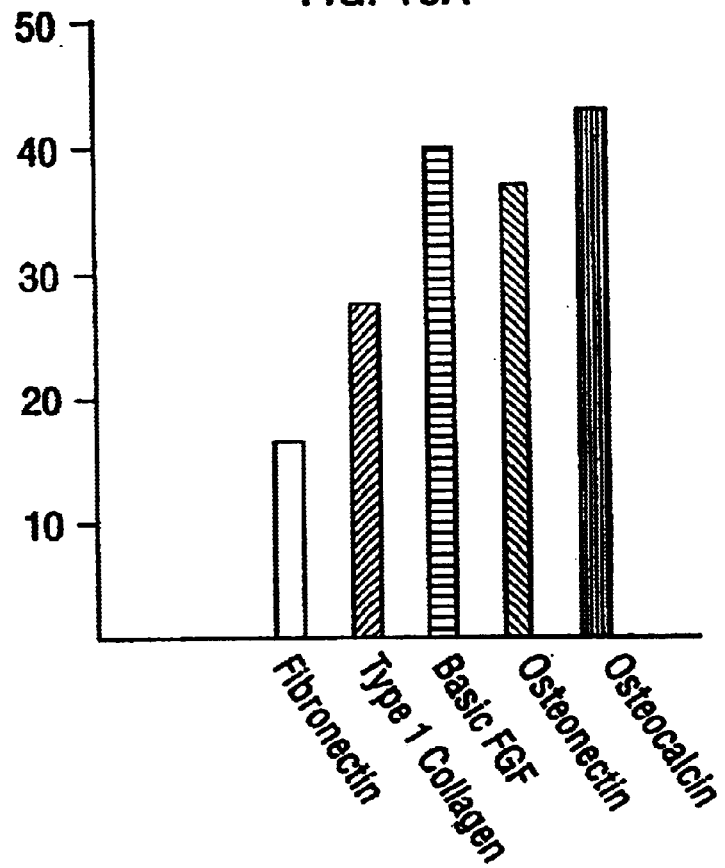
FIG. 10B shows the attachment of human bone precursor cells, purified by immunomagnetic separation, that were labeled with calcein, and adhered to plastic, immobilized proteins. The percent attachment was determined by reading the fluorescent signal of attached cells on the standard curve in FIG. 10A.

The resultant sensitivity of this assay is approximately 100 times greater than other cytoadhesion assays reported previously from this laboratory (Long et al., 1992; Long and Dixit, 1990; Campbell et al., 1990). The inventors utilized this assay in preliminary studies of purified human bone precursor cells to evaluate attachment to extracellular matrix molecules. These data indicate that bone precursor cells express differential attachment capacities to both immobilized bone ECM molecules and immobilized cytokines (FIG. 10B). Previous work showed that hematopoietic progenitor cells bound to both growth factors and ECM molecules (Long et al., 1992; Long and Dixit, 1990; Campbell et al., 1990).

Thus, as divergent cellular phenotypes as bone and hematopoietic cells both demonstrate dual requirements for matrix and cytokine molecules in the localization (adhesion) process. Notably, the binding of progenitor cells to immobilized, solitary cytokines further demonstrates that the presence of growth factors (which are often themselves immobilized within the extracellular matrix (Long, 1992)) is as least partially responsible for the lineage-specific localization of cells. Nonetheless, it is likely that the presence of specific ECM molecules strengthens this localization process.

In order to evaluate the role of cytoadhesion in bone precursor cell proliferation, the unique aspects of a simulated microgravity in which adhesive interactions may be reduced (in the case of a simulated microgravity tissue culture in the absence of microcarriers) or differentially augmented (with microcarriers) is utilized. To perform these studies, cultures of proliferating bone precursor cells are established under optimal cytokine conditions as defined above, or (as a starting point) as defined in unit-gravity conditions. The capacity of simulated microgravity cultured cells to interact (adhere) with both bone cell regulatory cytokines (bFGF, TGF-$\beta$1, and BMP-2) and extracellular molecules (osteonectin, osteocalcin, bone sialoprotein, osteopontin, fibronectin and thrombospondin) is evaluated. The latter two proteins (thrombospondin and fibronectin) are present in bone extracellular matrix, and are important as cytoadhesion molecules in developing tissues (Weiss and Reddi, 1980; Clezardin et al., 1989).

Bone Precursor Cell Chemotaxis. In a likewise fashion, the effects of simulated microgravity on the motility machinery of developing bone precursor cells is investigated. Various bone related growth factors are evaluated for their capacity to direct non-random movement (cytokinesis) and non-random migration (chemotaxis). As mentioned, early bone precursor cells possess the ability to actively migrate into the area of bone injury, there differentiating into bone-forming cells. However, no information exists on the factors or events which signal this important migratory process.

Simulated microgravity-cultured and control cells are evaluated for responsiveness to both known chemotactic factors (chemokines; i.e., interleukin-8, GM-CSF, M-CSF) and for the role of osteogenic growth factors in stimulating either chemokinesis or chemotaxis. In particular, bFGF and TGF-$\beta$1, both powerful regulators of bone progenitor cell proliferation are evaluated. In order to evaluate the effects of microgravity on bone precursor cell migratory capabilities, a panel of known leukocyte chemotactic factors and osteogenic factors in direct comparison to unit gravity control cells is used.

The chemokines are members of a chemotactic cytokine supergene family (Oppenheim et al., 1991). The chemokine-$\alpha$ cytokines are comprised of molecules with their first two cysteines interrupted by an amino acid (C-X-C), and are represented by such molecules as interleukin-8 (IL-8) and platelet factor 4 (PF4). MCP-1 and RANTES are representative of the chemokine-$\beta$ subfamily, and are characterized by an uninterrupted C—C arrangement. The use of IL-8 and MCP-1 allows employment of chemotactic factors which are known to induce migration of a broad spectrum of cells (Oppenheim et al., 1991).

EXAMPLE 11

The Ability of Bone Precursor Cells to Differentiate Into Osteoblast Cells or Affect the Capacity of Osteoblasts to Elaborate an Osteoid Extracellular Matrix in Simulated Microgravity The complete evaluation of bone cell development requires the study of both bone precursor cells (osteoprogenitor cells and pre-osteoblasts) as well as their differentiated progeny, the osteoblasts. It is the osteoblasts that are responsible for the elaboration and mineralization of bone matrix, and the subsequent formation of bone. As mentioned, studies of space-flight and (bed-rest) models of weightlessness indicate that the differentiated function of osteoblasts is compromised in microgravity conditions. As a result, there is a calcium and bone loss, in both periosteal, and trabecular regions, with the latter predominating.

On a cellular level, osteoblasts reduce or lose their capacity to produce osteoid matrix (Klement and Spooner, 1993) with little alteration occurring in osteoclast activity. Finally, microgravity induces a disassociation between bone precursor cell proliferation and differentiation, that results in a differentiation blockade causing an increased number of precursor cells relative to the numbers of differentiated osteoblasts (Klement and Spooner, 1993).

Most of the quantitative data on microgravity-induced bone loss are from whole-animal studies, and tend to be predominantly morphometric and retrospective in nature. Thus, the site of biochemical/molecular defects leading to bone loss can only be identified in simulated microgravity studies. Importantly, such studies cannot be performed on trabecular bone outgrowth cultures for a variety of reasons (limiting cell numbers, lack of purified cells, heterogeneity of cell types present, etc.), and because the principle defect may be a failure of the osteoblast differentiation pathway. That is, cell development may not progress from osteoprogenitor cell to pre-osteoblast, or from pre-osteoblast to osteoblast. Therefore, it is best to examine this problem in a system in which the full spectrum of human bone cell proliferation/differentiation can be evaluated.

Regulation of Osteoblast Cell Differentiation. As described herein, the inventors have developed a system in which isolated and purified bone precursor cells proliferate and differentiate into osteoblast cells. In particular, the inventors have demonstrated that the process of switching serum-free cultures to TGF-$\beta$-driven, serum-containing cultures results in a differentiation of pre-osteoblasts into osteoblast cells. Importantly, the osteoblast cells generate an osteoid extracellular matrix in which non-collagenous bone proteins are deposited and the cells calcify the extracellular matrix.

The effect of simulated microgravity on both the differentiation of pre-osteoblasts into osteoblasts, and the subsequent alterations in differentiated cell (osteoblasts) function is evaluated. As such, the cell culture protocol described above is modified to induce osteoblast cell differentiation. In these studies, simulated microgravity cultures of human bone precursor cells will are run in two phases. The first phase (7–10 days) is an ex vivo expansion step utilizing serum-free cultures containing growth factor/matrix combinations (as defined above) for generation of maximum numbers of bone precursor cells.

During this phase of the cultures, only cellularity and aggregate formation is monitored as an index of culture conditions. At optimal cell density, these cultures are switched to serum-containing, TGF-$\beta$-containing conditions. Subsequent studies (over an additional 7–10 days) evaluate osteoblast cell differentiation patterns and functional capacities.

As described herein, the inventors have defined a multi-parameter flow cytometric analysis of osteoblast cell differentiation markers; these cells increase in cell size, cell complexity, and the expression of multiple markers of bone cell differentiation. The inventors evaluate the capacity of pre-osteoblasts to differentiate into osteoblast cells using this multi-parameter flow cytometric analysis.

In particular, the expression of the bone proteins discussed above plus two additional markers of bone differentiation, alkaline phosphatase and type I collagen are evaluated. Alkaline phosphatase (EC 3.1.3.1) are monitored by both flow cytometry as well as by alkaline phosphatase cytochemistry (Reddi, 1981). This latter procedure distinguishes bone alkaline phosphatase from that of liver based on heat and urea sensitivity. The production and deposition of bone extracellular matrix molecules microgravity-derived osteoblast cells is determined by metabolic labeling and immunoprecipitation using $^{35}$S-methionine immunoprecipitation.

Extracellular Matrix Calcification. Studies on the capacity of simulated microgravity and control culture osteoblast cells to mineralize their surrounding (bone) ECM employ two alternative approaches: metabolic labeling with $^{45}Ca^{++}$ and histochemical analysis utilizing the von Kossa staining procedure. For the calcium labeling studies, two aspects of bone cell calcium metabolism are evaluated: their ability to take up calcium and their ability to deposit calcium into the extracellular matrix.

In these studies, simulated microgravity-expanded osteoblasts are removed from the rotating wall vessel and equilibrium-labeled (briefly, one hour) with $^{45}Ca^{++}$, as described above. Briefly, osteoblasts differentiated in simulated microgravity (on days 3, 5, 7, 14 and 21 post serum-stimulation) are removed and washed 3 times with calcium-free PBS, and metabolically labeled with 50 µCi $^{45}C^{a++}$ (as CaCl$_2$; Amersham, Arlington Heights, Ill.; sp.act. 733 mBq/Mg) for 60 min at 37° C. Following $^{45}C^{a++}$ calcium-equilibration, labeled cells are washed free of unincorporated calcium, resuspended in serum-free tissue culture medium and re-established in the original culture dishes or in simulated-microgravity conditions. An aliquot of $Ca^{++}$-labeled cells are analyzed immediately for $^{45}C^{a++}$ content. Quantification of the amount of $^{45}Ca^{++}$ taken up per cell indicate microgravity-induced differences in calcium uptake, whereas matrix calcium indicates deposition.

For matrix deposition, equibrium-labeled cells are allowed to incorporate cellular $^{45}Ca^{++}$ into ECM. Given that both osteocalcin (BGP) and osteonectin bind calcium, this exogenous cell-labeling procedure precludes fluid-phase $^{45}Ca^{++}$ binding to previously synthesized matrix proteins. Subsequently, cells/ECM are removed with trypsin/EDTA), cells pelleted by centrifugation, and $^{45}Ca^{++}$ incorporation into the trypsin/EDTA extractable ECM determined by scintillation counting. Trypsin-resistant ECM is removed by Triton X-100 extraction as described previously (Gospodarowicz and Ill, 1980; Gospodarowicz et al., 1980) and counted similarly. To control for residual cell contamination, extracts are monitored for DNA content and calcium deposition into the matrix calculated as a total extractable $^{45}Ca^{++}$ corrected for that due to contaminating cells.

The calcium loading studies evaluate, precisely, the uptake and deposition of calcium by human osteoblast cells during their differentiation in simulated microgravity and unit gravity conditions. The histochemical identification of matrix calcium deposition utilizing the von Kossa staining reaction is also evaluated (Heeley and Irving, 1973; Puchtler and Meloan, 1978). The inventors previously correlated the presence of positive von Kossa reactions with the ability of osteoblast cells generated at unit gravity to metabolically deposit calcium in the extracellular matrix. As a prelude to actual space-flight studies, simulated microgravity and control cultures for von Kossa reactivity at the same time points of the calcium incorporation/deposition studies is evaluated. These kinetic studies are correlated with each other, and should further demonstrate the validity of von Kossa reaction as an indicator of calcification in simulated microgravity conditions.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Alitalo, "Induced differentiation of K562 leukemia cells: a model for studies of gene expression in early megakaryoblasts," Leuk. Res., 14:501–514, 1990.

Ash et al., "Osteoclasts derived from haematopoietic stem cells," Nature, 283:669–670, 1980.

Barsh et al., "Peptide mapping of collagen chains using CNBr cleavage of proteins within polyacrylimide gels," Coll. Relat. Res., 1:543–548, 1980.

Briddell and Hoffman, "Cytokine regulation of the human burst-forming unit-megakaryocyte," Blood, 76:516–522, 1990.

Campbell et al., "Hemonectin: a novel hematopoietic adhesion molecule," Prog. Clin. Biol. Res., 352:97–105, 1990.

Campbell et al., "Developmental regulation of granulocytic cell binding to hemonectin," Blood, 76:1758–1764, 1990.

Campbell et al., "Haemonectin, a bone marrow adhesion protein specific for cells of granulocyte lineage," Nature, 329:744–746, 1987.

Campbell et al., "Extracellular matrix promotes the growth and differentiation of murine hematopoietic cells in vitro," J. Clin. Invest., 75:2085–2090, 1985.

Canalis, "Effect of growth factors on bone cell replication and differentiation," Clin. Orth. Rel. Res., 193:246–263, 1985.

Clezardin et al., "Thrombospondin is synthesized and secreted by human osteoblasts and osteosacoma cells," Eur. J. Biochem., 181:721–726, 1989.

Coccia et al., "Successful bone-marrow transplantation for juvenile malignant osteopetrosis," N. Engl. J. Med., 302:701–708, 1980.

DeForge et al., "Biphasic production of IL-8 in lipopolysaccharide (LPS)-stimulated human whole blood," J. Immunol., 148:2133–2141, 1992.

Delmas et al., "Increase in serum bone y-carboxyglutamic acid protein with aging in women," J. Clin. Invest., 71:1316–1321, 1983.

Fedarko et al., "Age-related changes in hyaluronan, proteoglycan, collagen, and osteonectin synthesis by human bone cells," J. Cel. Physiol., 151:215–227, 1992.

Fishman and Hay, "Origin of osteoclasts from mononuclear leukocytes in regenerating newt limbs," *Anat. Rec.*, 143:329–339, 1962.

Friedenstein et al., "Bone marrow osteogenic stem cells: in vitro cultivation and transplantation in diffusion chambers," *Cell Tissue Kinet.*, 20:263–272, 1987.

Gehron Robey et al., "Osteoblasts synthesize and respond to transforming growth factor-type beta (TGF-beta) in vitro," *J. Cell Biol.*, 105:457–463, 1987.

Giancotti and Ruoslahti, "Elevated levels of the alpha 5 beta 1 fibronectin receptor suppress the transformed phenotype of Chinese hamster ovary cells," *Cell*, 60:849–859, 1990.

Given, "Lymphocytes and the Strategy of Gating," Wiley-Liss, New York. 92 pp., 1992.

Goodwin et al., "Reduced shear stress: A major component in the ability of mammalian tissues-to form three-dimensional assembliees in simulated microgravity," *J. Cell Biochem.*, 51:301, 1993.

Gospodarowicz and Ill, "Extracellular matrix and control of proliferation of vascular endothelial cells," *J. Clin. Invest.*, 65:1351–1364, 1980.

Gospodarowicz et al., "Permissive effect of the extracellular matrix on cell proliferation in vitro," *Proc. Natl. Acad. Sci. USA*, 77:4094–4098, 1980.

Greenberg et al., "Transforming growth factor b inhibits endomitosis in the dami human megakaryocyte cell line," *Blood*, 76(3):533–537, 1990.

Gronthos et al., "The STRO-1+ fraction of adult human bone marrow contains the osteogenic precursors," *Blood*, 84:4164–4173, 1994.

Hanamura et al., "Solubilization and purification of bone morphogenetic protein (BMP) from dunn osteosarcoma," *Clin. Orth. Rel. Reg.*, 153:232–240, 1980.

Hattersley and Chambers, "Generation of osteoclastic function in mouse bone marrow cultures: multicellularity and tartarate resistant acid phosphatase are unreliable markers of osteoclastic differentiation," *Endocrinology*, 124:1689–1696, 1989.

Hauschka et al., "Direct identification of the calcium-binding amino acid, gamma-carboxyglutamate, in mineralized tissue," *Proc. Natl. Acad. Sci. USA*, 72:3925–3929, 1975.

Hauschka et al., "Growth factors in bone matrix. Isolation of multiple types by affinity chromatography on heparin-sepharose," *J. Biol. Chem.*, 261:12665–12674, 1986.

Heeley and Irving, "A comparison of histological methods for demonstrating calcification," *Calc. Tiss. Res.*, 12:169–173, 1973.

Holbrock et al., "Costs of musculoskeletal conditions. In The frequency of occurrence, impact and costs of musculoskeletal conditions in the United States," *Amer. Acad. Orthopaedic Surgeons*, Chicago, Ill. 136–173. 1984.

Holland et al., "In vivo expression of mRNA for the Ca++-binding protein SPARC (osteonectin) revealed by in situ hybridization," *J. Cell Biol.*, 105:473–482, 1987.

Horton et al., "Monoclonal antibodies to osteoblastomas (giant cell bone tumors): definition of osteoclastic specific cellular antigens," *Cancer Res.*, 45:5663–5669, 1985.

Ignotz and Massague, "Transforming growth factor-beta stimulates the expression of fibronectin and collagen and their incorporation into the extracellular matrix," *J. Biol. Chem.*, 261:4337–4345M, 1986.

Jotereau and Le Douarin, "The developmental relationship between osteocytes and osteoblasts: A study using the quail-chick nucleus marker in endochondrial ossification," *Dev. Biol.*, 63:253–265, 1978.

Klement and Spooner, "Utilization of microgravity bioreactors for differentiation of mammalian skeletal tissue," *J. Cell Biochem*, 51:252–256, 1993.

Kozawa et al., "Possible involvement of protein kinase C in proliferation and differentiation of osteoblast-like cells," *FEBS Lett.*, 243:183–185, 1989.

Lawrence and Singer, "Intracellular localization of messanger RNAs for cytoskeletal proteins," *Cell*, 45:407–415, 1986.

Lawrence and Springer, "Leukocytes roll on a selection at physiologic shear flow rates: Distinction from and prerequisite for adhesion through integrins," *Cell*, 65:859–873, 1991.

Le Douarin, "A feulgin-positive nucleolus," *Exp. Cell Res.*, 77:459–469, 1973.

Liang and Pardee, "Differential display of eukaryotic messanger RNA by means of the polymerase chain reaction," *Science*, 257:967–970, 1992.

Liang et al., "Impaired bone activity in aged rats: alterations at the cellular and molecular levels," *Bone*, 13:435–441. 1992.

Liang et al., "Distribution of eukaryotic mRNAs by means of differential display: Refinements and optimization," *Nucleic Acids Res.*, 21:3269–3275, 1994.

Liang et al., "Differentia;l display and cloning of messanger RNAs from human breast cancer versus mammary epithelial cells," *Cancer Res.*, 52:6966-6962, 1992.

Linkhart et al., "Characterization of mitogenic activities extracted from bovine bone matrix," *Bone*, 7:479–487, 1986.

Long, "Blood cell cytoadhesion molecules," *Exp. Hematol.*, 20:288–301, 1992.

Long, "Population heterogeneity among cells of the megakaryocyte lineage," *Stem Cells*, 11:33–40, 1993.

Long and Ashcraft, "Regulation of human bone marrow-derivedosteoprogenitor cells by osteogenic growth factors," Submitted, 1994.

Long et al., "Human hematopoietic stem cell adherence to cytokines and matrix molecules," *J. Clin. Invest.*, 90:251–255, 1992.

Long and Dixit, "Thrombospondin functions as a cytoadhesion molecule for human hematopoietic progenitor cells," *Blood*, 75:2311–2318, 1990.

Long et al., "Phorbol diesters stimulate the development of an early murine progenitor cell. The burstforming unit-megakaryocyte," *J. Clin. Invest.*, 67:431–438, 1985.

Long and Heffner, "Detection of human megakaryocyte antigens by solid-phase radioimmunoassay," *Exp. Hematol.*, 16:62–70, 1988.

Long et al., "Cholera toxin and phorbol diesters synergistically modulate murine hematopoietic progenitor cell proliferation," *Exp. Hematol.*, 16:195–200, 1988.

Long et al., "Regulation of megakaryocyte potential in human erythroleukemia cells," *J. Clin. Invest.*, 85:1072–1084, 1990.

Long et al., "Synergistic regulation of human megakaryocyte development," J. *Clin. Invest.*, 82:1779–1786, 1988.

Long et al., "Role of phorbol diesters in in vitro murine megakaryocyte colony formation," *J. Clin. Invest.*, 74:1686–1692, 1984.

Long et al., "Regulation of human bone marrow-derived osteoprogenitor cells by osteogenic growth factors," *J. Clin. Invest.*, 95:881, 1995.

Long et al., "Immature megakaryocytes in the mouse: Physical characteristics, cell cycle status, and in vitro responsiveness to thrombopoietic stimulatory factor," *Blood*, 59:569–575, 1982.

Long et al., "Expression of bone-related proteins in the human hematopoietic microenvironment," *J. Clin. Invest.*, 86:1387–1395, 1990.

Luria et al., Bone formation in organ cultures of bone marrow," *Cell Tissue Res.*, 248:449–454, 1987.

Mage, "Isolation of T and B cells using panning techniques. In Current protocols in immunology. J. E. Coligan, A. M. Kruisbeek, E. M. Sevach, and W. Strober, editors. J. Wiley and Sons, New York. 3.5.1–3.5.6, 1992.

Massague, "The TGF-beta family of growth and differentiation factors," *Cell*, 49:437–438, 1987.

McNally et al., "Optimizing electroporation parameters for a variety of human hematopoietic cell lines," *BioTechniques*, 6:882–883, 1988.

Metcalf, "The molecular control of cell division, differentiation commitment and maturation in haematopoietic cells," *Nature*, 339:27–30, 1989.

Metcalf and Nicola, "Proliferative effects of purified granulocyte colony-stimulating factor (G-CSF) on normal mouse hemopoietic cells," *J. Cell Physiol.*, 116:198–206, 1983.

Muthukumaran and Reddi, "Bone matrix-induced local bone induction," *Clin. Orth. Rel. Res.*, 200:159–164, 1985.

Nimni et al., "Changes in the ratio of non-calcified collagen to calcified collagen in human vertebrae with advancing age," *Connect. Tissue Res.*, 29:133–140, 1993.

Ninomyia et al., "Heterogeneity of human bone," *J. Bone Min. Res.*, 5:933–937, 1990.

Noda and Vogel, "Fibroblast growth factor enhances type β1 transforming growth factor gene expression in osteoblast-like cells," *J. Cell Biol.*, 109:2529–2535, 1989.

Nomura et al., "Developmental expression of 2ar (osteopontin) and SPARC (osteonectin) RNA as revealed by in situ hybridization," *J. Cell Biol.*, 106:441–450, 1988.

Oldberg et al., "Cloning and sequence analysis of rat bone sialoprotein (osteopontin) cDNA reveals an ArgGly-Asp cell-binding sequence," *Proc. Natl. Acad. Sci. USA*, 83:8819–8823, 1986.

Oppenheim et al., "Properties of the novel proinflamitory supergene "Intercrine" cytokine family," *Annu. Rev. Immunol.*, 9:617, 1991.

Pfeilschifter et al., "Mitogenic responsiveness of human bone cells in vitro to hormones and growth factors decreases with age," *J. Bone Miner. Res.*, 8:707–717, 1993.

Price et al., "Developmental appearance of the vitamin K-dependent protein of bone during calcification. Analysis of mineralizing tissues in human, calf, and rat," *J. Biol. Chem.*, 256:3781–3784, 1981.

Price et al., "Characterization of a gamma-carboxyglutamic acid-containing protein from bone," *Proc. Natl. Acad. Sci. USA*, 73:1447–1451, 1976.

Puchtler and Meloan, "Demonstration of phosphates in calcium deposits: a modification of von Kossa's reaction," *Histochemistry*, 56:177–185, 1978.

Reddi, "Cell biology and biochemistry of endochondral bone development," *Coll. Res.*, 1:209–226, 1981.

Reh and Gretton, "Retinal pigmented epithelial cells induced to transdifferentiate to neurons by laminin," *Nature*, 330:68–71, 1987.

Rodan et al., "Opposing effects of fibroblast growth factor and pertussis toxin on alkaline phosphatase, osteopontin, osteocalcin, and type I collagen mRNA levels in ROS 17/2.8 cells," *J. Biol. Chem.*, 264:19934–19941, 1989.

Roholl et al., "Evidence for a diminished maturation of preosteoblasts into osteoblasts during aging in rats: an ultrastructural analysis," *J. Bone Miner. Res.*, 9:355–366, 1994.

Ruoslahti and Pierschbacher, "New perspectives in cell adhesion: RGD and integrins," *Science*, 238:491–497, 1987.

Schmetzer and Gerhartz, "Immunological phenotyping in situ of myeloid colonies in agar cultures," *Exp. Hematol.*, 15:877–882, 1987.

Shull et al., "Identification of a vitamin D responsive protein on the surface of human osteosarcoma cells," *Proc. Natl. Acad. Sci. USA*, 86:5405–5410, 1989.

Singer et al., "Optimization of in situ hybridization using isotopic and non-isotopic detection methods," *BioTechniques*, 4:230–250, 1986.

Somerman et al., "Mechanism of fibroblast attachment to bone extracellular matrix: Role of a 44 kilodalton bone phosphoprotein," *J. Bone Min. Res.*, 2:259–265. 1987.

Sporn and Roberts, "Autocrine growth factors and cancer," *Nature*, 313:745–747, 1985.

Stenner et al., "Monoclonal antibodies to native noncollagenous bone-specific proteins," Proc. Natl. Acad. Sci. USA, 81:2868–2872, 1984.

Taniguchi et al., "Transforming growth factor beta 1-induced cellular heterogeneity in the periosteum of rat parietal bones," *Calcif. Tissue Int.*, 53:122–126, 1993.

Termine et al., "Osteonectin, a bone-specific protein linking mineral to collagen," *Cell*, 26:99–105, 1981.

Termine, "Cellular activity, matrix proteins, and aging bone," *Exp. Gerontol.*, 1990.

Turksen and Aubin, "Positive and negative immunoselection for enrichment of two classes of osteoprogenitor cells," *J. Cell Biol.*, 114:373–384, 1991.

Urist et al., "Bone cell differentiation and growth factors," *Science*, 220:680–686, 1983.

Urist et al., "Human bone morphogenic protein (hBMP)," *Proc. Soc. Exp. Biol. Med.*, 173:194–199, 1983.

Van Vasselaer et al., "Characterization and purification of osteogenic cells from murine bone marrow by two-color cell sorting using anti-Sca-1 monoclonal antibody and wheat germ agglutinin," *Blood*, 84:753–763, 1994.

Weiss and Reddi, "Synthesis and localization of fibronectin during collagenous matrix-mesenchymal cell interaction and differentiation of cartilage and bone in vivo," *Proc. Natl. Acad. Sci. USA*, 77:2074–2078, 1980.

Wicha et al., "Extracellular matrix promotes mammary epithelial growth and differentiation in vitro," *Proc. Natl. Acad. Sci. USA*, 79:3213–3217, 1982.

Wong and Ng, "Maturation-associated changes in the cellular composition of mouse calvariae and in the biochemical characteristics of calvarial cells separated into subclasses on Percoll density gradients," *J. Bone Miner. Res.*, 7:701–708, 1992.

Wozney et al., "Novel regulators of bone formation: molecular clones and activities," *Science*, 242:1528–1534. 1988.

Wysocki and Sato, ""Panning" for lymphocytes: A method for cell selection," *Proc. Natl. Acad. Sci. USA*, 75:2844–2848, 1978.

What is claimed is:

1. A method for identifying a subject at risk of developing an age-related bone disorder, comprising the steps of:

obtaining a population of cells from said subject that includes bone precursor cells;

enriching said population of cells for human bone precursor cells; and quantifying the amount of osteocalcin or osteonectin expressed by said bone precursor cells, wherein an increased amount of osteocalcin or osteonectin, in comparison to the amount expressed by the bone precursor cells of a young or middle-aged person, is indicative of said subject being at risk of developing an age-related bone disorder.

2. The method of claim 1, wherein said population of cells is obtained from a bone marrow sample of said subject.

3. The method of claim 1, wherein said population of cells is obtained from a peripheral blood sample of said subject.

4. The method of claims 1, wherein said population of cells is enriched for human bone precursor cells by a method including the steps of equilibrium-density centrifugation separation and plastic adherence separation.

5. The method of claim 4, wherein said population of cells is enriched for human bone precursor cells by a method including the steps of equilibrium-density centrifugation, plastic adherence and separation according to cell size.

6. The method of claim 4, wherein said population of cells is enriched for human bone precursor cells by a method including the steps of equilibrium-density centrifugation, plastic adherence and immunomagnetic separation.

7. The method of claim 1, comprising quantifying the amount of osteocalcin.

8. The method of claim 1, comprising quantifying the amount of osteonectin.

9. The method of claim 1, comprising quantifying the amount of osteonectin and the amount of osteocalcin.

10. The method of claim 1, wherein quantifying the amount of osteocalcin or osteonectin is achieved by subjecting said human bone precursor cells to fluorescence activated flow cytometry.

11. The method of claim 1, wherein said age-related bone disorder is osteoporosis.

* * * * *

UNITED STATES PATENT AND TRADEMARK OFFICE
CERTIFICATE OF CORRECTION

PATENT NO. : 6,740,493 B1  Page 1 of 1
APPLICATION NO. : 08/793053
DATED : May 25, 2004
INVENTOR(S) : Michael W. Long et al.

It is certified that error appears in the above-identified patent and that said Letters Patent is hereby corrected as shown below:

In column 1, lines 11-13, delete "The U.S. Government may own rights in the present invention pursuant to grant numbers PO1-AG-08777 and 43460" and insert --This invention was made with government support under grant number AG-08777 awarded by the National Institute of Ageing, National Institutes of Health. The government has certain rights in the invention.-- therefor.

Signed and Sealed this

Twentieth Day of January, 2009

JON W. DUDAS
*Director of the United States Patent and Trademark Office*